(12) United States Patent
Verdin et al.

(10) Patent No.: US 10,106,818 B2
(45) Date of Patent: Oct. 23, 2018

(54) DUAL-COLOR HIV REPORTER SYSTEM FOR THE DETECTION OF LATENTLY-INFECTED CELLS

(71) Applicant: THE J. DAVID GLADSTONE INSTITUTES, San Francisco, CA (US)

(72) Inventors: Eric M. Verdin, Mill Valley, CA (US); Vincenzo Calvanese, West Hollywood, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 14/910,665

(22) PCT Filed: Aug. 14, 2014

(86) PCT No.: PCT/US2014/050998
§ 371 (c)(1),
(2) Date: Feb. 5, 2016

(87) PCT Pub. No.: WO2015/023811
PCT Pub. Date: Feb. 19, 2015

(65) Prior Publication Data
US 2016/0186210 A1    Jun. 30, 2016

Related U.S. Application Data

(60) Provisional application No. 61/866,847, filed on Aug. 16, 2013.

(51) Int. Cl.
| | | |
|---|---|---|
| *C12N 15/86* | (2006.01) |
| *C12Q 1/6897* | (2018.01) |
| *C12Q 1/70* | (2006.01) |
| *A61K 35/17* | (2015.01) |
| *C12N 7/00* | (2006.01) |

(52) U.S. Cl.
CPC .............. *C12N 15/86* (2013.01); *A61K 35/17* (2013.01); *C12N 7/00* (2013.01); *C12Q 1/6897* (2013.01); *C12Q 1/703* (2013.01); *C12N 2740/16011* (2013.01); *C12N 2740/16043* (2013.01); *C12N 2830/60* (2013.01)

(58) Field of Classification Search
CPC .......... C12N 15/86; C12N 2740/16043; C12N 2740/16011
See application file for complete search history.

(56) References Cited

U.S. PATENT DOCUMENTS

| | | |
|---|---|---|
| 4,756,907 A | 7/1988 | Beck et al. |
| 5,728,074 A | 3/1998 | Castellano et al. |
| 6,086,909 A | 7/2000 | Harrison et al. |
| 6,096,010 A | 8/2000 | Walters et al. |
| 6,146,361 A | 11/2000 | DiBiasi et al. |
| 6,221,053 B1 | 4/2001 | Walters et al. |
| 6,248,095 B1 | 6/2001 | Giambattista et al. |
| 6,277,099 B1 | 8/2001 | Strowe et al. |
| 6,476,079 B1 | 11/2002 | Jukarainen et al. |
| 6,479,507 B2 | 11/2002 | Cheng et al. |
| 6,492,389 B1 | 12/2002 | Huang et al. |
| 6,509,361 B1 | 1/2003 | Weier et al. |
| 6,984,718 B2 | 1/2006 | Zhang et al. |
| 7,183,047 B2 | 2/2007 | Brack-Werner et al. |
| 2002/0198214 A1 | 12/2002 | Mavunkel et al. |
| 2003/0013078 A1 | 1/2003 | Blair et al. |
| 2003/0157693 A1 | 8/2003 | Verdin et al. |
| 2008/0118494 A1 | 5/2008 | Kutsch et al. |
| 2009/0306131 A1 | 12/2009 | Verdin et al. |
| 2015/0133434 A1 | 5/2015 | Ott et al. |

FOREIGN PATENT DOCUMENTS

WO    WO 2011146612    11/2011

OTHER PUBLICATIONS

Calvanese, V., et al., 2013, Dual-color HIV reporters trace a population of latently infected cells and enable their purification, Virol. 446:283-292.*
Blankson et al; (2000) "Biphasic decay of latently infected CD4+ T cells in acute human immunodeficiency virus type 1 infection"; J Infect Dis. 182(6):1636-42. Epub Nov. 8, 2000.
Calvanese et al; (2013) "Dual-color HIV reporters trace a population of latently infected cells and enable their purification"; Virology 446(1-2): pp. 283-292.
Contreras et al; (2009) "Suberoylanilide hydroxamic acid reactivates HIV from latently infected cells"; J Biol Chem. 284(11):6782 Epub Jan. 9, 2009.
Dahabieh et al, (2013) "A doubly fluorescent HIV-1 reporter shows that the majority of integrated HIV-1 is latent shortly after infection"; J Virol. Apr. 2013;87(8):4716-27.
Gozlan et al.; (1998) "Human immunodeficiency virus type 1 induction mediated by genistein is linked to cell cycle arrest in G2"; J Virol. 72(10):8174-80.
Hakre et al., (2012) "HIV latency: experimental systems and molecular models"; FEMS Microbiol Rev. 36(3):706-16, U.S. Pat. No. 6,984,718.

(Continued)

*Primary Examiner* — Jeffrey S Parkin
(74) *Attorney, Agent, or Firm* — Michael B. Rubin; Bozicevic, Field & Francis LLP

(57) ABSTRACT

The present disclosure provides for recombinant nucleic acids, and cells and virions comprising the recombinant nucleic acids, that can be used to identify, isolate, and/or purify cells latently infected with immunodeficiency virus. A subject recombinant nucleic acid includes (a) a first nucleotide sequence encoding a first reporter polypeptide that produces a first detectable signal, where the first nucleotide sequence is operably linked to an immunodeficiency virus promoter and is translated as an early gene; and (b) a second nucleotide sequence encoding a second reporter polypeptide that produces a second detectable signal that is distinguishable from the first detectable signal, where the second nucleotide sequence is operably linked to a non-immunodeficiency virus promoter. In some aspects, the first and second nucleotide sequences are both positioned between a shared 5' long terminal repeat (LTR) and a shared 3' LTR. Also provided are related methods.

15 Claims, 28 Drawing Sheets
Specification includes a Sequence Listing.

(56) References Cited

OTHER PUBLICATIONS

Karn, Jonathan et al; (2012) "Transcriptional and Post-transcriptional Regulation of HIV-1 Gene Expression"; Cold Spring Harb Perspect Med 2012;4:a006916; pp. 1-17.
Krishnan and Zeichner; (2004) "Host cell gene expression during human immunodeficiency virus type 1 latency and reactivation and effects of targeting genes that are differentially expressed in viral latency"; J Virol. 78(17):9458-9473.
Lalezari et al; (2003) "Enfuvirtide, an HIV-1 fusion inhibitor, for drug-resistant HIV infection in North and South America"; N Engl J Med. 348(22):2175-85. Epub Mar. 13, 2003.
Li et al: (2012) "SLIC: a method for sequence- and ligation-independent cloning"; Methods Mol Biol. 852:51-59.
Jordan et al., (2003) "HIV reproducibly establishes a latent infection after acute infection of T cells in vitro"; EMBO J. 22(8):1868-1877.
Williams, SA et al: (2004) "Prostratin antagonizes HIV latency by activating NF-kappaB"; J Biol Chem. 279(40):42008-17. Epub Jul. 28, 2004.
Zhu, Jian et al; (2012) "Reactivation of latent HIV-1 by inhibition of BRD4"; Cell Rep. 2(4):807-816: Epub Oct. 4, 2012.
Chiba-Mizutani et al (2006) "Use of new T-cell-based cell lines expressing two luciferase reporters for accurately evaluating susceptibility to anti-human immunodeficiency virus type 1 drugs"; Journal of Clinical Microbiology, vol. 45, No. 2; pp. 477-487.

\* cited by examiner

Figure 1
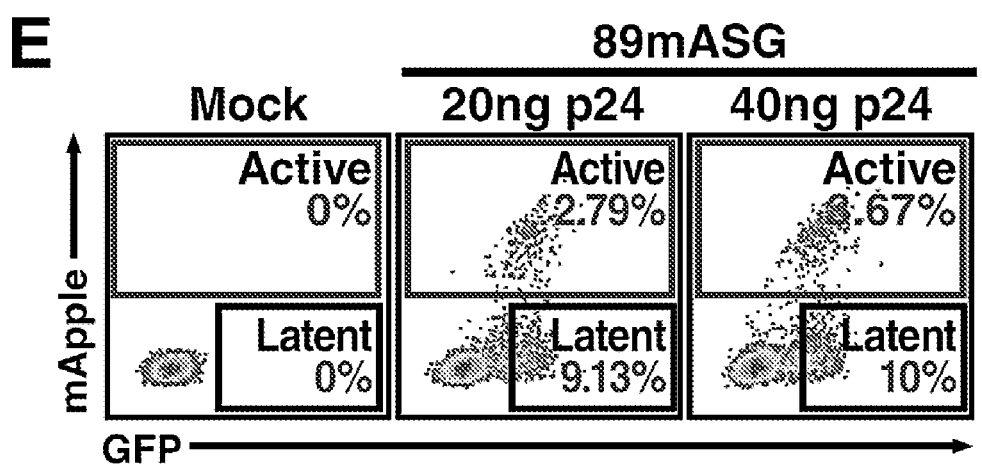
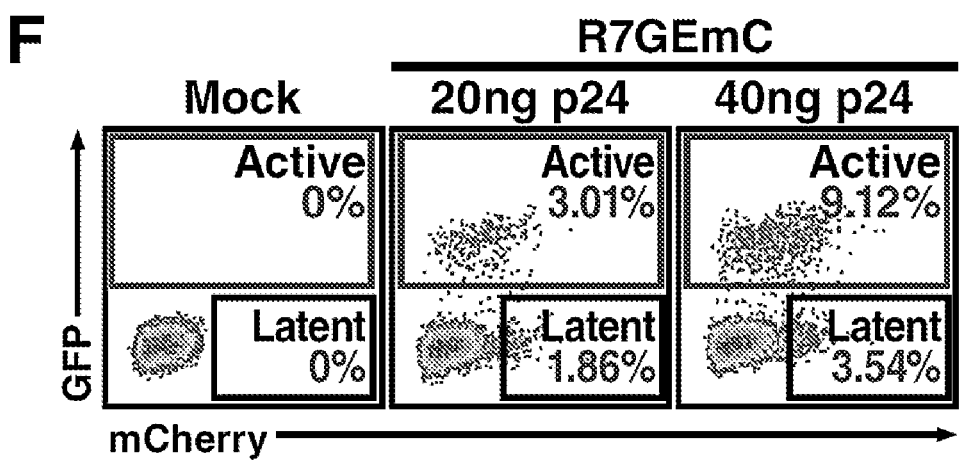

Figure 2
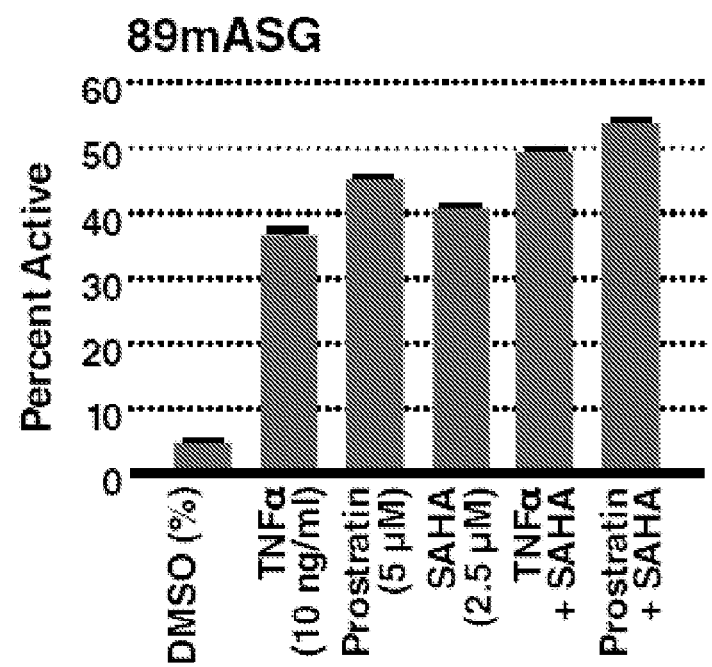
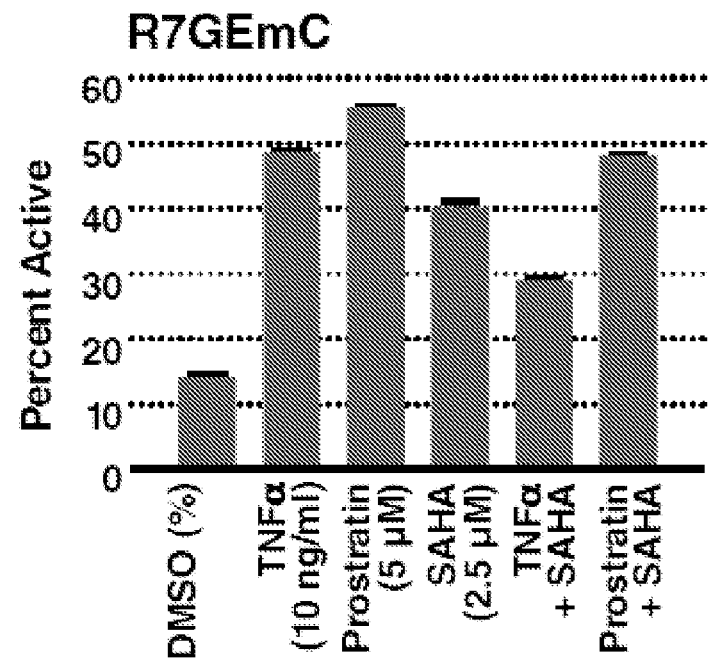

Figure 2
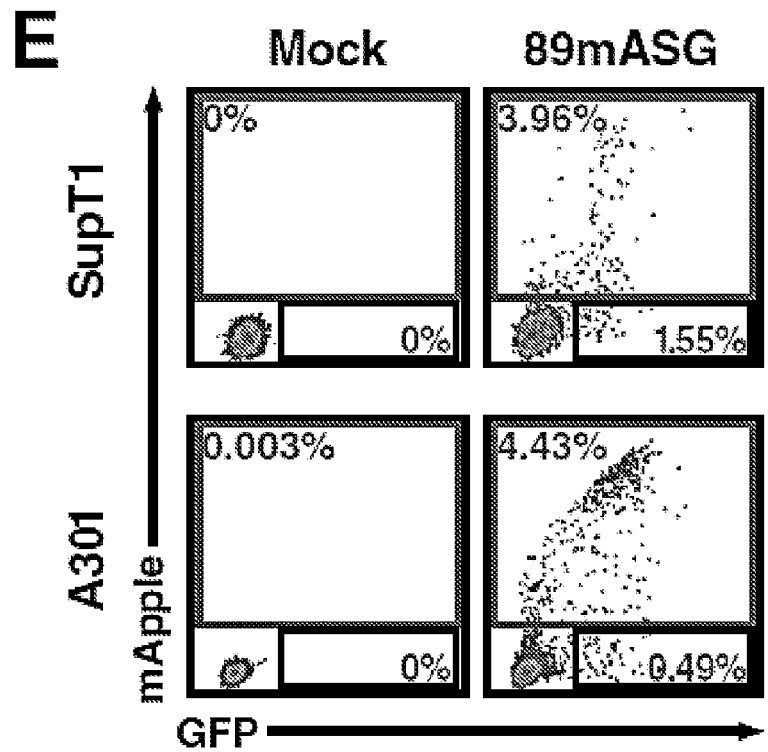
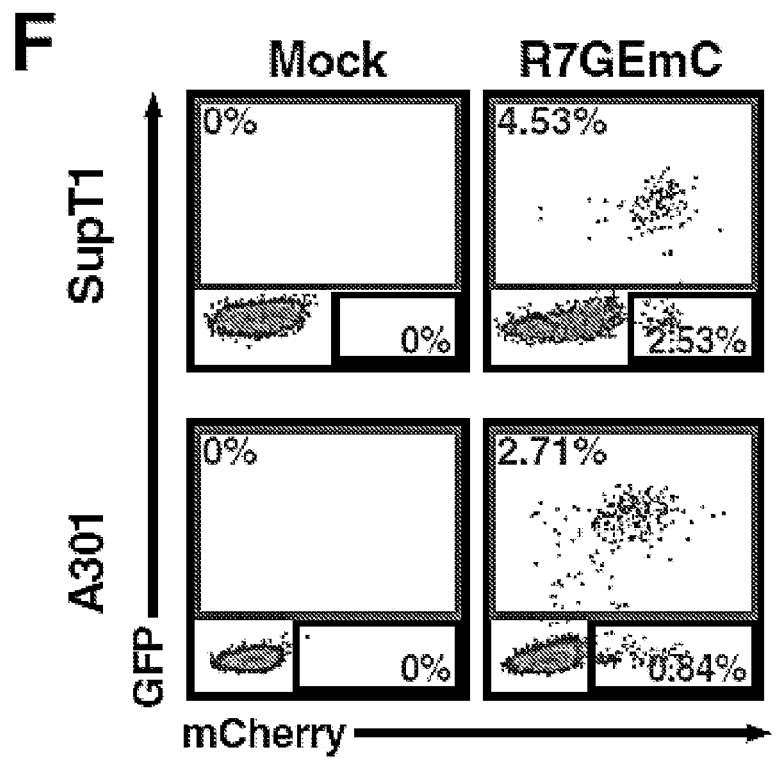

G

H

Figure 6
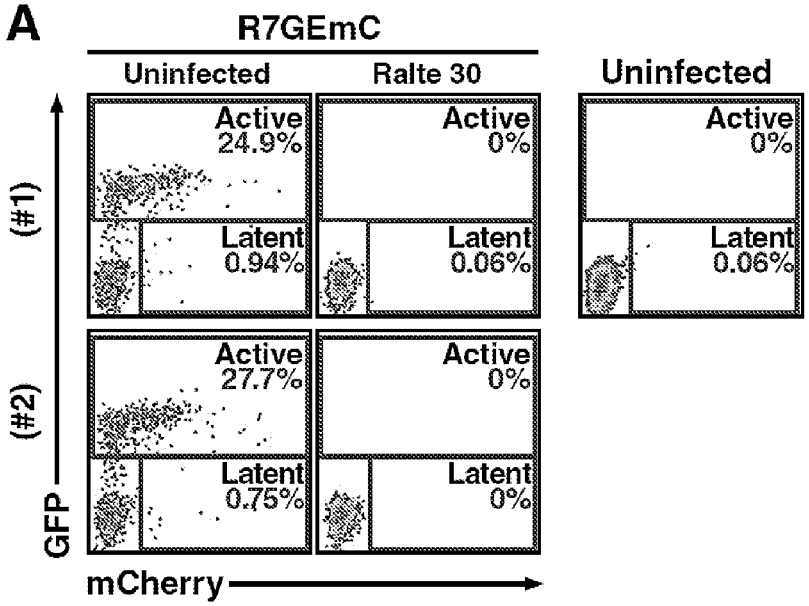
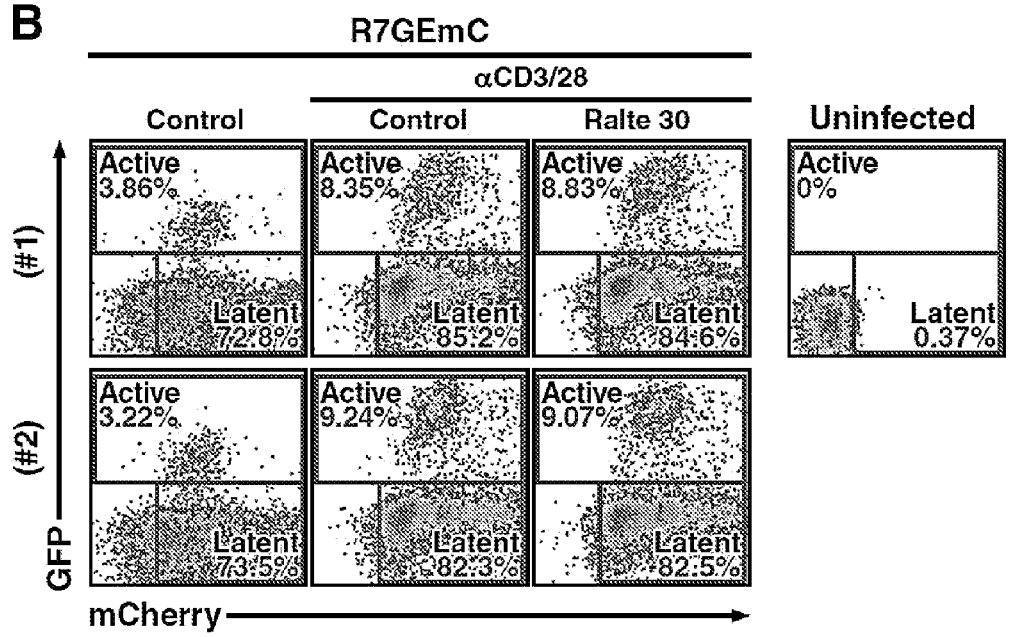

Figure 7

| Position | Compound | Function | % React. | Receptor | Rec. class | II messenger |
|---|---|---|---|---|---|---|
| 01-F11 | AG 18 | EGFR/PDGFR-kinase inhibitor | 17.10 | | | |
| 01-G08 | AG 99 | EGFR-kinase inhibitor | 14.22 | | | |
| 01-M12 | (+)-Tyrphostin B44 | EGFR-kinase inhibitor | 11.21 | EGFR | TyrK-R | MAPK, Akt, JNK, IP3, Ca++ |
| 01-M04 | AG 490 | EGFR-kinase inhibitor; JAK2, JAK3 inhibitor | 14.50 | | | |
| 01-B17 | AG 555 | Potent EGFR-kinase inhibitor | 16.43 | | | |
| 01-A18 | AG 494 | Potent EGFR-kinase inhibitor | 8.39 | | | |
| 02-L10 | Genistein | EGFR kinase inhibitor; ER and PPARγ ligand | 9.40 | | | |
| 02-I18 | SB 202190 | Potent, selective inhibitor of p38 MAPK | 9.66 | p38 | Kinase | MAPK |
| 02-F24 | SB 203580 hydrochloride | Selective inhibitor of p38 MAPK | 9.44 | | | |
| 02-C08 | NBQX disodium salt | AMPA receptor blocker; Kainate rec. blocker | 9.66 | Glutamate | ion channel | Ca++ |
| 02-D14 | SIB 1893 | mGlu5 antag.; mGlu4 positive modulator | 5.15 | | GPCR | |
| 02-M12 | LY 294002 hydrochloride | Selective PI3-kinase inhibitor | 11.21 | PI3K | Kinase | DAG, IP3 |
| 02-M10 | Quercetin | Non-selective PI3-kinase inhibitor | 10.60 | | | Ca++ |
| 02-H20 | (-)-Terreic acid | BTK selective inhibitor | 26.56 | BTK | Kinase | |
| 02-F17 | Cyclopiazonic Acid | SERCA ATPase Inhibitor | 28.78 | | | Ca++ |
| 03-D04 | (±)-Bay K 8644 | Ca++-channel activator (L-type) | 7.01 | Ca++ chan. | ion channel | Ca++ |
| 03-D05 | (S)-(-)-Bay K 8644 | | 6.08 | | | |
| 03-D16 | Linopirdine dihydrochloride | KCNQ channel blocker | 7.37 | K+ chan. | ion channel | Ca++ |
| 02-A08 | Piribedil dihydrochloride | Dopamine D3 receptor agonist | 8.67 | DOPA | GPCR | cAMP |
| 02-C12 | GR 55562 dihydrochloride | 5-HT1B antagonist | 8.47 | 5-HT | GPCR | cAMP |
| 03-O08 | Ritanserin | Potent 5-HT2 antagonist | 6.58 | 5-HT | GPCR | DAG, IP3, Ca++ |
| 03-H17 | CI 898 trihydrochloride | Dihydrofolate reductase inhibitor | 5.59 | DHFR | Enzyme | |
| 01-E09 | Dilazep dihydrochloride | Adenosine uptake inhibitor | 11.68 | Pump | Pump | Adenosin |
| 03-J02 | SB 216763 | Potent, selective GSK-3 inhibitor | 9.79 | GSK-3 | Kinase | |
| 03-C06 | NSC 95397 | Selective Cdc25 phosphatase inhibitor | #100.68 | cdc25 | Phosphatase | |
| 01-E15 | 2-(1-Thienyl)ethyl 3,4-dihydroxybenzylidenecyanoacetate | 5-, 12-, 15-Lipoxygenase inhibitor | 16.74 | LOX | Enzyme | |
| 02-J20 | Resveratrol | Cyclooxygenase inhibitor, Sirt1 activator, Egr1 | 8.09 | | Enzyme, Kinase | |
| 03-F03 | Piceatannol | Syk tyrosine kinase inhibitor, Sirt1 activator | 12.91 | | Enzyme, Kinase | |

FIGURE 10
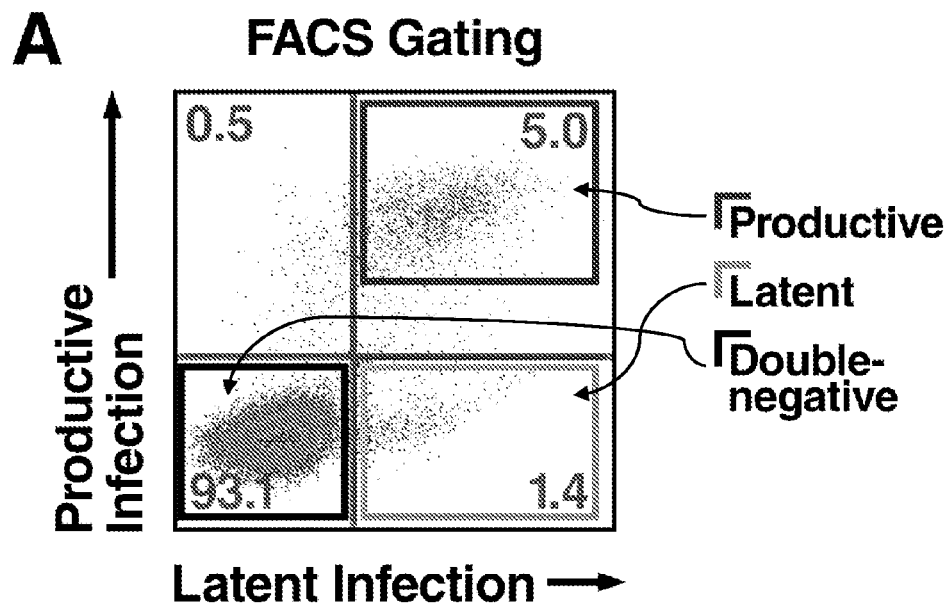
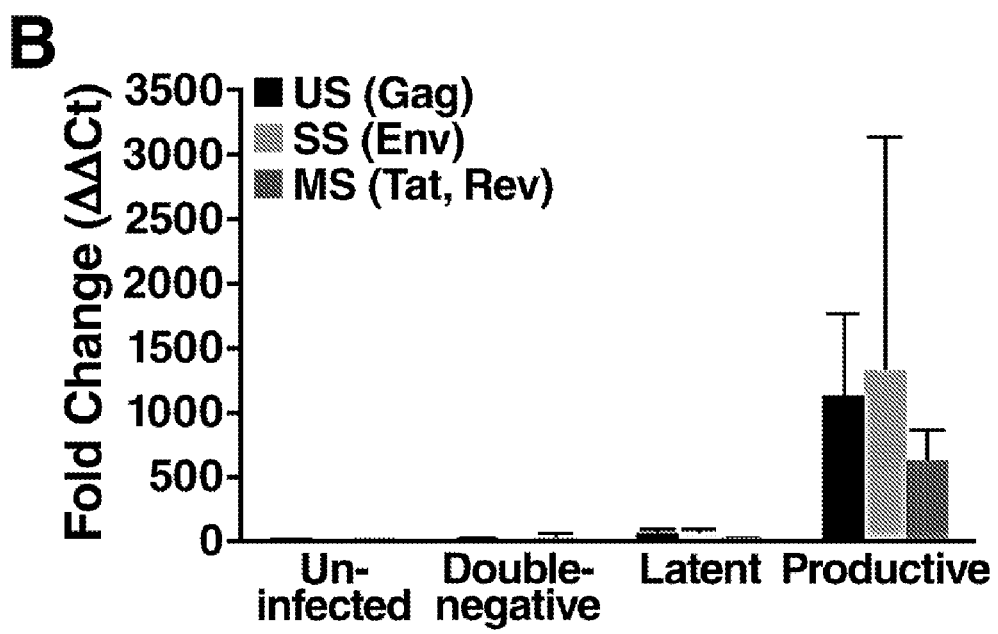

FIGURE 10
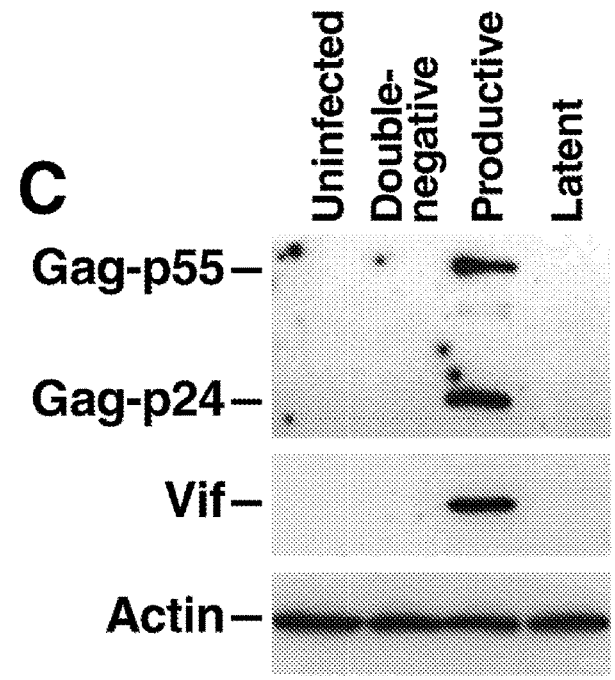
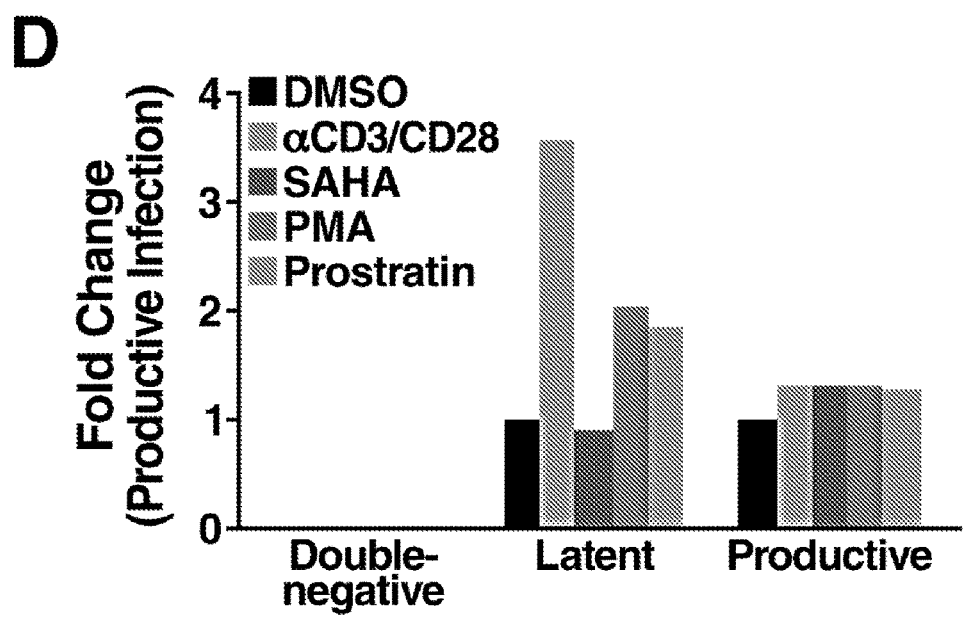

SEQUENCE LISTING

```
<160> NUMBER OF SEQ ID NOS: 45

<210> SEQ ID NO 1
<211> LENGTH: 37
<212> TYPE: DNA
<213> ORGANISM: Artificial sequence
<220> FEATURE:
<223> OTHER INFORMATION: Synthetic nucleic acid sequence

<400> SEQUENCE: 1
ggaaagggct tgctataag atggtgagca agggcga                              37

<210> SEQ ID NO 2
<211> LENGTH: 40
<212> TYPE: DNA
<213> ORGANISM: Artificial sequence
<220> FEATURE:
<223> OTHER INFORMATION: Synthetic nucleic acid sequence

<400> SEQUENCE: 2
tatatctggc ccgtacatcg ttacttgtac agctcgtcca                          40

<210> SEQ ID NO 3
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 3
cttatagcaa agcccttcc                                                 20

<210> SEQ ID NO 4
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 4
cgatgtacgg gccagatata                                                20
```

<210> SEQ ID NO 5
<211> LENGTH: 26
<212> TYPE: DNA
<213> ORGANISM: Artificial sequence
<220> FEATURE:
<223> OTHER INFORMATION: Synthetic nucleic acid sequence

<400> SEQUENCE: 5
gctttacttg tacagctcgt ccatgc                                          26

<210> SEQ ID NO 6
<211> LENGTH: 27
<212> TYPE: DNA
<213> ORGANISM: Artificial sequence
<220> FEATURE:
<223> OTHER INFORMATION: Synthetic nucleic acid sequence

<400> SEQUENCE: 6
ctcatgagct gtagatctta gccactt                                         27

<210> SEQ ID NO 7
<211> LENGTH: 47
<212> TYPE: DNA
<213> ORGANISM: Artificial sequence
<220> FEATURE:
<223> OTHER INFORMATION: Synthetic nucleic acid sequence

<400> SEQUENCE: 7
acgagctgta caagtaaagc gaccctcgag tactaggatc cattagg                   47

<210> SEQ ID NO 8
<211> LENGTH: 43
<212> TYPE: DNA
<213> ORGANISM: Artificial sequence
<220> FEATURE:
<223> OTHER INFORMATION: Synthetic nucleic acid sequence

<400> SEQUENCE: 8
taagatctac agctcatgag agccatggct tcccgccggc ggt                       43

<210> SEQ ID NO 9
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 9
aaaagagacc atcaatgagg aagc                                            24

<210> SEQ ID NO 10
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 10
tggtgcaatc aggccctgc                                                  19

<210> SEQ ID NO 11
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 11
cagaatggga tagatgtgca tccagtgca                29

<210> SEQ ID NO 12
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 12
acagtcagac tcatcaagct ttctc                    25

<210> SEQ ID NO 13
<211> LENGTH: 16
<212> TYPE: DNA
<213> ORGANISM: Artificial sequence
<220> FEATURE:
<223> OTHER INFORMATION: Synthetic nucleic acid sequence

<400> SEQUENCE: 13
ctgtcgggtc ccctcg                              16

<210> SEQ ID NO 14
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 14
ttctctatca aagcaaccca tcctccca                 28

<210> SEQ ID NO 15
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 15
cggcgactgg aagaagcgga                          20

<210> SEQ ID NO 16
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 16
tactatgaga ccacacaact attgc                    25

<210> SEQ ID NO 17
<211> LENGTH: 31
<212> TYPE: DNA
<213> ORGANISM: Artificial sequence
<220> FEATURE:
<223> OTHER INFORMATION: Synthetic nucleic acid sequence

<400> SEQUENCE: 17
cgacgaagag ctcatcagaa cagtcagact c             31

<210> SEQ ID NO 18

<211> LENGTH: 236
<212> TYPE: PRT
<213> ORGANISM: Artificial sequence
<220> FEATURE:
<223> OTHER INFORMATION: Synthetic amino acid sequence

<400> SEQUENCE: 18

```
Met Val Ser Lys Gly Glu Glu Asn Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Ala Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Val Tyr Ile Lys His
65                  70                  75                  80

Pro Ala Asp Ile Pro Asp Tyr Phe Lys Leu Ser Phe Pro Glu Gly Phe
                85                  90                  95

Arg Trp Glu Arg Val Met Asn Phe Glu Asp Gly Gly Ile Ile His Val
            100                 105                 110

Asn Gln Asp Ser Ser Leu Gln Asp Gly Val Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Glu Glu Arg Met Tyr Pro Glu Asp Gly
145                 150                 155                 160

Ala Leu Lys Ser Glu Ile Lys Lys Arg Leu Lys Leu Lys Asp Gly Gly
                165                 170                 175

His Tyr Ala Ala Glu Val Lys Thr Thr Tyr Lys Ala Lys Lys Pro Val
            180                 185                 190

Gln Leu Pro Gly Ala Tyr Ile Val Asp Ile Lys Leu Asp Ile Val Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 19
<211> LENGTH: 711
<212> TYPE: DNA
<213> ORGANISM: Artificial sequence
<220> FEATURE:
<223> OTHER INFORMATION: Synthetic nucleic acid sequence

<400> SEQUENCE: 19

```
atggtgagca agggcgagga gaataacatg gccatcatca aggagttcat gcgcttcaag    60
gtgcacatgg agggctccgt gaacggccac gagttcgaga tcgagggcga gggcgagggc   120
cgcccctacg aggcctttca gaccgctaag ctgaaggtga ccaagggtgg ccccctgccc   180
ttcgcctggg acatcctgtc ccctcagttc atgtacggct ccaaggtcta cattaagcac   240
ccagccgaca tccccgacta cttcaagctg tccttccccg agggcttcag gtgggagcgc   300
gtgatgaact tcgaggacgg cggcattatt cacgttaacc aggactcctc cctgcaggac   360
ggcgtgttca tctacaaggt gaagctgcgc ggcaccaact tcccctccga cggccccgta   420
atgcagaaga agaccatggg ctgggaggcc tccgaggagc ggatgtaccc cgaggacggc   480
```

```
gccctgaaga gcagatcaa gaagaggctg aagctgaagg acggcggcca ctacgccgcc      540
gaggtcaaga ccacctacaa ggccaagaag cccgtgcagc tgcccggcgc ctacatcgtc      600
gacatcaagt tggacatcgt gtcccacaac gaggactaca ccatcgtgga acagtacgaa      660
cgcgccgagg ccgccactc caccggcggc atggacgagc tgtacaagta a                711
```

<210> SEQ ID NO 20
<211> LENGTH: 774
<212> TYPE: DNA
<213> ORGANISM: Artificial sequence
<220> FEATURE:
<223> OTHER INFORMATION: Synthetic nucleic acid sequence

<400> SEQUENCE: 20

```
tagagcggcc gccaccgcgg tggaagctat ccgccatcat ggggtctctc attatactcc       60
tactcctact aattctgctt atttggaccc tgtattctta atcaattagt tcaatttgtt      120
aaagacagga tctcagtagt ccaggcttta gtcctgactc aacaatacca ccagctaaaa      180
ccactagaat acgagccaca ataaataaaa gattttattt agtttccaga aaagggggg       240 aatgaaagac cccaccaaat tgcttagcct gatgccgctg taacgccatt ttgcaaggca      300
tggaaaaata ccaaaccaag aatagagaag ttcagatcaa gggcgggtac atgaaaatag      360
ctaacgttgg gccaaacagg atatctgcgg tgagcagttt cggccccggc ccggggccaa      420
gaacagatgg tcaccgcagt ttcggccccg gcccgaggcc aagaacagat ggtccccaga      480
tatggcccaa ccctcagcag tttcttaaga cccatcagat gtttccaggc tcccccaagg      540
acctgaaatg accctgcgcc ttatttgaat taaccaatca gcctgcttct cgcttctgtt      600
cgcgcgcttc tgcttcccga gctctataaa agagctcaca ccctcact cggcgcgcca      660 gtcctccgac agactgagtc gcccgggtac cgagctcgga tccactagtc cagtgtggtg      720
gaattctgca gatatccagc acagtggcgg ccgctcgaga tccaccggcc ggtc             774
```

<210> SEQ ID NO 21
<211> LENGTH: 239
<212> TYPE: PRT
<213> ORGANISM: Artificial sequence
<220> FEATURE:
<223> OTHER INFORMATION: Synthetic amino acid sequence

<400> SEQUENCE: 21

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
```

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 22
<211> LENGTH: 720
<212> TYPE: DNA
<213> ORGANISM: Artificial sequence
<220> FEATURE:
<223> OTHER INFORMATION: Synthetic nucleic acid sequence

<400> SEQUENCE: 22
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 23
<211> LENGTH: 13603
<212> TYPE: DNA
<213> ORGANISM: Artificial sequence
<220> FEATURE:
<223> OTHER INFORMATION: Synthetic nucleic acid sequence

<400> SEQUENCE: 23
tggaagggct agttcactcc cagaaaagac aagatatcct tgatctgtgg gtctaccaca      60
cacaaggctt cttcccagat tggcagaact acacaccagg gccaggaatc agatatccac     120
tgacctttgg atggtgctac aagctagtac cagttgagcc agatgaagga gagaacaaca     180
gagaggacaa cagcttgcta caccctgcta accagcatgg agtagaagac tcggagagac     240
aagtgttagt gtggaggttt gacagccgcc tagcattcca tcacgtggcc cgagagctgc     300
atccggagta cttcaagaac tgaactgctg acactgagct atctacaagg gactttccgc     360
tggggacttt ccaggaggtg tggcctgggc cgaactggg gagtggcgag ccctcagatg     420
ctgcatataa gcagctgctt tttgcctgta ctgggtctct ctggttagac cagatctgag     480

```
cctgggagct ctctggctag ctagggaacc cactgcttaa gcctcaataa agcttgcctt      540
gagtgcttca agtagtgtgt gcccgtctgt tgtgtgactc tggtagctag agatccctca      600
gaccatccta gttagtgtag aaaatctcta gcagtggcgc ccgaacaggg accggaaagc      660
gaaagagaaa ccagaggaga tctctcgacg caggactcgg cttgctgaag cgcgcacagc      720
aagaggcgag gggcggcgac tggtgagtac gccaaatttt ttgactagcg gaggctagaa      780
ggagagagat gggtgcgaga gcgtcagtat taagcggggg agaattagat agatgggaga      840
aaattcggtt aaggccaggg ggaaagaaaa aatataaact aaaacatata gtatgggcaa      900
gcagggagct agaacgattc gcagttaacc ctagcctgtt agaaacatca gagggctgta      960
gacaaatact gggacagcta caatcatccc ttcagacagg atcagaagaa cttaaatcat     1020
tatataatac agtagcaacc ctctattgtg tgcatcaaag gatagaggta aaagacacca     1080
aggaagcttt agataagata gaggaagagc aaaacaaaag taagaaaaag gcacagcaag     1140
cagcagctga cacaggaaat agcagccagg tcagccaaaa ttaccctata gtgcagaaca     1200
tccaggggca aatggtacat caggccatct cacctagaac tttaaatgca tgggtaaaag     1260
tagtagaaga gaaggctttc agcccagaag taatacccat gttttcagca ttatcagaag     1320
gagccacccc acaagattta aacaccatgc taaacacagt gggggacat caggcagcca      1380 tgcaaatgtt aaaagagacc atcaatgagg aagctgcaga atgggataga ttgcatccag     1440
tgcaggcagg gcctgttgca ccaggccaga tgagagaacc aaggggaagt gacatagcag     1500
gaactactag tacccttcag gaacaaatag gatggatgac aaataatcca cctatcccag     1560
taggagaaat ctataaaaga tggataatcc tgggattaaa taaaatagta agaatgtata     1620 gccccttccag catttggac ataaaacaag gaccaaagga accctttaga gactatgtag      1680
accggttcta taaaactcta agagccgagc aagcttcaca ggaggtaaaa aattggatga     1740
cagaaacctt gttggtccaa aatgcaaacc cagattgtaa aactatatta aaagcattgg     1800
gaccaggagc tacactagaa gaaatgatga cagcatgtca gggagtggga ggacccggac     1860
ataaagcaag agtcttggct gaggcaatga gccaagtaac aaattcagct accataatga     1920
tgcagagagg caattttaga aaccaaagaa agactgttaa gtgcttcaat tgtggcaaag     1980
aagggcacat agccaaaaat tgcagggccc ctaggaaaaa gggctgttgg aaatgtggaa     2040
aggaaggaca ccaaatgaaa gattgtactg agagacaggc taatttttta gggaaaatct     2100
ggccttccca aagggaagg ccagggaatt tcttcagag cagaccagag ccaacagccc      2160
caccagaaga gagcttcagg tttggggagg agacaacaac tccctctcag aagcaggagc     2220
cgatagacaa ggaactgtat cccttagctt ccctcagatc actctttggc aacgacccct     2280
cgtcacaata aaagtagggg ggcaactaaa ggaagctcta ttagatacag gagcagatga     2340
tacagtatta gaagacatga gtttgccagg aagatggaaa ccaaaaatga tagggggaat     2400
tggaggtttt atcaaagtaa gacagtatga gcagatagac atagaaatct gtggacataa     2460
agctaaaggt acagtattag taggacctac acctgtcaac ataattggaa gaaatctgtt     2520
gactcagatt ggttgcactt taaattttcc cattagtcct attgaaactg taccagtaaa     2580
attaaagcca ggaatggatg gtccaaaagt gaaacaatgg ccattgacag aagaaaaat      2640 aaaagcatta gtagaaattt gtacagaaat ggaaaaggaa ggaaaaattt caaaaattgg     2700
gcctgagaat ccatacaata ctccagtatt tgccataaag aaaaaagaca gtactaaatg     2760
gagaaaatta gtagatttca gagaacttaa taagagaacc caagacttct gggaagttca     2820
```

```
attaggcata ccacatcccg cagggttaaa aaagaaaaaa tcagtaacag tactggatgt      2880
gggtgatgca tattttttcag ttcccttaga tgaagacttc aggaagtaca ctgcatttac     2940 cataccctagt ataaacaatg agacaccagg gattagatat caatacaatg tgcttccaca    3000
gggatggaaa ggatcaccag caatattcca aagtagcatg acaaaaatct tagagccttt     3060
tagaaaacaa aatccagaca tagttatcta tcaatacatg gatgacttgt atgtaggatc    3120
tgacttagaa atagggcagc atagagcaaa aatagaggat ctgagacaac atctgttgaa     3180
gtgggggttt accacaccag acaaaaaaca tcagaaagaa cctccatttc tttggatggg     3240
ttatgaactc catcctgata aatggacagt acagcctata gtgctgccag aaaaagacag     3300
ctggactgtc aatgatatac agaagttagt ggggaaattg aattgggcaa gtcagattta     3360
tgcagggatt aaagtaaagc aattatgtaa actccttagg ggaaccaaag cactaacaga     3420
agtagtacca ctaacagaag aagcagagct agaactggca gaaaacaggg agattctaaa     3480
agaaccagta catggagtgt attatgaccc aacaaaagac ttaatagcag agctacagaa     3540
gcaggggcag ggccaatgga catatcaaat ttatcaggag ccatataaaa atctgaaaac     3600
aggaaaatat gcaagaatga gggggtgccca cactaatgat gtaaaacaat taacagaggc     3660
agtgcaaaaa atagccacag aaagcatagt aatatgggga aagactccta aatttaaact     3720
acccattcaa aaggaaacat gggaagcatg gtggacagat tattggcaag ccacctggat     3780
tcctgagtgg gagtttgtca ataccccctcc cttagtgaaa ttatggtatc agttagaaaa     3840
agaacccata gtaggagcag aaactttcta tgtagatgga gcagctaaca gggacaccaa     3900
atcaggaaaa gcaggatatg ttactgacag aggaagacaa aaagttgtct ccctagctga     3960
cacaacaaat cagaagactg agctacaagc aattcatcta gctttgcagg attcgggatt     4020
agaagtaaac atagtgacag actcacaata tgcattaggg atcattcaag cacagccaga     4080
taaaagtgaa tcagagttag tcagtcaaat aatagagcag ttaataaaaa aggaaaaggt     4140
ctacctggca tgggtaccag cacacaaagg aattggagga aatgaacaag tagataaatt     4200
agtcagtgct ggaatcagga aagtactatt tttagatgga atagataagg cccaagaaga     4260
acatgagaaa tatcacacta attggagagc aatggctagt gattttaacc tgccacctgt     4320
agtagcaaaa gaaatagtag ccagctgtaa taaatgtcag ctaaaaggag aagccatgca     4380
tggacaagta gactgtagtc caggaatatg gcaactagat tgcacacatt tagaaggaaa     4440
agttatcctg gtagcagttc atgtagccag tggatatata gaagcagaag ttattccagc     4500
agagacaggg caggaaacag catactttct cctaaaatta gcaggcagat ggccagtaaa     4560
aacaatacat acagacaatg gcagcaattt caccagtacc acagttaagg ccgcctgttg     4620
gtgggcaggg atcaagcagg aatttggcat tccctacaat ccccaaagtc aaggagtagt     4680
agaatctatg aataaagaat taagaaaat tataggacag gtaagagatc aggctgaaca     4740
tcttaagaca gcagtacaaa tggcagtatt catccacaat tttaaaagaa aggggggggat     4800 tgggggtac agtgcagggg aaagaatagt agacataata gcatcagaca tacaaactaa     4860
agaactacaa aaacaaatta caaaaattca aaattttcgg gtttattaca gggacagcag     4920
agatccactt tggaaaggac cagcaaagct tctctggaaa ggtgaagggg cagtagtaat     4980
acaggataat agtgacataa aagtagtgcc aagaagaaaa gcaaagatca ttagggatta     5040
tggaaaacag atggcaggtg atgattgtgt ggcaagtaga caggatgagg attagaacat     5100
ggaaaagttt agtaaaacac catatgtata tttcaggaaa agctaaggga tggtcttata     5160
gacatcacta tgaaagcact aatccaagaa taagttcaga agtacacatc ccactagggg     5220
```

```
atgctaaatt ggtagtaaca acatattggg gtctgcatac aggagaaaga gactggcatt    5280
tgggtcaggg agtctccata gaatggagga aaaagagata tagcacacaa gtagaccctg    5340
gcctagcaga ccgactaatt catctgtatt actttgattg ttttcagac tctgctataa    5400
gaaagtccat attaggacat atagttagcc ctagttgtga atatcaagca ggacataaca    5460
aggtaggatc tctacagtac ttggcactag cagcattaac aacaccaaga aggataaagc    5520
cacccttcc tagtgttacg aaactgacag aggatagatg gaacaagccc cagaagacca    5580
agggccacag agggagccat acaatgactg acactagag cttttagagg agcttaagaa    5640
tgaagctgtg agacatttcc ctaggatatg gctccatagt ttagggcaac atatctatga    5700
aacttatggg gatacttgga caggagtgga agccttaata agaattctgc aacaactgct    5760
gtttattcat tcagaattg ggtgtcgaca tagcagaata ggcattattc aacagaggag    5820
aacaagaaat ggagccagta atcctagcc tagagccctg gaagcatcca ggaagtcagc    5880
ctaaaactgc ttgtaccaat tgctattgca aaaaatgttg ctttcattgc caagcttgtt    5940
tcataacaaa aggcttaggc atctcctatg gcaggaagaa gcggagacag cgacgaagac    6000
ctcctcaaga cagtcagact catcaagttt ctctatcaaa gcagtaagta gtacatgtaa    6060
tgctttcttt acaaatatta gcaatagtag cattagtagt agcagcaata atagcaatag    6120
ttgtgtggtc tatagtattc atagaatata ggaaaatatt aagacaaaga aaaatagaca    6180
gattaattga tagaataaga gaaagagaag aagacagtgg caatgagagt gaaggagatc    6240
aggaagaatt ggcagcactt gagagggggc atcttgctcc ttgggatgtt gatgatctgt    6300
agtgctgcaa agaaaaaac gtgggtcaca atctattatg gggtacctgt gtggagagaa    6360
gcaaccacca ctctattttg tgcatcagat gctaaagcct atgatacaga ggtacataat    6420
gtttgggcca cacatgcctg tgtacccaca gaccccaacc cacaagaagt agtattggga    6480
aatgtgacag aaaattttaa catgtggaaa ataacatgg tagatcagat gcatgaggat    6540
ataatcagtt tatgggatga aagcctaaag ccatgtgtaa aattaacccc actctgtgtt    6600
actttaaatt gcactaattt gaatatcact aagaatacta ctaatcccac tagtagcagc    6660
tggggaatga tggagaaagg agaaataaaa aattgctctt tctatatcac cacaagcata    6720
agaaataagg taaagaaaga atatgcactt tttaatagac ttgatgtagt accaatagaa    6780
aatactaata atactaagta taggttaata agttgtaaca cctcagtcat tacacaggtc    6840
atcaaatatt acagggctgc tactaacaag agatggaggt aatagtactg agactgagac    6900
tgagatcttc agacctggag gaggagatat gagggacaat tggagaagtg aattatataa    6960
atataaagta gtaagaattg aaccaatagg agtagcaccc accagggcaa agagaagaac    7020
agtgcaaaga gaaaaagag cagtgggaat aggagctgtg ttccttgggt tcttgggagc    7080
agcaggaagc actatgggcg cagcgtcagt gacgctgacg gtacaggcca ggctattatt    7140
gtctggtata gtgcagcagc agaacaatct gctgagggct attgaggcgc aacagcatat    7200
gttgcaactc acagtctggg gcatcaagca gctccaggca agagtcctgg ctctggaaag    7260
atacctaagg gatcaacagc tcatgggaat ttggggttgc tctggaaaac tcatttgcac    7320
cacttctgtg ccttggaatg ttagttggag taataaatct gtggatgata tttgaataa    7380
catgacctgg atggagtggg aaagagaaat tgacaattac acagactata tatgactt    7440
acttgaaaaa tcgcaaaccc aacaagaaaa gaatgaaaaa gaattattgg aattggataa    7500
atgggcaagt ttgtggaatt ggtttgacat aacaaactgg ctgtggtata taagattatt    7560
```

-continued

```
cataatgata gtaggaggct tgataggttt aagaatagtt tttgctgtac tttctatagt    7620
aaatagagtt aggcagggat attcaccatt atcgtttcag accctcctcc cagcctcgag    7680
gggacccgac aggcccgaag gaacagaaga agaaggtgga gagagagaca gagacagatc    7740
cggtccatta gtgaacggat tcttggcact tttctgggtc gatttgagga acctgtgcct    7800
cttcctctac cacctcttga gaaacttact cttgattgta acgaggattg tggaacttct    7860
gggacgcagg gggtgggaag ccctcaaata ttggtggaat ctcctgcaat attggagcca    7920
ggaactaaag aatagtgctg ttagcttgct caacgccaca gccatagcag tagctgaggg    7980
gacagatagg gttataaaaa tagtacaaag agcttgtaga gctattcgca acatacctac    8040
aagaatcaga cagggcttgg aaagggcttt gctataagat ggtgagcaag ggcgaggaga    8100
ataacatggc catcatcaag gagttcatgc gcttcaaggt gcacatggag ggctccgtga    8160
acggccacga gttcgagatc gagggcgagg gcgagggccg cccctacgag gcctttcaga    8220
ccgctaagct gaaggtgacc aagggtggcc cctgccctt cgcctgggac atcctgtccc    8280
ctcagttcat gtacggctcc aaggtctaca ttaagcaccc agccgacatc cccgactact    8340
tcaagctgtc cttccccgag ggcttcaggt gggagcgcgt gatgaacttc gaggacggcg    8400
gcattattca cgttaaccag gactcctccc tgcaggacgg cgtgttcatc tacaaggtga    8460
agctgcgcgg caccaacttc ccctccgacg gccccgtaat gcagaagaag accatgggct    8520
gggaggcctc cgaggagcgg atgtaccccg aggacgcgc cctgaagagc gagatcaaga    8580
agaggctgaa gctgaaggac ggcggccact acgccgccga ggtcaagacc acctacaagg    8640
ccaagaagcc cgtgcagctg cccggcgcct acatcgtcga catcaagttg gacatcgtgt    8700
cccacaacga ggactacacc atcgtggaac agtacgaacg cgccgagggc cgccactcca    8760
ccggcggcat ggacgagctg tacaagtaac gatgtacggg ccagatatac gcggatccta    8820
gagcggccgc caccgcggtg gaagctatcc gccatcatgg ggtctctcat tatactccta    8880
ctcctactaa ttctgcttat ttggaccctg tattcttaat caattagttc aatttgttaa    8940
agacaggatc tcagtagtcc aggctttagt cctgactcaa caataccacc agctaaaacc    9000
actagaatac gagccacaat aaataaaaga tttatttag tttccagaaa aaggggggaa    9060
tgaaagaccc caccaaattg cttagcctga tgccgctgta acgccatttt gcaaggcatg    9120
gaaaaatacc aaaccaagaa tagagaagtt cagatcaagg gcgggtacat gaaaatagct    9180
aacgttgggc caaacaggat atctgcggtg agcagtttcg gccccggccc ggggccaaga    9240
acagatggtc accgcagttt cggccccggc ccgaggccaa gaacagatgg tccccagata    9300
tggcccaacc ctcagcagtt tcttaagacc catcagatgt ttccaggctc ccccaaggac    9360
ctgaaatgac cctgcgcctt atttgaatta accaatcagc ctgcttctcg cttctgttcg    9420
cgcgcttctg cttcccgagc tctataaaag agctcacaac ccctcactcg gcgcgccagt    9480
cctccgacag actgagtcgc ccgggtaccg agctcggatc cactagtcca gtgtggtgga    9540
attctgcaga tatccagcac agtggcggcc gctcgagatc caccggccgg tcgccaccat    9600
ggtgagcaag ggcgaggagc tgttcaccgg ggtggtgccc atcctggtcg agctggacgg    9660
cgacgtaaac ggccacaagt tcagcgtgtc cggcgagggc gagggcgatg ccacctacgg    9720
caagctgacc ctgaagttca tctgcaccac cggcaagctg cccgtgccct ggcccaccct    9780
cgtgaccacc ctgacctacg gcgtgcagtg cttcagccgc taccccgacc acatgaagca    9840
gcacgacttc ttcaagtccg ccatgcccga aggctacgtc caggagcgca ccatcttctt    9900
caaggacgac ggcaactaca agacccgcgc cgaggtgaag ttcgagggcg acaccctggt    9960
```

```
gaaccgcatc gagctgaagg gcatcgactt caaggaggac ggcaacatcc tggggcacaa      10020
gctggagtac aactacaaca gccacaacgt ctatatcatg gccgacaagc agaagaacgg      10080
catcaaggtg aacttcaaga tccgccacaa catcgaggac ggcagcgtgc agctcgccga      10140
ccactaccag cagaacaccc ccatcggcga cggccccgtg ctgctgcccg acaaccacta      10200
cctgagcacc cagtccgccc tgagcaaaga ccccaacgag aagcgcgatc acatggtcct      10260
gctggagttc gtgaccgccg ccgggatcac tctcggcatg gacgagctgt acaagtaaag      10320
cggccgcgac tctagagggc ccgtttaaac tcgagacctg gcgagacatg gagctatcac      10380
aagtagcaat actaacaatg ctgatattgc ctggctggaa gcacaagagg agggagaagt      10440
gggttttcca gtcagacctc aggtaccttt aagaccaatg acttacaagg cagctgtaga      10500
tcttagccac ttttttaaaag aaaaggggg actggaaggg ctagttcact cccgaaaaag      10560
acaagatatc cttgatctgt gggtctacca cacacaaggc ttcttcccag attggcagaa      10620
ctacacacca gggccaggaa tcagatatcc actgaccttt ggatggtgct acaagctagt      10680
accagttgag ccagatgaag gagagaacaa cagagaggac aacagcttgc tacaccctgc      10740
taaccagcat ggagtagaag actcggagag acaagtgtta gtgtggaggt ttgacagccg      10800
cctagcattc catcacgtgg cccgagagct gcatccggag tacttcaaga actgaactgc      10860
tgacactgag ctatctacaa gggactttcc gctgggact ttccagggag gtgtggcctg      10920
ggccgaactg gggagtggcg agccctcaga tgctgcatat aagcagctgc ttttttgcctg      10980 tactgggtct ctctggttag accagatctg agcctgggag ctctctggct agctagggaa      11040
cccactgctt aagcctcaat aaagcttgcc ttgagtgctt caagtagtgt gtgcccgtct      11100
gttgtgtgac tctggtagct agagatccct cagaccatcc tagttagtgt agaaaatctc      11160 tagcagggc gggatgcaag cttggcgtaa tcatggtcat agctgtttcc tgtgtgaaat      11220
tgttatccgc tcacaattcc acacaacata cgagccggaa gcataaagtg taaagcctgg      11280
ggtgcctaat gagtgagcta actcacatta attgcgttgc gctcactgcc cgctttccag      11340
tcgggaaacc tgtcgtgcca gctgcattaa tgaatcggcc aacgcgcggg gagaggcggt      11400
ttgcgtattg ggcgctcttc cgcttcctcg ctcactgact cgctgcgctc ggtcgttcgg      11460
ctgcggcgag cggtatcagc tcactcaaag gcggtaatac ggttatccac agaatcaggg      11520
gataacgcag gaaagaacat gtgagcaaaa ggccagcaaa aggccaggaa ccgtaaaaag      11580
gccgcgttgc tggcgttttt ccataggctc cgcccccctg acgagcatca caaaaatcga      11640
cgctcaagtc agaggtggcg aaacccgaca ggactataaa gataccaggc gtttccccct      11700
ggaagctccc tcgtgcgctc tcctgttccg accctgccgc ttaccggata cctgtccgcc      11760
tttctccctt cgggaagcgt ggcgctttct catagctcac gctgtaggta tctcagttcg      11820
gtgtaggtcg ttcgctccaa gctgggctgt gtgcacgaac ccccgttca gcccgaccgc      11880 tgcgccttat ccggtaacta tcgtcttgag tccaacccgg taagacacga cttatcgcca      11940
ctggcagcag ccactggtaa caggattagc agagcgaggt atgtaggcgg tgctacagag      12000
ttcttgaagt ggtggcctaa ctacggctac actagaagaa cagtatttgg tatctgcgct      12060
ctgctgaagc cagttacctt cggaaaaaga gttggtagct cttgatccgg caaacaaacc      12120
accgctggta gcggtggttt ttttgtttgc aagcagcaga ttacgcgcag aaaaaaagga      12180
tctcaagaag atcctttgat cttttctacg gggtctgacg ctcagtggaa cgaaaactca      12240
cgttaaggga ttttggtcat gagattatca aaaaggatct tcacctagat ccttttaaat      12300
```

```
taaaaatgaa gttttaaatc aatctaaagt atatatgagt aaacttggtc tgacagttac    12360
caatgcttaa tcagtgaggc acctatctca gcgatctgtc tatttcgttc atccatagtt    12420
gcctgactcc ccgtcgtgta gataactacg atacgggagg gcttaccatc tggcccagt     12480 gctgcaatga taccgcgaga cccacgctca ccggctccag atttatcagc aataaaccag    12540
ccagccggaa gggccgagcg cagaagtggt cctgcaactt tatccgcctc catccagtct    12600
attaattgtt gccgggaagc tagagtaagt agttcgccag ttaatagttt gcgcaacgtt    12660
gttgccattg ctacaggcat cgtggtgtca cgctcgtcgt ttggtatggc ttcattcagc    12720
tccggttccc aacgatcaag gcgagttaca tgatccccca tgttgtgcaa aaaagcggtt    12780
agctccttcg gtcctccgat cgttgtcaga agtaagttgg ccgcagtgtt atcactcatg    12840
gttatggcag cactgcataa ttctcttact gtcatgccat ccgtaagatg cttttctgtg    12900
actggtgagt actcaaccaa gtcattctga gaatagtgta tgcggcgacc gagttgctct    12960
tgcccggcgt caatacggga taataccgcg ccacatagca gaactttaaa agtgctcatc    13020
attggaaaac gttcttcggg gcgaaaactc tcaaggatct taccgctgtt gagatccagt    13080
tcgatgtaac ccactcgtgc acccaactga tcttcagcat cttttacttt caccagcgtt    13140
tctgggtgag caaaaacagg aaggcaaaat gccgcaaaaa agggaataag ggcgacacgg    13200
aaatgttgaa tactcatact cttcctttt caatattatt gaagcattta tcagggttat    13260
tgtctcatga gcggatacat atttgaatgt atttagaaaa ataaacaaat aggggttccg    13320
cgcacatttc cccgaaaagt gccacctgac gtctaagaaa ccattattat catgacatta    13380
acctataaaa ataggcgtat cacgaggccc tttcgtctcg cgcgtttcgg tgatgacggt    13440
gaaaacctct gacacatgca gctcccggag acggtcacag cttgtctgta agcggatgcc    13500
gggagcagac aagcccgtca gggcgcgtca gcgggtgttg gcgggtgtcg ggctggcac    13560 catattaact atgcggcatc agagcagatt gtactgagag tgc    13603
```

<210> SEQ ID NO 24
<211> LENGTH: 239
<212> TYPE: PRT
<213> ORGANISM: Artificial sequence
<220> FEATURE:
<223> OTHER INFORMATION: Synthetic amino acid sequence

<400> SEQUENCE: 24

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly His Ile Leu Gly His Lys Leu Glu Tyr
```

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 25
<211> LENGTH: 720
<212> TYPE: DNA
<213> ORGANISM: Artificial sequence
<220> FEATURE:
<223> OTHER INFORMATION: Synthetic nucleic acid sequence

<400> SEQUENCE: 25
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggccacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 26
<211> LENGTH: 585
<212> TYPE: DNA
<213> ORGANISM: Artificial sequence
<220> FEATURE:
<223> OTHER INFORMATION: Synthetic nucleic acid sequence

<400> SEQUENCE: 26
gtactaggat ccattaggcg gccgcggatc tgcgatcgct ccggtgcccg tcagtgggca      60
gagcgcacat cgcccacagt ccccgagaag ttgggggggag gggtcggcaa ttgaaccggt    120
gcctagagaa ggtggcgcgg ggtaaactgg aaagtgatg tcgtgtactg ctccgcctt      180 tttcccgagg gtgggggaga accgtatata agtgcagtag tcgccgtgaa cgttctttt     240 cgcaacgggt ttgccgccag aacacagctg aagcttcgag gggctcgcat ctctccttca    300
cgcgcccgcc gccctacctg aggccgccat ccacgccggt tgagtcgcgt tctgccgcct    360
cccgcctgtg gtgcctcctg aactgcgtcc gccgtctagg taagtttaaa gctcaggtcg    420
agaccgggcc tttgtccggc gctcccttgg agcctaccta gactcagccg gctctccacg    480

-continued

```
ctttgcctga ccctgcttgc tcaactctac gtctttgttt cgttttctgt tctgcgccgt      540
tacagatcca agctgtgacc ggcgcctacg ctagcgctac cggtc                      585
```

<210> SEQ ID NO 27
<211> LENGTH: 236
<212> TYPE: PRT
<213> ORGANISM: Artificial sequence
<220> FEATURE:
<223> OTHER INFORMATION: Synthetic amino acid sequence

<400> SEQUENCE: 27

```
Met Val Ser Lys Gly Glu Glu Asp Asn Met Ala Ile Ile Lys Glu Phe
1               5                   10                  15
Met Arg Phe Lys Val His Met Glu Gly Ser Val Asn Gly His Glu Phe
                20                  25                  30
Glu Ile Glu Gly Glu Gly Glu Gly Arg Pro Tyr Glu Gly Thr Gln Thr
            35                  40                  45
Ala Lys Leu Lys Val Thr Lys Gly Gly Pro Leu Pro Phe Ala Trp Asp
        50                  55                  60
Ile Leu Ser Pro Gln Phe Met Tyr Gly Ser Lys Ala Tyr Val Lys His
65                  70                  75                  80
Pro Ala Asp Ile Pro Asp Tyr Leu Lys Leu Ser Phe Pro Glu Gly Phe
                85                  90                  95
Lys Trp Glu Arg Val Met Asn Phe Glu Asp Gly Gly Val Val Thr Val
                100                 105                 110
Thr Gln Asp Ser Ser Leu Gln Asp Gly Glu Phe Ile Tyr Lys Val Lys
            115                 120                 125
Leu Arg Gly Thr Asn Phe Pro Ser Asp Gly Pro Val Met Gln Lys Lys
        130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
            180                 185                 190
Gln Leu Pro Gly Ala Tyr Asn Val Asn Ile Lys Leu Asp Ile Thr Ser
        195                 200                 205
His Asn Glu Asp Tyr Thr Ile Val Glu Gln Tyr Glu Arg Ala Glu Gly
    210                 215                 220
Arg His Ser Thr Gly Gly Met Asp Glu Leu Tyr Lys
225                 230                 235
```

<210> SEQ ID NO 28
<211> LENGTH: 711
<212> TYPE: DNA
<213> ORGANISM: Artificial sequence
<220> FEATURE:
<223> OTHER INFORMATION: Synthetic nucleic acid sequence

<400> SEQUENCE: 28

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
```

```
gtgatgaact tcgaggacgg cggcgtggtg accgtgaccc aggactcctc cctgcaggac      360
ggcgagttca tctacaaggt gaagctgcgc ggcaccaact tccctccga cggccccgta       420 atgcagaaga agaccatggg ctgggaggcc tcctccgagc ggatgtaccc cgaggacggc      480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa     660
cgcgccgagg gccgccactc caccggcggc atggacgagc tgtacaagta a              711
```

```
<210> SEQ ID NO 29
<211> LENGTH: 10975
<212> TYPE: DNA
<213> ORGANISM: Artificial sequence
<220> FEATURE:
<223> OTHER INFORMATION: Synthetic nucleic acid sequence

<400> SEQUENCE: 29
```

```
ggtctctctg ttagaccag atctgagcct gggagctctc tggctaacta gggaacccac       60
tgcttaagcc tcaataaagc ttgccttgag tgcttcaagt agtgtgtgcc cgtctgttgt     120
gtgactctgg taactagaga tccctcagac ccttttagtc agtgtggaaa atctctagca    180
gtggcgcccg aacagggacc tgaaagcgaa agggaaacca gaggagctct ctcgacgcag   240
gactcggctt gctgaagcgc gcacggcaag aggcgagggg cggcgactgg tgagtacgcc    300
aaaaattttg actagcggag gctagaagga gagagatggg tgcgagagcg tcagtattaa    360
gcgggggaga attagatcga tgggaaaaaa ttcggttaag gccagggga aagaaaaaat     420 ataaattaaa acatatagta tgggcaagca gggagctaga acgattcgca gttaatcctg   480
gcctgttaga acatcagaa ggctgtagac aaatactggg acagctacaa ccatcccttc     540
agacaggatc agaagaactt agatcattat ataatacagt agcaaccctc tattgtgtgc    600
atcaaaggat agagataaaa gacaccaagg aagctttaga caagatagag gaagagcaaa    660
acaaaagtaa gaaaaaagca cagcaagcag cagctgacac aggacacagc aatcaggtca    720
gccaaaatta ccctatagtg cagaacatcc aggggcaaat ggtacatcag gccatatcac   780
ctagaacttt aaatgcatgg gtaaaagtag tagaagagaa ggctttcagc ccagaagtga    840
tacccatgtt ttcagcatta tcagaaggag ccaccccaca gatttaaaac accatgctaa    900
acacagtggg gggacatcaa gcagccatgc aaatgttaaa agagaccatc aatgaggaag    960
ctgcagaatg gatagagtg catccagtgc atgcagggcc tattgcacca ggccagatga    1020
gagaaccaag gggaagtgac atagcaggaa ctactagtac ccttcaggaa caaataggat   1080
ggatgacaaa taatccacct atcccagtag gagaaattta taaagatgg ataatcctgg    1140 gattaaataa aatagtaaga atgtatagcc ctaccagcat tctggacata agacaaggac    1200
caaaggaacc ctttagagac tatgtagacc ggttctataa aactctaaga gccgagcaag    1260
cttcacagga ggtaaaaaat tggatgacag aaaccttgtt ggtccaaaat gcgaacccag    1320
attgtaagac tattttaaaa gcattgggac cagcggctac actagaagaa atgatgacag    1380
catgtcaggg agtaggagga cccggccata aggcaagagt tttggctgaa gcaatgagcc    1440
aagtaacaaa ttcagctacc ataatgatgc agagaggcaa ttttaggaac caaagaaaga    1500
ttgttaagtg tttcaattgt ggcaaagaag ggcacacagc cagaaattgc agggccccta   1560
ggaaaaaggg ctgttggaaa tgtggaaagg aaggacacca aatgaaagat tgtactgaga    1620
```

```
gacaggctaa ttttttaggg aagatctggc cttcctacaa gggaaggcca gggaattttc    1680
ttcagagcag accagagcca acagccccac cagaagagag cttcaggtct ggggtagaga    1740
caacaactcc ccctcagaag caggagccga tagacaagga actgtatcct ttaacttccc    1800
tcaggtcact ctttggcaac gacccctcgt cacaataaag atagggggc aactaaagga     1860
agctctatta gatacaggag cagatgatac agtattagaa gaaatgagtt tgccaggaag    1920
atggaaacca aaaatgatag ggggaattgg aggttttatc aaagtaagac agtatgatca    1980
gatactcata gaaatctgtg gacataaagc tataggtaca gtattagtag gacctacacc    2040
tgtcaacata attggaagaa atctgttgac tcagattggt tgcactttaa attttcccat    2100
tagccctatt gagactgtac cagtaaaatt aaagccagga atggatggcc caaaagttaa    2160
acaatggcca ttgacagaag aaaaaataaa agcattagta gaaatttgta cagagatgga    2220
aaaggaaggg aaaatttcaa aaattgggcc tgaaaatcca tacaatactc cagtatttgc    2280
cataaagaaa aaagacagta ctaaatggag aaaattagta gatttcagag aacttaataa    2340
gagaactcaa gacttctggg aagttcaatt aggaatacca catcccgcag ggttaaaaaa    2400
gaaaaaatca gtaacagtac tggatgtggg tgatgcatat ttttcagttc ccttagatga    2460
agacttcagg aagtatactg catttaccat acctagtata aacaatgaga caccagggat    2520
tagatatcag tacaatgtgc ttccacaggg atggaaagga tcaccagcaa tattccaaag    2580
tagcatgaca aaaatcttag agccttttag aaaacaaaat ccagacatag ttatctatca    2640
atacatggat gatttgtatg taggatctga cttagaaata gggcagcata gaacaaaaat    2700
agaggagctg agacaacatc tgttgaggtg gggacttacc acaccagaca aaaaacatca    2760
gaaagaacct ccattccttt ggatgggtta tgaactccat cctgataaat ggacagtaca    2820
gcctatagtg ctgccagaaa aagacagctg gactgtcaat gacatacaga agttagtggg    2880
gaaattgaat tgggcaagtc agatttaccc agggattaaa gtaaggcaat tatgtaaact    2940
ccttagagga accaaagcac taacagaagt aataccacta acagaagaag cagagctaga    3000
actggcagaa aacagagaga ttctaaaaga accagtacat ggagtgtatt atgacccatc    3060
aaaagactta atagcagaaa tacagaagca ggggcaaggc caatggacat atcaaattta    3120
tcaagagcca tttaaaaatc tgaaaacagg aaaatatgca agaatgaggg gtgcccacac    3180
taatgatgta aaacaattaa cagaggcagt gcaaaaaata accacagaaa gcatagtaat    3240
atggggaaag actcctaaat ttaaactgcc catacaaaag gaaacatggg aaacatggtg    3300
gacagagtat tggcaagcca cctggattcc tgagtgggag tttgttaata cccctccctt    3360
agtgaaatta tggtaccagt tagagaaaga acccatagta ggagcagaaa ccttctatgt    3420
agatggggca gctaacaggg agactaaatt aggaaaagca ggatatgtta ctaatagagg    3480
aagacaaaaa gttgtcaccc taactgacac aacaaatcag aagactgagt tacaagcaat    3540
ttatctagct ttgcaggatt cgggattaga agtaaacata gtaacagact cacaatatgc    3600
attaggaatc attcaagcac aaccagatca aagtgaatca gagttagtca atcaaataat    3660
agagcagtta ataaaaaagg aaaaggtcta tctggcatgg gtaccagcac acaaaggaat    3720
tggaggaaat gaacaagtag ataaattagt cagtgctgga atcaggaaag tactattttt    3780
agatggaata gataaggccc aagatgaaca tgagaaatat cacagtaatt ggagagcaat    3840
ggctagtgat tttaacctgc cacctgtagt agcaaaagaa atagtagcca gctgtgataa    3900
atgtcagcta aaaggagaag ccatgcatgg acaagtagac tgtagtccag gaatatggca    3960
actagattgt acacatttag aaggaaaagt tatcctggta gcagttcatg tagccagtgg    4020
```

```
atatatagaa gcagaagtta ttccagcaga aacagggcag gaaacagcat attttctttt    4080
aaaattagca ggaagatggc cagtaaaaac aatacatact gacaatggca gcaatttcac    4140
cggtgctacg gttagggccg cctgttggtg ggcgggaatc aagcaggaat ttggaattcc    4200
ctacaatccc caaagtcaag gagtagtaga atctatgaat aaagaattaa agaaaattat    4260
aggacaggta agagatcagg ctgaacatct taagacagca gtacaaatgg cagtattcat    4320
ccacaatttt aaaagaaaag ggggattggg gggtacagt gcaggggaaa gaatagtaga    4380
cataatagca acagacatac aaactaaaga attacaaaaa caaattacaa aaattcaaaa    4440
ttttcgggtt tattacaggg acagcagaaa tccactttgg aaaggaccag caaagctcct    4500
ctggaaaggt gaaggggcag tagtaataca agataatagt gacataaaag tagtgccaag    4560
aagaaaagca aagatcatta gggattatgg aaaacagatg gcaggtgatg attgtgtggc    4620
aagtagacag gatgaggatt agaacatgga aaagtttagt aaaacaccat atgtatgttt    4680
cagggaaagc tagggatgg ttttatagac atcactatga aagccctcat ccaagaataa    4740
gttcagaagt acacatccca ctaggggatg ctagattggt aataacaaca tattggggtc    4800
tgcatacagg agaaagagac tggcatttgg gtcagggagt ctccatagaa tggaggaaaa    4860
agagatatag cacacaagta gaccctgaac tagcagacca actaattcat ctgtattact    4920
ttgactgttt ttcagactct gctataagaa aggccttatt aggacacata gttagcccta    4980
ggtgtgaata tcaagcagga cataacaagg taggatctct acaatacttg gcactagcag    5040
cattaataac accaaaaaag ataaagccac ctttgcctag tgttacgaaa ctgacagagg    5100
atagatggaa caagccccag aagaccaagg gccacagagg gagccacaca atgaatggac    5160
actagagctt ttagaggagc ttaagaatga agctgttaga catttttccta ggatttggct    5220 ccatggctta gggcaacata tctatgaaac ttatggggat acttgggcag gagtggaagc    5280
cataataaga attctgcaac aactgctgtt tatccatttt cagaattggg tgtcgacata    5340
gcagaatagg cgttactcga cagaggagag caagaaatgg agccagtaga tcctagacta    5400
gagccctgga agcatccagg aagtcagcct aaaactgctt gtaccaattg ctattgtaaa    5460
aagtgttgct ttcattgcca gtttgtttc ataacaaaag ccttaggcat ctcctatggc    5520
aggaagaagc ggagacagcg acgaagagct catcagaaca gtcagactca tcaagcttct    5580
ctatcaaagc agtaagtagt acatgtaatg caacctatac caatagtagc aatagtagca    5640
ttagtagtag caataataat agcaatagtt gtgtggtcca tagtaatcat agaatatagg    5700
aaaatattaa gacaaagaaa aatagacagg ttaattgata gactaataga aagagcagaa    5760
gacagtggca atgagagtga aggagaaata tcagcacttg tggagatggg ggtggagatg    5820
gggcaccatg ctccttggga tgttgatgat ctgtagtgct acagaaaaat tgtgggtcac    5880
agtctattat ggggtacctg tgtggaagga agcaaccacc actctatttt gtgcatcaga    5940
tgctaaagca tatgatacag aggtacataa tgtttgggcc acacatgcct gtgtacccac    6000
agaccccaac ccacaagaag tagtattggt aaatgtgaca gaaaatttta acatgtggaa    6060
aaatgacatg gtagaacaga tgcatgagga tataatcagt ttatgggatc aaagcctaaa    6120
gccatgtgta aaattaaccc cactctgtgt tagtttaaag tgcactgatt tgaagaatga    6180
tactaatacc aatagtagta gcgggagaat gataatggag aaaggagaga taaaaaactg    6240
ctctttcaat atcagcacaa gcataagagg taaggtgcag aaagaatatg cattttttta    6300
taaacttgat ataataccaa tagataatga tactaccagc tataagttga caagttgtaa    6360
```

```
cacctcagtc attacacagg gcctgtccaa aggtatcctt tgagccaatt cccatacatt    6420
attgtgcccc ggctggtttt gcgattctaa aatgtaataa taagacgttc aatggaacag    6480
gaccatgtac aaatgtcagc acagtacaat gacacatgga attaggccag tagtatcaac    6540
tcaactgctg ttaaatggca gtctagcaga agaagaggta gtaattagat ctgtcaattt    6600
cacggacaat gctaaaacca taatagtaca gctgaacaca tctgtagaaa ttaattgtac    6660
aagacccaac aacaatacaa gaaaaagaat ccgtatccag agaggaccag ggagagcatt    6720
tgttacaata ggaaaaatag gaaatatgag acaagcacat tgtaacatta gtagagcaaa    6780
atggaataac actttaaaac agatagctag caaattaaga gaacaatttg gaaataataa    6840
aacaataatc tttaagcaat cctcaggagg ggacccagaa attgtaacgc acagttttaa    6900
ttgtggaggg gaattttcct actgtaattc aacacaactg tttaatagta cttggtttaa    6960
tagtacttgg agtactgaag ggtcaaataa cactgaagga agtgacacaa tcaccctccc    7020
atgcagaata aaacaaatta taaacatgtg gcagaaagta ggaaaagcaa tgtatgcccc    7080
tcccatcagt ggacaaatta gatgttcatc aaatattaca gggctgctat taacaagaga    7140
tggtggtaat agcaacaatg agtccgagat cttcagacct ggaggaggag atatgaggga    7200
caattggaga agtgaattat ataaatataa agtagtaaaa attgaaccat taggagtagc    7260
acccaccaag gcaaagagaa gagtggtgca gagagaaaaa agagcagtgg aataggagc     7320
tttgttcctt gggttcttgg gagcagcagg aagcactatg ggcgcagcct caatgacgct    7380
gacggtacag gccagacaat tattgtctgg tatagtgcag cagcagaaca atttgctgag    7440
ggctattgag gcgcaacagc atctgttgca actcacagtc tggggcatca agcagctcca    7500
ggcaagaatc ctggctgtgg aaagatacct aaaggatcaa cagctcctgg ggatttgggg    7560
ttgctctgga aaactcattt gcaccactgc tgtgccttgg aatgctagtt ggagtaataa    7620
atctctggaa cagatttgga atcacacgac ctggatggag tgggacagag aaattaacaa    7680
ttacacaagc ttaatacact ccttaattga agaatcgcaa aaccagcaag aaaagaatga    7740
acaagaatta ttggaattag ataaatgggc aagtttgtgg aattggttta acataacaaa    7800
ttggctgtgg tatataaaat tattcataat gatagtagga ggcttggtag gtttaagaat    7860
agtttttgct gtactttcta tagtgaatag agttaggcag ggatattcac cattatcgtt    7920
tcagacccac ctcccaaccc cgaggggacc cgacaggccc gaaggaatag aagaagaagg    7980
tggagagaga gacagagaca gatccattcg attagtgaac ggatccttgg cacttatctg    8040
ggacgatctg cggagcctgt gcctcttcag ctaccaccgc ttgagagact tactcttgat    8100
tgtaacgagg attgtggaac ttctgggacg caggggtgg gaagccctca aatattggtg    8160
gaatctccta cagtattgga gtcaggaact aaagaatagt gctgttagct tgctcaatgc    8220
cacagccata gcagtagctg aggggacaga taggttata gaagtagtac aaggagcttg    8280
tagagctatt cgccacatac ctagaagaat aagacagggc ttggaaagga ttttgctata    8340
agcatggtga gcaagggcga ggagctgttc accggggtgg tgcccatcct ggtcgagctg    8400
gacggcgacg taaacggcca caagttcagc gtgtccggcg agggcgaggg cgatgccacc    8460
tacggcaagc tgaccctgaa gttcatctgc accaccggca agctgcccgt gccctggccc    8520
accctcgtga ccaccctgac ctacggcgtg cagtgcttca gccgctaccc cgaccacatg    8580
aagcagcacg acttcttcaa gtccgccatg cccgaaggct acgtccagga gcgcaccatc    8640
ttcttcaagg acgacggcaa ctacaagacc cgcgccgagg tgaagttcga gggcgacacc    8700
ctggtgaacc gcatcgagct gaagggcatc gacttcaagg aggacggcca catcctgggg    8760
```

-continued

```
cacaagctgg agtacaacta caacagccac aacgtctata tcatggccga caagcagaag    8820
aacggcatca aggtgaactt caagatccgc cacaacatcg aggacggcag cgtgcagctc    8880
gccgaccact accagcagaa cacccccatc ggcgacggcc ccgtgctgct gcccgacaac    8940
cactacctga gcacccagtc cgccctgagc aaagacccca acgagaagcg cgatcacatg    9000
gtcctgctgg agttcgtgac cgccgccggg atcactctcg gcatggacga gctgtacaag    9060
taaagcgacc ctcgagtact aggatccatt aggcggccgc ggatctgcga tcgctccggt    9120
gcccgtcagt gggcagagcg cacatcgccc acagtccccg agaagttggg gggagggggtc   9180
ggcaattgaa ccggtgccta gagaaggtgg cgcggggtaa actgggaaag tgatgtcgtg    9240
tactggctcc gccttttttcc cgagggtggg ggagaaccgt atataagtgc agtagtcgcc   9300
gtgaacgttc tttttcgcaa cgggtttgcc gccagaacac agctgaagct cgagggggct    9360
cgcatctctc cttcacgcgc ccgccgccct acctgaggcc gccatccacg ccggttgagt    9420
cgcgttctgc cgcctcccgc ctgtggtgcc tcctgaactg cgtccgccgt ctaggtaagt    9480
ttaaagctca ggtcgagacc gggcctttgt ccggcgctcc cttggagcct acctagactc    9540
agccggctct ccacgctttg cctgaccctg cttgctcaac tctacgtctt tgtttcgttt    9600
tctgttctgc gccgttacag atccaagctg tgaccggcgc ctacgctagc gctaccggtc    9660
gccaccatgg tgagcaaggg cgaggaggat aacatggcca tcatcaagga gttcatgcgc    9720
ttcaaggtgc acatggaggg ctccgtgaac ggccacgagt tcgagatcga gggcgagggc    9780
gagggccgcc cctacgaggg cacccagacc gccaagctga aggtgaccaa gggtggcccc    9840
ctgcccttcg cctgggacat cctgtcccct cagttcatgt acggctccaa ggcctacgtg    9900
aagcaccccg ccgacatccc cgactacttg aagctgtcct tccccgaggg cttcaagtgg    9960
gagcgcgtga tgaacttcga ggacggcggc gtggtgaccg tgacccagga ctcctccctg   10020
caggacggcg agttcatcta caaggtgaag ctgcgcggca ccaacttccc ctccgacggc   10080
cccgtaatgc agaagaagac catgggctgg gaggcctcct ccgagcggat gtaccccgag   10140
gacggcgccc tgaagggcga gatcaagcag aggctgaagc tgaaggacgg cggccactac   10200
gacgctgagg tcaagaccac ctacaaggcc aagaagcccg tgcagctgcc cggcgcctac   10260
aacgtcaaca tcaagttgga catcacctcc cacaacgagg actacaccat cgtggaacag   10320
tacgaacgcg ccgagggccg ccactccacc ggcggcatgg acgagctgta caagtaactc   10380
atgagctgta gatcttagcc actttttttaa aagaaaaggg gggactggaa gggctaattc   10440
actcccaaag aagacaagat atccttgatc tgtggatcta ccacacacaa ggctacttcc   10500
ctgattagca gaactacaca ccagggccag ggtcagata tccactgacc tttggatggt   10560
gctacaagct agtaccagtt gagccagata agatagaaga ggccaataaa ggagagaaca   10620
ccagcttgtt acaccctgtg agcctgcatg ggatggatga cccggagaga gaagtgttag   10680
agtggaggtt tgacagccgc ctagcatttc atcacgtggc ccgagagctg catccggagt   10740
acttcaagaa ctgctgacat cgagcttgct acaagggact ttccgctggg acttttccag   10800
ggaggcgtgg cctgggcggg actggggagt ggcgagccct cagatcctgc atataagcag   10860
ctgcttttttg cctgtactgg gtctctctgg ttagaccaga tctgagcctg ggagctctct   10920
ggctaactag ggaacccact gcttaagcct caataaagct tgccttgagt gcttc         10975
```

<210> SEQ ID NO 30
<211> LENGTH: 15
<212> TYPE: DNA

```
<213> ORGANISM: Artificial sequence
<220> FEATURE:
<223> OTHER INFORMATION: Synthetic nucleic acid sequence

<400> SEQUENCE: 30
ctataagatg ggagg                                                      15

<210> SEQ ID NO 31
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 31
ctataagatg gtgag                                                      15

<210> SEQ ID NO 32
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 32
ctataagatg ggtgg                                                      15

<210> SEQ ID NO 33
<211> LENGTH: 16
<212> TYPE: DNA
<213> ORGANISM: Artificial sequence
<220> FEATURE:
<223> OTHER INFORMATION: Synthetic nucleic acid sequence

<400> SEQUENCE: 33
ctataagcat ggtgag                                                     16

<210> SEQ ID NO 34
<211> LENGTH: 12
<212> TYPE: DNA
<213> ORGANISM: Artificial sequence
<220> FEATURE:
<223> OTHER INFORMATION: Synthetic nucleic acid sequence

<400> SEQUENCE: 34
gccaccatgg tg                                                         12

<210> SEQ ID NO 35
<211> LENGTH: 12
<212> TYPE: DNA
<213> ORGANISM: Artificial sequence
<220> FEATURE:
<223> OTHER INFORMATION: Synthetic nucleic acid sequence

<400> SEQUENCE: 35
aagtaaagcg gc                                                         12

<210> SEQ ID NO 36
<211> LENGTH: 12
<212> TYPE: DNA
<213> ORGANISM: Artificial sequence
<220> FEATURE:
<223> OTHER INFORMATION: Synthetic nucleic acid sequence

<400> SEQUENCE: 36
agcgaccctc ga                                                         12
```

<210> SEQ ID NO 37
<211> LENGTH: 12
<212> TYPE: DNA
<213> ORGANISM: Artificial sequence
<220> FEATURE:
<223> OTHER INFORMATION: Synthetic nucleic acid sequence

<400> SEQUENCE: 37
gccaccatgg tg                                                          12

<210> SEQ ID NO 38
<211> LENGTH: 12
<212> TYPE: DNA
<213> ORGANISM: Artificial sequence
<220> FEATURE:
<223> OTHER INFORMATION: Synthetic nucleic acid sequence

<400> SEQUENCE: 38
aagtaactca tg                                                          12

<210> SEQ ID NO 39
<211> LENGTH: 1211
<212> TYPE: DNA
<213> ORGANISM: Artificial Sequence
<220> FEATURE:
<223> OTHER INFORMATION: Synthetic nucleic acid sequence

<400> SEQUENCE: 39

```
ggcctccgcg ccgggttttg gcgcctcccg cgggcgcccc cctcctcacg gcgagcgctg      60
ccacgtcaga cgaagggcgc aggagcgtcc tgatccttcc gcccggacgc tcaggacagc     120
ggcccgctgc tcataagact cggccttaga accccagtat cagcagaagg acattttagg     180
acgggacttg ggtgactcta gggcactggt tttctttcca gagagcggaa caggcgagga     240
aaagtagtcc cttctcggcg attctgcgga gggatctccg tggggcggtg aacgccgatg     300
attatataag gacgcgccgg gtgtggcaca gctagttccg tcgcagccgg gatttgggtc     360
gcggttcttg tttgtggatc gctgtgatcg tcacttggtg agtagcgggc tgctgggctg     420 gccgggggctt tcgtggccgc cgggccgctc ggtgggacgg aagcgtgtgg agagaccgcc     480
aagggctgta gtctgggtcc gcgagcaagg ttgccctgaa ctgggggttg ggggagcgc      540 agcaaaatgg cggctgttcc cgagtcttga atggaagacg cttgtgaggc gggctgtgag     600
gtcgttgaaa caaggtgggg ggcatggtgg gcggcaagaa cccaaggtct tgaggccttc     660
gctaatgcgg gaaagctctt attcgggtga gatgggctgg ggcaccatct ggggaccctg     720
acgtgaagtt tgtcactgac tggagaactc ggtttgtcgt ctgttgcggg ggcggcagtt     780
atgcggtgcc gttgggcagt gcacccgtac ctttgggagc gcgcgccctc gtcgtgtcgt     840
gacgtcaccc gttctgttgg cttataatgc agggtggggc cacctgccgg taggtgtgcg     900
gtaggctttt ctccgtcgca ggacgcaggg ttcgggccta gggtaggctc tcctgaatcg     960
acaggcgccg gacctctggt gaggggaggg ataagtgagg cgtcagtttc tttggtcggt    1020
tttatgtacc tatcttctta agtagctgaa gctccggttt tgaactatgc gctcggggtt    1080
ggcgagtgtg ttttgtgaag ttttttaggc acctttgaa atgtaatcat ttgggtcaat    1140
atgtaatttt cagtgttaga ctagtaaatt gtccgctaaa ttctggccgt ttttggcttt    1200
tttgttagac g                                                         1211
```

<210> SEQ ID NO 40

<211> LENGTH: 664
<212> TYPE: DNA
<213> ORGANISM: Artificial Sequence
<220> FEATURE:
<223> OTHER INFORMATION: Synthetic nucleic acid sequence

<400> SEQUENCE: 40

| tatccgccat catggggtct ctcattatac tcctactcct actaattctg cttatttgga | 60 |
| ccctgtattc ttaatcaatt agttcaattt gttaaagaca ggatctcagt agtccaggct | 120 |
| ttagtcctga ctcaacaata ccaccagcta aaaccactag aatacgagcc acaataaata | 180 |
| aaagatttta tttagtttcc agaaaaaggg gggaatgaaa gacccaccaa aattgcttag | 240 |
| cctgatgccg ctgtaacgcc attttgcaag gcatggaaaa ataccaaacc aagaatagag | 300 |
| aagttcagat caagggcggg tacatgaaaa tagctaacgt tgggccaaac aggatatctg | 360 |
| cggtgagcag tttcggcccc ggcccggggc caagaacaga tggtcaccgc agtttcggcc | 420 |
| ccggcccgag gccaagaaca gatggtcccc agatatggcc caaccctcag cagtttctta | 480 |
| agacccatca gatgtttcca ggctccccca aggacctgaa atgaccctgc gccttatttg | 540 |
| aattaaccaa tcagcctgct tctcgcttct gttcgcgcgc ttctgcttcc cgagctctat | 600 |
| aaaagagctc acaaccccctc actcggcgcg ccagtcctcc gacagactga gtcgcccggg | 660 |
| tacc | 664 |

<210> SEQ ID NO 41
<211> LENGTH: 544
<212> TYPE: DNA
<213> ORGANISM: Artificial Sequence
<220> FEATURE:
<223> OTHER INFORMATION: Synthetic nucleic acid sequence

<400> SEQUENCE: 41

| ggatctgcga tcgctccggt gcccgtcagt gggcagagcg cacatcgccc acagtccccg | 60 |
| agaagttggg gggaggggtc ggcaattgaa ccggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc ttttttcgcaa cgggtttgcc gccagaacac | 240 |
| agctgaagct cgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctac | 544 |

<210> SEQ ID NO 42
<211> LENGTH: 717
<212> TYPE: DNA
<213> ORGANISM: Artificial sequence
<220> FEATURE:
<223> OTHER INFORMATION: synthetic polynucleotide

<400> SEQUENCE: 42

| atggtctcca aagggaaga gctgttcacc ggcgtggtgc ccatcctggt cgagctggat | 60 |
| ggggatgtga atgggcataa atttagcgtg tccggggaag gggaagggga tgccacctac | 120 |
| ggcaagctga ccctgaagtt catctgcacc accggcaagc tccctgtccc ttggcccacc | 180 |
| ctcgtgacca ccctgactta tggcgtgcag tgcttcagcc gctaccctga ccatatgaaa | 240 |

```
cagcacgatt tcttcaagtc cgccatgcct gaggggtatg tgcaggaacg gactatcttt      300
ttcaaagacg atgggaatta taagacccgg gccgaagtca agttcgaggg cgacacactc      360
gtgaaccgca tcgaactcaa agggattgat tttaaggagg atgggaatat tctggggcac      420
aaactggagt acaactacaa cagccacaac gtctatatca tggccgacaa gcagaagaac      480
ggcattaaag tgaacttcaa gatccgccac aacatcgaag atggcagcgt ccagctcgcc      540
gatcattatc aacagaacac ccccatcggc gacgggcctg tcctcctccc tgataaccac      600
tacctgagca cccagtccgc cctgagcaaa gaccctaatg aaaagcgcga tcacatggtc      660
ctgctggagt tcgtgacagc tgctggcatc actctgggga tggatgaact ctataaa        717
```

<210> SEQ ID NO 43
<211> LENGTH: 13621
<212> TYPE: DNA
<213> ORGANISM: Artificial Sequence
<220> FEATURE:
<223> OTHER INFORMATION: synthetic polynucleotide

<400> SEQUENCE: 43

```
tctagaacta gtggatctta gccactttt aaaagaaaag ggggactgg aagggctaat         60 tcactcccaa cgaagacaag atatccttga tctgtggatc taccacacac aaggctactt      120
ccctgattgg cagaactaca caccagggcc aggggtcaga tatccactga cctttggatg      180
gtgctacaag ctagtaccag ttgagccaga taaggtagaa gaggccaata aaggagagaa      240
caccagcttg ttacaccctg tgagcctgca tggaatggat gaccctgaga gagaagtgtt      300
agagtggagg tttgacagcc gcctagcatt tcatcacgtg gcccgagagc tgcatccgga      360
gtacttcaag aactgctgac atcgagcttc ctacaaggga ctttccgctg ggactttcc      420 agggaggcgt ggcctgggcg ggactgggga gtggcgagcc ctcagatgct gcatataagc      480
agctgctttt tgcctgtact gggtctctct ggttagacca gatttgagcc tgggagctct      540
ctggctaact agggaaccca ctgcttaagc ctcaataaag cttgccttga gtgcttcaag      600
tagtgtgtgc ccgtctgttg tgtgactctg gtaactagag atccctcaga ccctttagt      660 cagtgtggaa aatctctagc agtggcgccc gaacaggac ttgaaagcga agggaaacc      720 agaggagctc tctcgacgca ggactcggct tgctgaagcg cgcacggcaa gaggcgaggg      780
gcggcgactg gtgagtacgc caaaaatttt gactagcgga ggctagaagg agagagatgg      840
gtgcgagagc gtcggtatta agcggggag aattagataa atgggaaaaa attcggttaa      900
ggccaggggg aagaaaacaa tataaactaa aacatatagt atgggcaagc agggagctag      960
aacgattcgc agttaatcct ggccttttag agacatcaga aggctgtaga caaatactgg     1020
gacagctaca accatccctt cagacaggat cagaagaact tagatcatta taataacaa     1080 tagcagtcct ctattgtgtg catcaaagga tagatgtaaa agacaccaag gaagccttag     1140
ataagataga ggaagagcaa aacaaaagta agaaaaaagc acagcaagca gcagctgaca     1200
caggacacag cagccaggtc agccaaaatt accctatagt gcagaacatc caggggcaaa     1260
tggtacatca ggccatatca cctagaactt taaatgcatg ggtaaaagta gtagaagaga     1320
aggctttcag cccagaagtg atacccatgt tttcagcatt atcagaagga gccaccccac     1380
aagatttaaa caccatgcta aacacagtgg ggggacatca agcagccatg caaatgttaa     1440
aagagaccat caatgaggaa gctgcagaat gggatagagt gcatccagtg catgcagggc     1500
ctattgcacc aggccagatg agagaaccaa ggggaagtga catagcagga actactagta     1560
```

```
cccttcagga acaaatagga tggatgacac ataatccacc tatcccagta ggagaaatct    1620
ataaaagatg gataatcctg ggattaaata aaatagtaag aatgtatagc cctaccagca    1680
ttctggacat aagacaagga ccaaaggaac cctttagaga ctatgtagac cgattctata    1740
aaactctaag agccgagcaa gcttcacaag aggtaaaaaa ttggatgaca gaaaccttgt    1800
tggtccaaaa tgcgaaccca gattgtaaga ctattttaaa agcattggga ccaggagcga    1860
cactagaaga aatgatgaca gcatgtcagg gagtggggggg acccggccat aaagcaagag    1920
tttttggctga agcaatgagc caagtaacaa atccagctac cataatgata cagaaaggca    1980
attttaggaa ccaaagaaag actgttaagt gtttcaattg tggcaaagaa gggcacatag    2040
ccaaaaattg cagggcccct aggaaaaagg ctgttggaa atgtggaaag aaggacacc      2100
aaatgaaaga ttgtactgag agacaggcta attttttagg gaagatctgg ccttcctaca    2160
agggaaggcc agggaatttt cttcagagca gaccagagcc aacagcccca ccatttcttc    2220
agagcagacc agagccaaca gccccaccag aagagagctt caggtctggg gtagagacaa    2280
caactccctc tcagaagcag gagccgatag acaaggaact gtatccttta acttccctca    2340
gatcactctt tggcaacgac ccctcgtcac aataaagata gggggggcaac taaaggaagc    2400
tctattagat acaggagcag atgatacagt attagaagaa atgagtttgc caggaagatg    2460
gaaaccaaaa atgatagggg gaattggagg ttttatcaaa gtaagacagt atgatcagat    2520
actcatagaa atctgtggac ataaagctat aggtacagta ttagtaggac ctacacctgt    2580
caacataatt ggaagaaatc tgttgactca gattggttgc actttaaatt ttcccattag    2640
tcctattgaa actgtaccag taaaattaaa gccaggaatg gatggcccaa agttaaaca     2700
atggccattg acagaagaaa aaataaaagc attagtagaa atttgtacag aaatggaaaa    2760
ggaagggaaa atttcaaaaa ttgggcctga aaatccatac aatactccag tatttgccat    2820
aaagaaaaaa gacagtacta atggagaaa attagtagat ttcagagaac ttaataagag    2880
aactcaagac ttctgggaag ttcaattagg aataccacat cccgcagggt taaaaaagaa    2940
aaaatcagta acagtactgg atgtgggtga tgcatatttt tcagttccct tagatgaaga    3000
cttcaggaag tatactgcat ttaccatacc tagtataaac aatgagacac cagggattag    3060
atatcagtac aatgtgcttc cacagggatg gaaaggatca ccagcaatat tccaaagtag    3120
catgacaaaa atcttagagc cttttagaaa acaaaatcca gacatagtta tctatcaata    3180
catggatgat ttgtatgtag gatctgactt agaaataggg cagcatagaa caaaaataga    3240
ggagctgaga caacatctgt tgaggtgggg acttaccaca ccagacaaaa acatcagaa     3300
agaacctcca ttcctttgga tgggttatga actccatcct gataaatgga cagtacagcc    3360
tatagtgctg ccagaaaaag acagctggac tgtcaatgac atacagaagt tagtgggaaa    3420
attgaattgg gcaagtcaga tttacccagg gattaaagta aggcaattat gtaaactcct    3480
tagaggaacc aaagcactaa cagaagtaat accactaaca gaagaagcag agctagaact    3540
ggcagaaaac agagagattc taaaagaacc agtacatgga gtgtattatg acccatcaaa    3600
agacttaata gcagaaatac agaagcaggg gcaaggccaa tggacatatc aaatttatca    3660
agagccattt aaaaatctga aaacaggaaa atatgcaaga cgaggggtg cccacactaa    3720
tgatgtaaaa caattaacag aggcagtgca aaaaataacc acagaaagca tagtaatatg    3780
ggaaagact cctaaattta aactacccat acaaaaggaa acatgggaaa catggtggac    3840
agagtattgg caagccacct ggattcctga gtgggagttt gtcaataccc ctcctttagt    3900
gaaattatgg taccagttag agaaagaacc catagtagga gcagaaacgt tctatgtaga    3960
```

```
tggggcagct agcagggaga ctaaattagg aaaagcagga tatgttacta atagaggaag    4020
acaaaaagtt gtcaccctaa ctgacacaac aaatcagaag actgagttac aagcaattca    4080
tctagctttg caggattcgg gattagaagt aaatatagta acagactcac aatatgcatt    4140
aggaatcatt caagcacaac cagataaaag tgaatcagag ttagtcaatc aaataataga    4200
gcagttaata aaaaggaaa aggtctatct ggcatgggta ccagcacaca aaggaattgg    4260
aggaaatgaa caagtagata aattagtcag tgctggaatc aggaaagtac tatttttaga    4320
tggaatagat aaggcccaag atgaacatga gaaatatcac agtaattgga gagcaatggc    4380
tagtgatttt aacctgccac ctgtagtagc aaaagaaata gtagccagct gtgataaatg    4440
tcagctaaaa ggagaagcca tgcatggaca agtagactgt agtccaggaa tatggcaact    4500
agattgtaca catttagaag gaaaagttat cctggtagca gttcatgtag ccagtggata    4560
tatagaagca gaagttattc cagcagaaac agggcaggaa acagcatact ttcttttaaa    4620
attagcagga agatggccag taaaaacaat acatacagac aatggcagca atttcaccag    4680
tactacggtt aaggccgcct gttggtgggc gggaatcaag caggaatttg gaattcccta    4740
caatccccaa agtcaaggag tagtagaatc tatgaataaa gaattaaaga aaattatagg    4800
ccaggtaaga gatcaggctg aacatcttaa gacagcagta caaatggcag tattcatcca    4860
caattttaaa agaaaagggg ggattggggg gtacagtgca ggggaaagaa tagtagacat    4920
aatagcaaca gacatacaaa ctaaagaatt acaaaaacaa attacaaaaa ttcaaaattt    4980
tcgggtttat tacagggaca gcagagatcc actttggaaa ggaccagcaa agctcctctg    5040
gaaaggtgaa ggggcagtag taatacaaga taatagtgac ataaaagtag tgccaagaag    5100
aaaagcaaag atcattaggg attatggaaa acagatggca ggtgatgatt gtgtggcaag    5160
tagacaggat gaggattaga acatggaaaa gtttagtaaa acaccatatg tatgtttcag    5220
ggaaagctag gggatggttt tatagacatc actatgaaag ccctcatcca agaataagtt    5280
cagaagtaca catcccacta ggggatgcta gattggtaat aacaacatat tggggtctgc    5340
atacaggaga aagagactgg catctgggtc agggagtctc catagaatgg aggaaaaaga    5400
gatatagcac acaagtagac cctgaactag cagaccaact aattcatctg tattactttg    5460
actgtttttc agactctgct ataagaaagg ccttattagg acatatagtt agccctaggt    5520
gtgaatatca agcaggacat aacaaggtag gatctctaca atacttggca ctagcagcat    5580
taataacacc aaaaaagata aagccacctt tgcctagtgt tacgaaactg acagaggata    5640
gatggaacaa gccccagaag accaagggcc acagagggag ccacacaatg aatggacact    5700
agagctttta gaggagctta agaatgaagc tgttagacat tttcctagga tttggctcca    5760
tggcttaggg caacatatct atgaaactta tggggatact tgggcaggag tggaagccat    5820
aataagaatt ctgcaacaac tgctgtttat ccatttcaga attgggtgtc gacatagcag    5880
aataggcgtt actcaacaga ggagagcaag aaatggagcc agtagatcct agactagagc    5940
cctggaagca tccaggaagt cagcctaaaa ctgcttgtac cacttgctat tgtaaaaagt    6000
gttgctttca ttgccaagtt tgtttcacaa caaaagcctt aggcatctcc tatggcagga    6060
agaagcggag acagcgacga agacctcctc aaggcagtca gactcatcaa gtttctctat    6120
caaagcagta agtagtacat gtaatgcaac ctatacaaat agcaatagca gcattagtag    6180
tagcaataat aatagcaata gttgtgtggt ccatagtaat catagaatat aggaaaatat    6240
taagacaaag aaaaatagac aggttaattg atagactaat agaaagagca gaagacagtg    6300
```

```
gcaatgagag tgaaggagaa atatcagcac ttgtggagat gggggtggaa atggggcacc    6360
atgctccttg ggatattgat gatctgtagt gctacagaaa aattgtgggt cacagtctat    6420
tatggggtac ctgtgtggaa ggaagcaacc accactctat tttgtgcatc agatgctaaa    6480
gcatatgata cagaggtaca taatgtttgg gccacacatg cctgtgtacc cacagacccc    6540
aacccacaag aagtagtatt ggtaaatgtg acagaaaatt ttaacatgtg gaaaaatgac    6600
atggtagaac agatgcatga ggatataatc agtttatggg atcaaagcct aaagccatgt    6660
gtaaaattaa ccccactctg tgttagttta aagtgcactg atttggggaa tgctactaat    6720
accaatagta gtaataccaa tagtagtagc ggggaaatga tgatggagaa aggagagata    6780
aaaaactgct ctttcaatat cagcacaagc ataagaggta aggtgcagaa agaatatgca    6840 ttttttata acttgatat aataccaata gataatgata ctaccagcta tacgttgaca    6900
agttgtaaca cctcagtcat tacacaggcc tgtccaaagg tatcctttga gccaattccc    6960
atacattatt gtgccccggc tggttttgcg attctaaaat gtaataataa gacgttcaat    7020
ggaacaggac catgtacaaa tgtcagcaca gtacaatgta cacatggaat taggccagta    7080
gtatcaactc aactgctgtt gaatggcagt ctagcagaag aagaggtagt aattagatct    7140
gccaatttca cagacaatgc taaaaccata atagtacagc tgaaccaatc tgtagaaatt    7200
aattgtacaa gacccaacaa caatacaaga aaaagtatcc gtatccagag gggaccaggg    7260
agagcatttg ttacaatagg aaaaatagga aatatgagac aagcacattg taacattagt    7320
agagcaaaat ggaatgccac tttaaaacag atagctagca aattaagaga acaatttgga    7380
aataataaaa caataatctt taagcaatcc tcaggagggg acccagaaat tgtaacgcac    7440
agttttaatt gtggagggga attttttctac tgtaattcaa cacaactgtt taatagtact    7500
tggtttaata gtacttggag tactgaaggg tcaaataaca ctgaaggaag tgacacaatc    7560
acactcccat gcagaataaa acaatttata aacatgtggc aggaagtagg aaaagcaatg    7620
tatgcccctc ccatcagcgg acaaattaga tgttcatcaa atattacagg gctgctatta    7680
acaagagatg gtggtaataa caacaatggg tccgagatct cagacctgg aggaggagat    7740 atgagggaca attggagaag tgaattatat aaatataaag tagtaaaaat tgaaccatta    7800
ggagtagcac ccaccaaggc aaagagaaga gtggtgcaga gagaaaaaag agcagtggga    7860
ataggagctt tgttccttgg gttcttggga gcagcaggaa gcactatggg cgcagcgtca    7920
atgacgctga cggtacaggc cagacaatta ttgtctggta tagtgcagca gcagaacaat    7980
ttgctgaggg ctattgaggc gcaacagcat ctgttgcaac tcacagtctg ggcatcaag    8040 cagctccagg caagaatcct ggctgtggaa agatacctaa aggatcaaca gctcctgggg    8100
atttggggtt gctctggaaa actcatttgc accactgctg tgccttggaa tgctagttgg    8160
agtaataaat ctctggaaca gatttggaat aacatgacct ggatggagtg ggacagagaa    8220
attaacaatt acacaagctt aatacattcc ttaattgaag aatcgcaaaa ccagcaagaa    8280
aagaatgaac aagaattatt ggaattagat aaatgggcaa gtttgtggaa ttggtttaac    8340
ataacaaatt ggctgtggta tataaaaata ttcataatga tagtaggagg cttggtaggt    8400
ttaagaatag ttttgctgt actttctata gtgaatagag ttaggcaggg atattcacca    8460
ttatcgtttc agacccacct cccaaccccg aggggacccg acaggcccga aggaatagaa    8520
gaagaaggtg gagagagaga cagagacaga tccattcgat tagtgaacgg atccttggca    8580
cttatctggg acgatctgcg gagcctgtgc ctcttcagct accaccgctt gagagactta    8640
ctcttgattg taacgaggat tgtggaactt ctgggacgca gggggtggga agccctcaaa    8700
```

```
tattggtgga atctcctaca atattggagt caggagctaa agaatagtgc tgttagcttg    8760
ctcaatgcca cagccatagc agtagctgag gggacagata gggttataga agtagtacaa    8820
ggagcttgta gagctattcg ccacatacct agaagaataa gacagggctt ggaaaggatt    8880
ttgctataag catggtctcc aaaggggaag agctgttcac cggcgtggtg cccatcctgg    8940
tcgagctgga tggggatgtg aatgggcata aatttagcgt gtccggggaa ggggaagggg    9000
atgccaccta cggcaagctg accctgaagt tcatctgcac caccggcaag ctccctgtcc    9060
cttggcccac cctcgtgacc accctgactt atggcgtgca gtgcttcagc cgctaccctg    9120
accatatgaa acagcacgat ttcttcaagt ccgccatgcc tgaggggtat gtgcaggaac    9180
ggactatctt tttcaaagac gatgggaatt ataagacccg ggccgaagtc aagttcgagg    9240
gcgacacact cgtgaaccgc atcgaactca aagggattga ttttaaggag gatgggaata    9300
ttctggggca caaactggag tacaactaca acagccacaa cgtctatatc atggccgaca    9360
agcagaagaa cggcattaaa gtgaacttca agatccgcca caacatcgaa gatggcagcg    9420
tccagctcgc cgatcattat caacagaaca cccccatcgg cgacgggcct gtcctcctcc    9480
ctgataacca ctacctgagc acccagtccg ccctgagcaa agaccctaat gaaaagcgcg    9540
atcacatggt cctgctggag ttcgtgacag ctgctggcat cactctgggg atggatgaac    9600
tctataaata aagcgaccct cgagtactag gatccattag gcggccgcgg atctgcgatc    9660
gctccggtgc ccgtcagtgg gcagagcgca catcgcccac agtccccgag aagttggggg    9720
gaggggtcgg caattgaacc ggtgcctaga gaaggtggcg cggggtaaac tgggaaagtg    9780
atgtcgtgta ctggctccgc ctttttcccg agggtggggg agaaccgtat ataagtgcag    9840
tagtcgccgt gaacgttctt tttcgcaacg ggtttgccgc cagaacacag ctgaagcttc    9900
gaggggctcg catctctcct tcacgcgccc gccgccctac ctgaggccgc catccacgcc    9960
ggttgagtcg cgttctgccg cctcccgcct gtggtgcctc ctgaactgcg tccgccgtct   10020
aggtaagttt aaagctcagg tcgagaccgg gcctttgtcc ggcgctccct tggagcctac   10080
ctagactcag ccggctctcc acgctttgcc tgaccctgct tgctcaactc tacgtctttg   10140
tttcgttttc tgttctgcgc cgttacagat ccaagctgtg accggcgcct acgctagcgc   10200
taccggtcgc caccatggtt tctgtgatca gcccgaaat gaagatgagg tactacatgg   10260
acggcagcgt caatggacat gagtttacga tcgaagggga gggcaccggc cgaccctacg   10320
agggccacca ggagatgacc ctgagggtga cgatggcaga gggcggtccc atgcccttcg   10380
ccttcgacct ggtaagccac gtgttctgct acggccaccg agtgttcaca aaatacccgg   10440
aggagatccc agactacttc aagcaggcct ttcccgaggg gctgagctgg gagaggagcc   10500
tggaatttga ggacggtggc agtgctagcc ttagcgccca catcagtctg aggggcaaca   10560
ccttttacca caagagcaag ttcactggcg ttaacttccc agcggacggc cccatcatgc   10620
agaaccagag cgtggactgg gagcccagca ccgagaagat caccgccagc gacggcgtgc   10680
tgaagggcga cgtgaccatg tacctgaagc tggaaggagg tggcaaccat aagtgccaga   10740
tgaagaccac ctacaaggcc gccaaggaga ttctggagat gccgggagac cactatattg   10800
gacacaggct ggtccgaaag actgaaggta acatcaccga acaggtggaa gacgccgtgg   10860
cccactacag ctaggctcga gacctggaaa acatggagc aatcacaagt agcaatacag   10920
cagctaccaa tgctgcttgt gcctggctag aagcacaaga ggaggaggag gtgggttttc   10980
cagtcacacc tcaggtacct ttaagaccaa tgacttacaa ggcagctgta gatcttagcc   11040
```

```
acttttaaa agaaaggggg ggactggaag ggctaattca ctcccaacga agacaagata    11100
tccttgatct gtggatctac cacacacaag gctacttccc tgattggcag aactacacac    11160
cagggccagg ggtcagatat ccactgacct ttggatggtg ctacaagcta gtaccagttg    11220
agccagataa ggtagaagag gccaataaag gagagaacac cagcttgtta cacctgtga    11280 gcctgcatgg aatggatgac cctgagagag aagtgttaga gtggaggttt gacagccgcc    11340
tagcatttca tcacgtggcc cgagagctgc atccggagta cttcaagaac tgctgacatc    11400
gagcttgcta caagggactt tccgctgggg actttccagg gaggcgtggc ctgggcggga    11460
ctggggagtg gcgagccctc agatgctgca tataagcagc tgcttttgc ctgtactggg    11520 tctctctggt tagaccagat ttgagcctgg gagctctctg gctaactagg gaacccactg    11580
cttaagcctc aataaagctt gccttgagtg cttcaagtag tgtgtgcccg tctgttgtgt    11640
gactctggta actagagatc cctcagaccc ttttagtcag tgtggaaaat ctctagcagt    11700
ggcgatgaat taattcttga agacgaaagg gcctcgtgat acgcctattt ttataggtta    11760
atgtcatgat aataatggtt tcttagacgt caggtggcac ttttcgggga aatgtgcgcg    11820
gaacccctat ttgttttattt ttctaaatac attcaaatat gtatccgctc atgagacaat    11880
aaccctgata aatgcttcaa taatattgaa aaaggaagag tatgagtatt caacatttcc    11940
gtgtcgccct tattcccttt tttgcggcat tttgccttcc tgttttgct cacccagaaa    12000 cgctggtgaa agtaaaagat gctgaagatc agttgggtgc acgagtgggt tacatcgaac    12060
tggatctcaa cagcggtaag atccttgaga gttttcgccc cgaagaacgt tttccaatga    12120
tgagcacttt taaagttctg ctatgtggcg cggtattatc ccgtgttgac gccgggcaag    12180
agcaactcgg tcgccgcata cactattctc agaatgactt ggttgagtac tcaccagtca    12240
cagaaaagca tcttacggat ggcatgacag taagagaatt atgcagtgct gccataacca    12300
tgagtgataa cactgcggcc aacttacttc tgacaacgat cggaggaccg aaggagctaa    12360 ccgcttttt gcacaacatg ggggatcatg taactcgcct tgatcgttgg aaccggagc    12420 tgaatgaagc cataccaaac gacgagcgtg acaccacgat gcctgcagca atggcaacaa    12480
cgttgcgcaa actattaact ggcgaactac ttactctagc ttcccggcaa caattaatag    12540
actggatgga ggcggataaa gttgcaggac cacttctgcg ctcggccctt ccggctggct    12600
ggtttattgc tgataaatct ggagccggtg agcgtgggtc tcgcggtatc attgcagcac    12660
tggggccaga tggtaagccc tcccgtatcg tagttatcta cacgacgggg agtcaggcaa    12720
ctatggatga acgaaataga cagatcgctg agataggtgc ctcactgatt aagcattggt    12780
aactgtcaga ccaagtttac tcatatatac tttagattga tttaaaactt cattttaat    12840 ttaaaaggat ctaggtgaag atccttttg ataatctcat gaccaaaatc ccttaacgtg    12900
agttttcgtt ccactgagcg tcagaccccg tagaaaagat caaaggatct tcttgagatc    12960
ctttttttct gcgcgtaatc tgctgcttgc aaacaaaaaa accaccgcta ccagcggtgg    13020
tttgtttgcc ggatcaagag ctaccaactc tttttccgaa ggtaactggc ttcagcagag    13080
cgcagatacc aaatactgtc cttctagtgt agccgtagtt aggccaccac ttcaagaact    13140
ctgtagcacc gcctacatac ctcgctctgc taatcctgtt accagtggct gctgccagtg    13200
gcgataagtc gtgtcttacc gggttggact caagacgata gttaccggat aaggcgcagc    13260
ggtcgggctg aacggggggt tcgtgcacac agcccagctt ggagcgaacg acctacaccg    13320
aactgagata cctacagcgt gagctatgag aaagcgccac gcttcccgaa gggagaaagg    13380
cggacaggta tccggtaagc ggcagggtcg gaacaggaga gcgcacgagg gagcttccag    13440
```

-continued

```
ggggaaacgc ctggtatctt tatagtcctg tcgggtttcg ccacctctga cttgagcgtc    13500
gatttttgtg atgctcgtca gggggggcgga gcctatggaa aaacgccagc aacgcggcct    13560
ttttacggtt cctggccttt tgctggcctt ttgctcacat gttctttcct gcgttatccg    13620
c                                                                    13621
```

<210> SEQ ID NO 44
<211> LENGTH: 36
<212> TYPE: PRT
<213> ORGANISM: Artificial sequence
<220> FEATURE:
<223> OTHER INFORMATION: synthetic amino acid sequence

<400> SEQUENCE: 44

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

<210> SEQ ID NO 45
<211> LENGTH: 657
<212> TYPE: DNA
<213> ORGANISM: Artificial Sequence
<220> FEATURE:
<223> OTHER INFORMATION: synthetic polynucleotide

<400> SEQUENCE: 45

```
atggtgagtg tgattaaacc agagatgaag atgaggtact acatggacgg ctccgtcaat      60
gggcatgagt tcacaattga aggtaaggc acaggcagac cttacgaggg acatcaagag     120
atgacactac gcgtcacaat ggccgagggc gggccaatgc cttcgcgtt tgacttagtg      180 tcacacgtgt tctgttacgg ccacagagta tttactaaat atccagaaga gataccagac     240
tatttcaaac aagcatttcc tgaaggcctg tcatgggaaa ggtcgttgga gttcgaagat     300
ggtgggtccg cttcagtcag tgcgcatata agccttagag gaaacacctt ctaccacaaa     360
tccaaattta ctggggttaa ctttcctgcc gatggtccta tcatgcaaaa ccaaagtgtt     420
gattgggagc catcaaccga gaaaattact gccagcgacg gagttctgaa gggtgatgtt     480
acgatgtacc taaaacttga aggaggcggc aatcacaaat gccaaatgaa gactacttac     540
aaggcggcaa aagagattct tgaaatgcca ggagaccatt acatcggcca tcgcctcgtc     600
aggaaaaccg aaggcaacat tactgagcag gtagaagatg cagtagctca ttcctaa       657
```

DUAL-COLOR HIV REPORTER SYSTEM FOR THE DETECTION OF LATENTLY-INFECTED CELLS

CROSS-REFERENCE

This application claims the benefit of U.S. Provisional Patent Application No. 61/866,847, filed Aug. 16, 2013, which application is incorporated herein by reference in its entirety.

STATEMENT REGARDING FEDERALLY SPONSORED RESEARCH

This invention was made with government support under Grant Nos. 1DP1 DA031126 and RO1 DA030216 awarded by the National Institutes of Health (NIH). The government has certain rights in the invention.

INCORPORATION BY REFERENCE OF SEQUENCE LISTING PROVIDED AS A TEXT FILE

A Sequence Listing is provided herewith as a text file, "GLAD-407WO SeqList_ST25.txt" created on Aug. 6, 2014 and having a size of 76 KB. The contents of the text file are incorporated by reference herein in their entirety.

INTRODUCTION

Immunodeficiency viruses such as human immunodeficiency virus (HIV), simian immunodeficiency virus (SIV), and feline immunodeficiency virus (FIV) hijack a host organism's immune system by targeting the animal's T cells. Without treatment, immunodeficiency viral infection can lead to acquired immunodeficiency syndrome (AIDS).

The discovery of effective therapies against HIV, called highly active antiretroviral therapy (HAART), has transformed a once deadly disease into a life-long chronic condition. By attacking the viral machinery during infection, HAART effectively reduces infection to undetectable levels. Nonetheless, complete suppression of viral replication by HAART cannot clear HIV infection and the virus reappears rapidly upon treatment interruption. HIV persists under HAART in a rare population of long-lived, latently infected cells. HIV latency constitutes the main barrier for clearing HIV infection from patients. In addition, the persistence of latent reservoirs feeds an inflammatory-like state that contributes to the development of accelerated aging phenotypes and accompanying age-related diseases in the HAART-treated HIV-positive population.

Latently-infected cells are extremely rare in patients and carry silent integrated HIV genomes. Current technologies do not allow the identification and purification of live infected cells that do not express HIV proteins. Latency has therefore been studied "a posteriori" via reactivation of expression of the latent provirus. This type of analysis has allowed the quantification of latent cells in different lymphoid populations and the testing of different drugs that reactivate latent HIV. However, the inability to identify latently infected cells before reactivation has precluded a full understanding of the latency process and hindered the discovery of additional drugs the reactivate latent HIV.

A major obstacle in the development of an eradication-based cure for HIV is the virus' ability to establish latent infection. There is a need in the art for compositions and methods that allow for the identification, isolation, and/or purification of cells latently infected with an immunodeficiency virus.

LITERATURE

Dahabieh et al, J Virol. 2013 April; 87(8):4716-27; Hakre et al., FEMS Microbiol Rev. 2012 May;36(3):706-16; U.S. Patent Publication No. 20030013078; U.S. Patent Publication No. 20080118494; U.S. Pat. Nos. 6,984,718; 7,183,047.

SUMMARY

The present disclosure provides recombinant nucleic acids, and cells and virions comprising the recombinant nucleic acids, that can be used to identify, isolate, and/or purify cells latently infected with immunodeficiency virus. A subject recombinant nucleic acid includes (a) a first nucleotide sequence encoding a first reporter polypeptide that produces a first detectable signal, where the first nucleotide sequence is operably linked to an immunodeficiency virus promoter and is translated as an early gene; and (b) a second nucleotide sequence encoding a second reporter polypeptide that produces a second detectable signal that is distinguishable from the first detectable signal, where the second nucleotide sequence is operably linked to a non-immunodeficiency virus promoter. In some cases, the first and second nucleotide sequences are both positioned between a shared 5' long terminal repeat (LTR) and a shared 3' LTR.

In some cases, a subject recombinant nucleic acid further comprises a functional transactivation response element (TAR) and a nucleotide sequence encoding a functional transactivator protein (Tat). In some cases, the first nucleotide sequence is inserted into the locus of an early gene selected from nef, tat, and rev. In some cases, at least one of the first and second reporter polypeptides is a fluorescent protein. In some cases, one of the first and second reporter polypeptides is a red fluorescent protein, and the other is a green fluorescent protein. In some cases, one of the first and second reporter polypeptides is an orange fluorescent protein, and the other is a green fluorescent protein. In some cases, the non-immunodeficiency virus promoter is selected from a group consisting of: an EF1α promoter, a Spleen Focus Forming Virus promoter, a ubiquitin promoter, and a cytomegalovirus (CMV) promoter.

The present disclosure further provides methods of isolating a latently infected cell. Such methods include: (a) introducing into a population of cells a subject recombinant nucleic acid, and (b) selecting a cell that is positive for the second detectable signal and is negative for the first detectable signal. In some cases, the method further comprises, between steps (a) and (b), contacting the population of cells with an agent that activates human immunodeficiency virus (HIV) transcription.

The present disclosure further provides methods of identifying an agent that activates a latent immunodeficiency virus. Such methods include: (a) contacting a latently infected cell, which is infected with a subject recombinant nucleic acid, with a test agent; (b) measuring the amount of the first detectable signal; and (c) determining the effect, if any, of the test agent on the amount of the first detectable signal. In such cases, when an increase is measured in the amount of the first detectable signal in a cell contacted with the test agent relative to a cell not contacted with the test agent, the test agent is determined to activate the latent immunodeficiency virus. In some cases the latently infected cell is first isolated according to subject methods above prior to contacting the cell with a test agent.

Features

The present disclosure features a recombinant nucleic acid comprising: (a) a first nucleotide sequence encoding a first reporter polypeptide that produces a first detectable signal, where the first nucleotide sequence is operably linked to an immunodeficiency virus promoter and is translated as an early gene; and (b) a second nucleotide sequence encoding a second reporter polypeptide that produces a second detectable signal that is distinguishable from the first detectable signal, wherein the second nucleotide sequence is operably linked to a non-immunodeficiency virus promoter (a promoter other than an immunodeficiency virus promoter). The first and second nucleotide sequences are both positioned between a shared 5' long terminal repeat (LTR) and a shared 3' LTR. In some cases, the recombinant nucleic acid encodes a transcription-competent immunodeficiency virus and further comprises: i) a functional transactivation response element (TAR); and ii) a third nucleotide sequence, where the third nucleotide sequence encodes a functional transactivator protein (Tat) and is positioned between the shared 5' long terminal repeat (LTR) and the shared 3' LTR. In some cases, the immunodeficiency virus is a human immunodeficiency virus (HIV), e.g., HIV-1 or HIV-2. In some cases, the first nucleotide sequence is inserted into the locus of an early gene; e.g., where the early gene is selected from: nef, tat, and rev. In some instances, the early gene is nef. In some cases, the early gene is the early gene that is most proximal to the 3' LTR. In some cases, the first nucleotide sequence is inserted into an early gene locus in a manner such that the protein encoded by the early gene is not functional or is not produced. In some cases, the first nucleotide sequence is inserted into an early gene locus in a manner such that a protein encoded by the early gene is a fusion protein comprising the protein encoded by the early gene and the first reporter polypeptide. In some cases, at least one of the first and second reporter polypeptides is a fluorescent protein. For example, in some cases, the first reporter polypeptide is a red fluorescent protein, and the second reporter polypeptide is a green fluorescent protein; or the first reporter polypeptide is a green fluorescent protein, and the second reporter polypeptide is a red fluorescent protein. In some instances, the non-immunodeficiency virus promoter is selected from a group consisting of: an EF1α promoter, a Spleen Focus Forming Virus promoter, a ubiquitin promoter, and a cytomegalovirus (CMV) promoter. In some cases, the 5' LTR comprises the immunodeficiency virus promoter.

The present disclosure also features a virion comprising a recombinant nucleic acid of the present disclosure. The present disclosure also features an isolated cell genetically modified with the recombinant nucleic acid of the present disclosure. In some cases, the recombinant nucleic acid is integrated into the cell's genome. In some cases, the cell is a T cell. In some cases, the cell is a primary T cell.

The present disclosure features a method of isolating a latently infected cell, the method comprising: (a) introducing into a population of cells a recombinant nucleic acid of the present disclosure, and (b) selecting a cell that is positive for the second detectable signal and is negative for the first detectable signal. In some instances, the method further comprises, between steps (a) and (b), contacting the population of cells with an agent that activates HIV transcription. In some cases, the introducing step comprises contacting the cell with the recombinant nucleic acid. In some cases, the introducing step comprises contacting the cell with a virion comprising the recombinant nucleic acid. In some cases, selecting step (b) comprises selecting a population of cells that are positive for the second detectable signal and are negative for the first detectable signal. In some cases, the method further comprises: c) contacting the selected cells with an agent that activates HIV transcription to produce a contacted cell population; and d) measuring the level of the first detectable signal in two or more cells of the contacted cell population.

The present disclosure features a latently infected cell isolated according to a method of the present disclosure for isolating a latently infected cell.

The present disclosure features a method of identifying an agent that activates a latent immunodeficiency virus, the method comprising: (a) contacting a latently infected cell with a test agent, wherein the latently infected cell is isolated according a method of the present disclosure; (b) measuring the amount of the first detectable signal; and (c) determining the effect, if any, of the test agent on the amount of the first detectable signal, wherein when an increase is measured in the amount of the first detectable signal in a cell contacted with the test agent relative to a cell not contacted with the test agent, the test agent is determined to activate the latent immunodeficiency virus. In some cases, the latently infected cell is isolated prior to the contacting step. In some cases, the first reporter polypeptide is a fluorescent polypeptide and the first detectable signal is fluorescence of the first reporter polypeptide.

The present disclosure features a method of reactivating latent immunodeficiency virus in an immunodeficiency virus-infected cell, the method comprising contacting the cell with a synergistically effective amount of a first active agent that reactivates latent immunodeficiency virus and a second agent selected from a quinone epoxide inhibitor of Bruton's tyrosine kinase, an adenosine reuptake inhibitor, and a resveratrol analog, wherein the first agent and the second agent synergistically reactivate the latent immunodeficiency virus. In some cases, the first active agent is selected from an HDAC inhibitor (e.g., SAHA), prostratin, and TNF-α. In some cases, the second active agent is selected from terreic acid, dilazep, and piceatannol.

The present disclosure features a method of treating a human immunodeficiency virus infection in an individual, the method comprising: a) administering to an individual a synergistically effective amount of: i) a first active agent that reactivates latent immunodeficiency virus and; ii) a second agent selected from a quinone epoxide inhibitor of Bruton's tyrosine kinase, an adenosine reuptake inhibitor, and a resveratrol analog; and b) administering to the individual an effective amount of an agent(s) that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity. In some cases, one or both of said administering steps is by a vaginal route of administration, by a rectal route of administration, by an oral route of administration, or by an intravenous route of administration.

The present disclosure features a method of reactivating latent immunodeficiency virus in an immunodeficiency virus-infected cell, the method comprising contacting the cell with a tyrphostin, e.g., with a tyrphostin of any one of Formulas I-IV.

The present disclosure features a method of treating a human immunodeficiency virus infection in an individual, the method comprising: a) administering to an individual a tyrphostin (e.g., with a tyrphostin of any one of Formulas I-IV); and b) administering to the individual an effective amount of an agent(s) that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

The present disclosure features a method of reactivating latent immunodeficiency virus in an immunodeficiency virus-infected cell, the method comprising contacting the cell with a selective p38 MAPK inhibitor, e.g., with a selective p38 MAPK inhibitor of any one of Formulas V-VII.

The present disclosure features a method of treating a human immunodeficiency virus infection in an individual, the method comprising: a) administering to an individual a selective p38 MAPK inhibitor (e.g., with a selective p38 MAPK inhibitor of any one of Formulas V-VII); and b) administering to the individual an effective amount of an agent(s) that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

BRIEF DESCRIPTION OF THE DRAWINGS

FIG. 1D, Top panel: 89.6 U39362.2 (SEQ ID NO: 30); 89mASG (SEQ ID NO: 31); HXB2 NC001802 (SEQ ID NO: 32); R7/E-/GFP (SEQ ID NO: 33); R7GEmC (SEQ ID NO: 33). FIG. 1D, Bottom panel: rows 2 and 3, middle (SEQ ID NO: 34); rows 2 and 3, right (SEQ ID NO: 35); bottom row, left (SEQ ID NO: 36); bottom row, middle (SEQ ID NO: 37); bottom row, right (SEQ ID NO: 38).

FIGS. 6A-B depict FACS analysis demonstrating primary T-cell infection and reactivation with an integrase inhibitor.

FIG. 7 provides Table 2, which lists compounds from the Tocriscreen drug library that reactivated latent HIV.

FIGS. 10A-D demonstrate the use of HIV-1 reporter virus for the purification of double negative, productively infected, and latently infected cells and related analysis thereof.

DEFINITIONS

Figure 1:
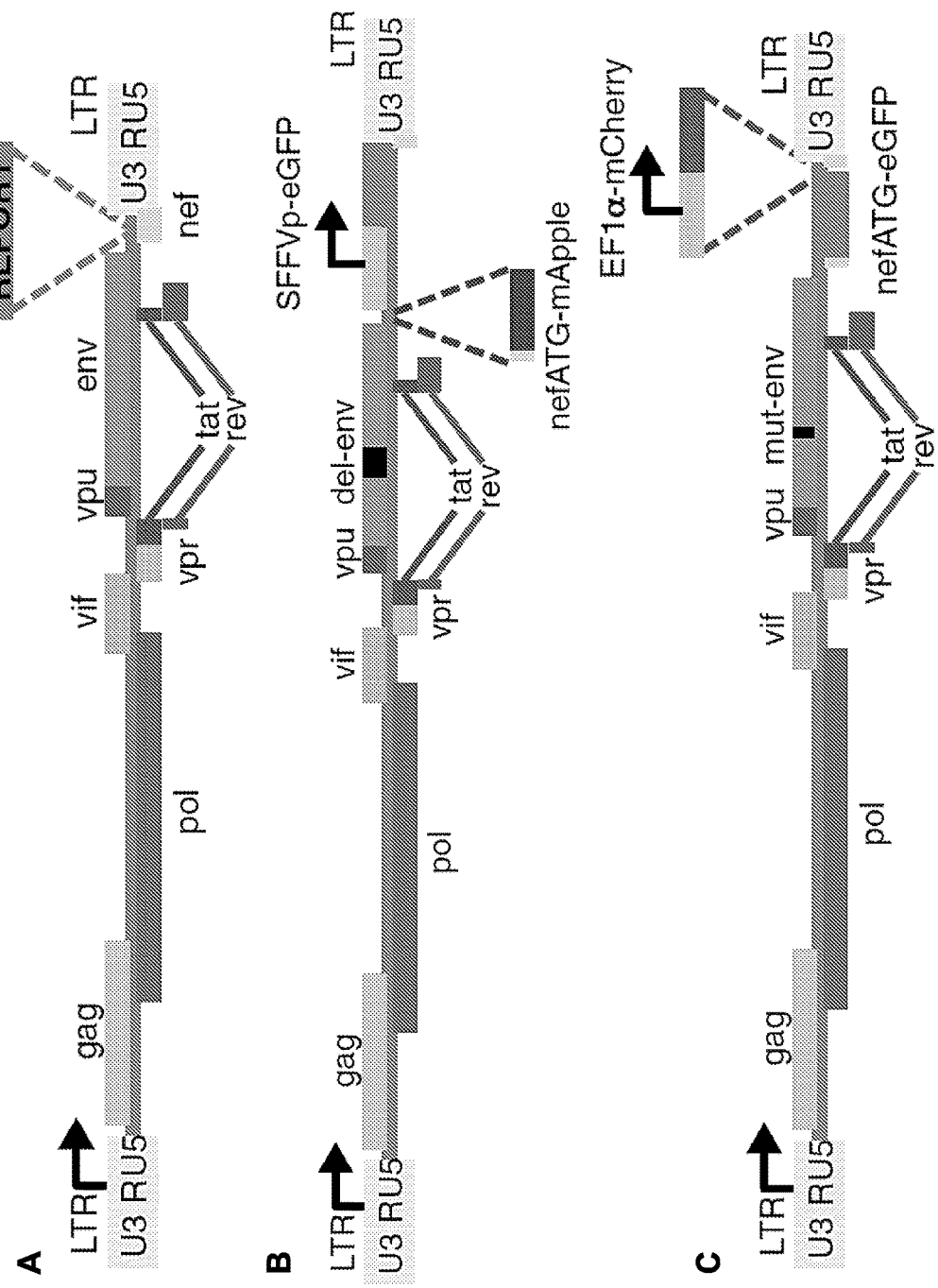
FIGS. 1A-K demonstrate that the subject recombinant nucleic acids can be used to identify a population of latently infected cells.
Figure 1:
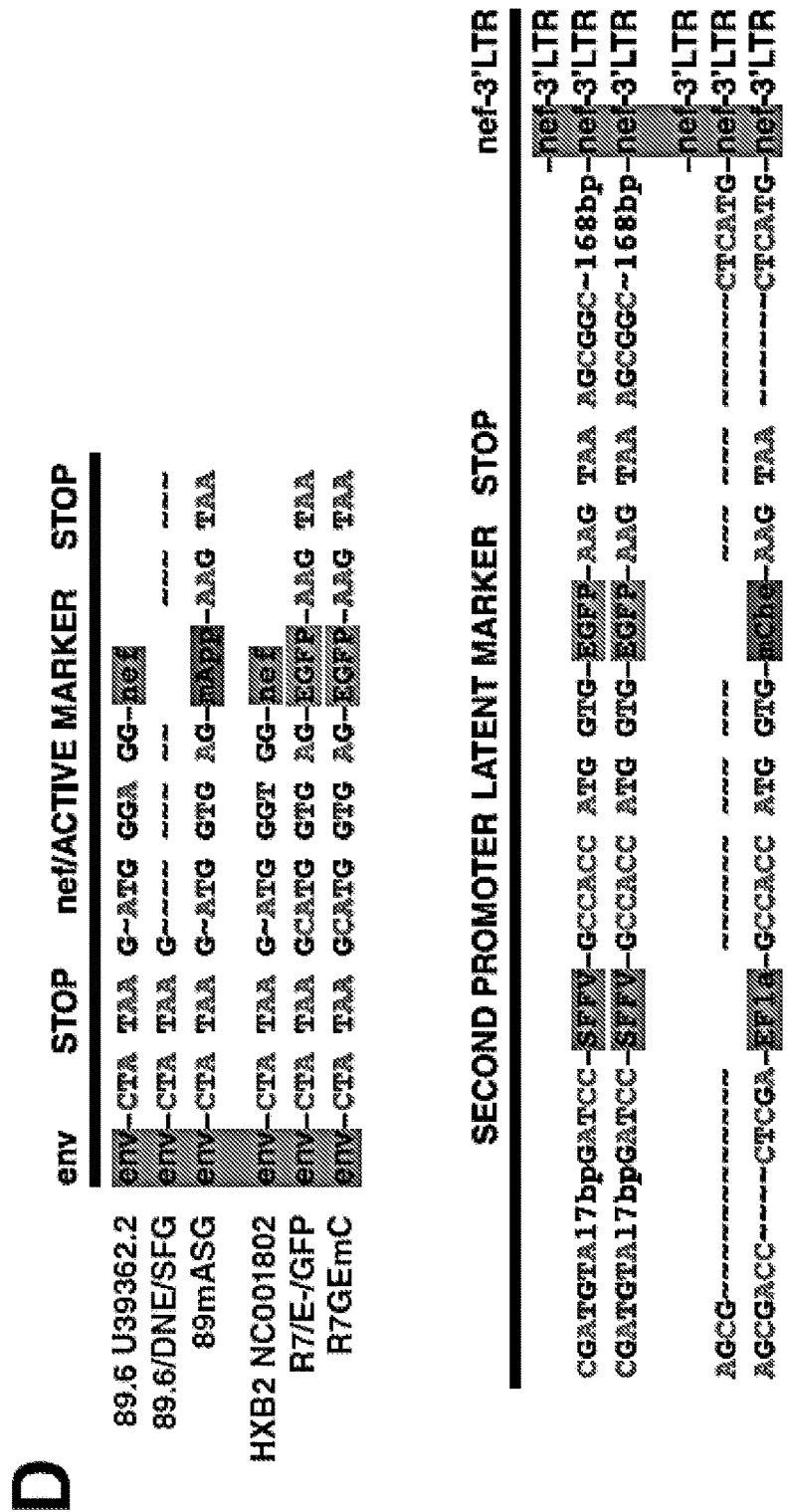
Figure 1:
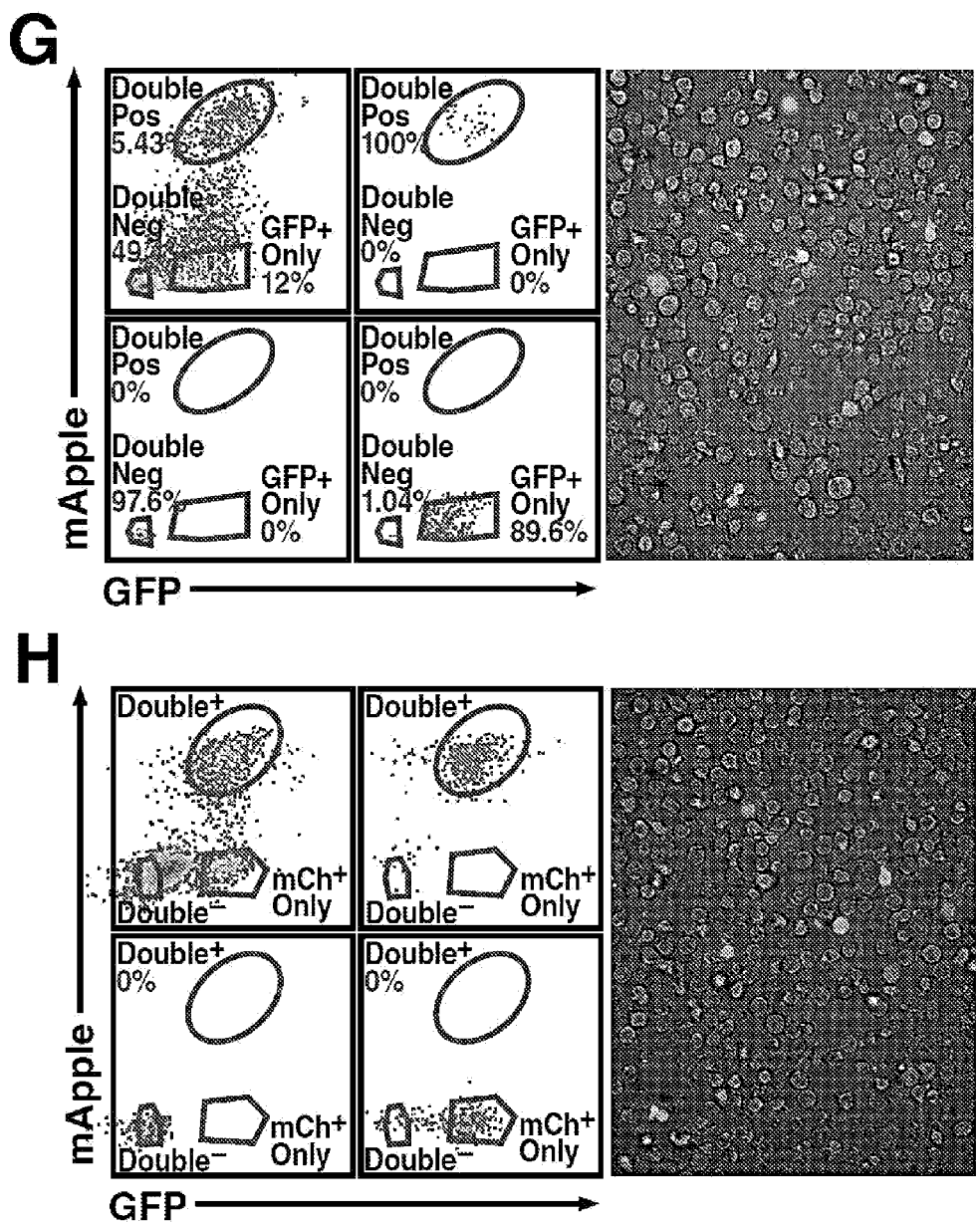
Figure 1:
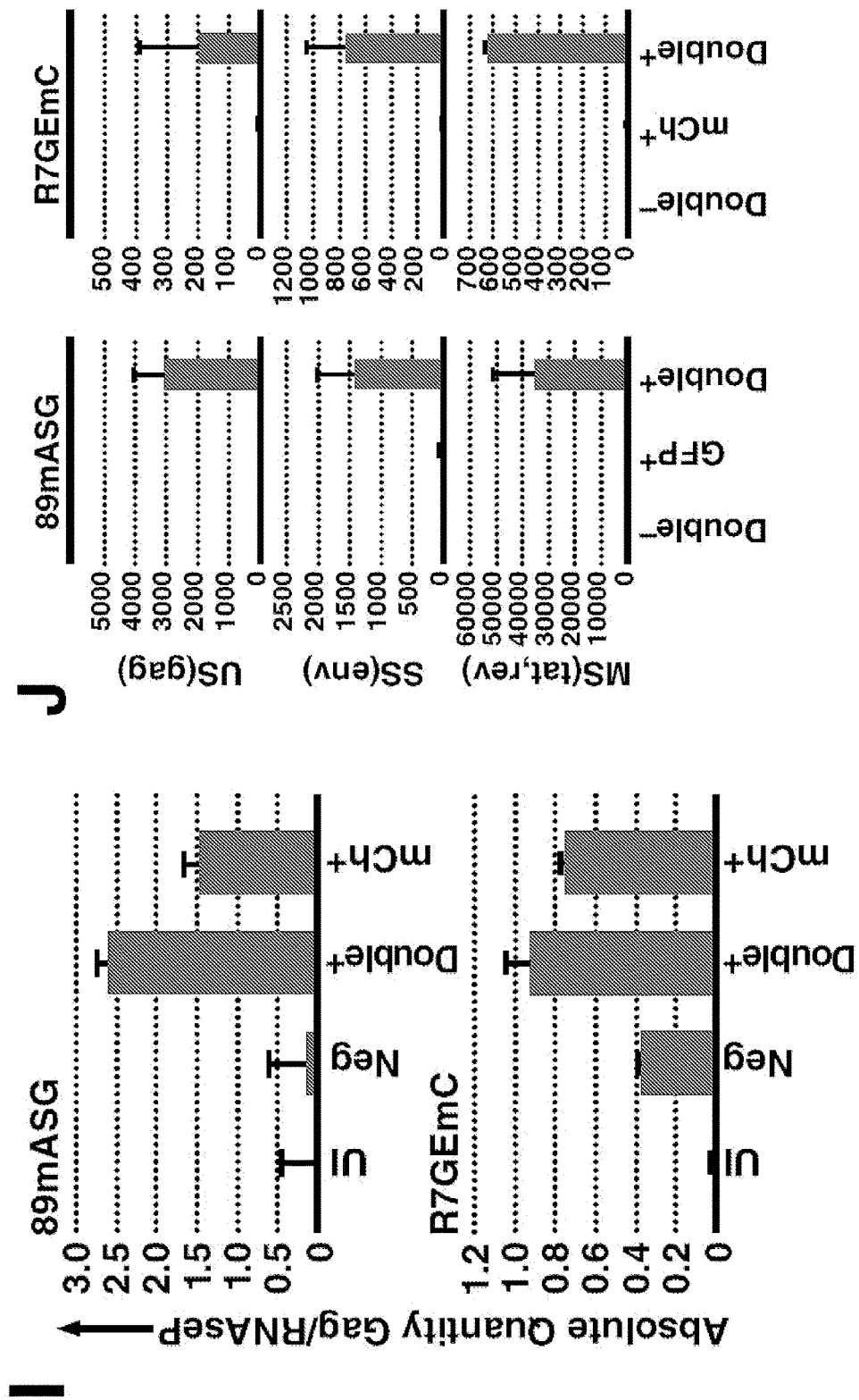
Figure 1:
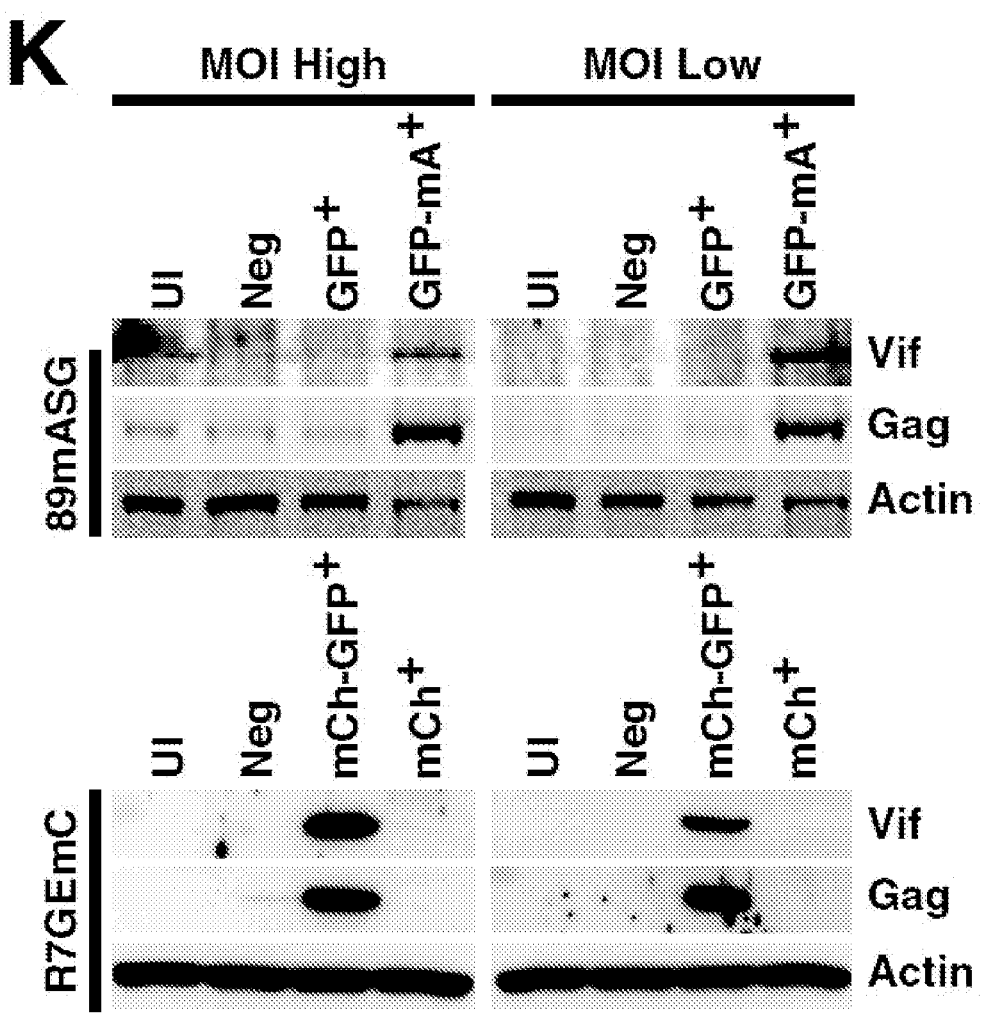

The term "immunodeficiency virus" as used herein, refers to human immunodeficiency virus-1 (HIV-1); human immunodeficiency virus-2 (HIV-2); any of a variety of HIV subtypes and quasispecies; simian immunodeficiency virus (SW); and feline immunodeficiency virus (FIV). As used herein in the context of latent immunodeficiency virus in a subject isolated cell, the term also includes immunodeficiency virus-based retroviral vectors (e.g., recombinant immunodeficiency virus, subject recombinant nucleic acids, etc.).

The genome of an immunodeficiency virus comprises early genes and late genes. The term "early genes" as used herein refers to immunodeficiency virus genes that are translated early (relative to the late genes) after viral genome transcription initiates. Likewise, the term "late genes" as used herein refers to immunodeficiency virus genes that are translated late (relative to the early genes) after viral genome transcription initiates.

Late genes are transcribed along with early genes because both early and late genes are present in the same primary transcript. However, the primary transcript contains multiple splice donor and splice acceptor sites, which accounts for a high degree of alternative splicing and the generation of multiple splice variants. The splice variants vary in gene content as well as reading frame. The splice variants that are in the proper reading frame for the translation of late genes also contain intron-like sequences, preventing them from being exported out of the cellular nucleus for translation. Thus, although late genes are "transcribed" along with early genes as part of the same primary transcript, they are not translated until the late gene-encoding transcripts can exit the nucleus (with the aid of the Rev protein, as described below), allowing for translation. Late genes are considered to be Rev-dependent.

To the contrary, early genes are translated before late genes because the splice variants that are in the proper reading frame for the translation of early genes do not contain intron-like sequences, and therefore exit the nucleus for translation. Early genes are considered to be Rev-independent.

As an illustrative non-limiting example of the above, human immunodeficiency virus (HIV) genes can be divided into early genes (tat, rev, and nef) and late genes (gag, pol, env, vpr, vpu, and vif). The primary HIV-1 transcript contains multiple splice donors (5' splice sites) and splice acceptors (3' splice sites), which can be processed to yield more than 30 alternative mRNAs. Many of the mRNAs are polycistronic, i.e., they contain the open reading frame of more than one protein.

HIV-1 mRNAs fall into three size classes:

(i) unspliced RNA: the unspliced 9-kb primary transcript can be expressed to generate the Gag and Gag-Pol precursor proteins or be packaged into virions to serve as the genomic RNA;

(ii) incompletely spliced RNA: these mRNAs use the splice donor site located nearest the 5' end of the HIV RNA genome in combination with any of the splice acceptors located in the central region of the virus (these RNAs can potentially express Env, Vif, Vpu, Vpr, and the single-exon form of Tat); and (iii) fully spliced RNA: these mRNAs have spliced out both introns of HIV and have the potential to express Rev, Nef, and the two-exon form of Tat (these heterogeneous mRNAs do not require the expression of the Rev protein).

In normal cells, intron-containing RNAs must be completely spliced before they can exit the nucleus. This regulation is essential because it prevents the translation of intronic sequences contained in partially spliced mRNAs. In cells infected with an immunodeficiency virus, the virally encoded Rev protein (encoded by an early gene) binds to viral RNAs that retain intron sequences, and directs their export from the nucleus. This export allows the unconventional viral RNAs (which encode late genes) to bypass the normal "check point" of RNA splicing. The fully spliced viral mRNAs exit the nucleus along with the majority of cellular mRNAs. Thus, threshold levels of Rev are necessary for exporting intron-containing HIV mRNAs, explaining why those mRNA splice variants encode proteins of the viral late genes. In contrast, the fully spliced mRNA variants (Nef, Tat, and Rev), can be translated immediately, explaining why those mRNA splice variants encode proteins of the viral early genes.

The phrase "translated as an early gene" refers to a scenario in which a heterologous sequence (i.e., a non-immunodeficiency virus sequence, e.g., a sequence encoding a reporter polypeptide) is operably linked to a promoter of an immunodeficiency virus and would be considered an early gene if it were a natural existing sequence of the viral genome. In other words, the heterologous sequence is translated from at least one splice variant that is free to leave the nucleus in the absence of Rev (a Rev-independent splice variant).

As one non-limiting illustrative example, a heterologous sequence is "translated as an early gene" when the heterologous sequence has been inserted into the viral genome into the locus of an early gene (either replacing the viral gene or generating a sequence that encodes a fusion protein between the protein encoded by the heterologous sequence and the protein encoded by the early gene).

The term "long terminal repeat" or "LTR" as used herein refers to the sequences of DNA that repeat hundreds or thousands of times found at either end of proviral DNA formed by reverse transcription of retroviral RNA. LTRs are used by viruses to insert their genetic material into host genomes (e.g., the ends of the LTRs participate in integration of the provirus into the host genome). For example, the HIV-1 LTR is approximately 640 bp in length and, like other retroviral LTRs, is segmented into the U3, R, and U5 regions. The multi-step process of reverse transcription results in the placement of two identical LTRs, each consisting of a U3, R, and U5 region, at either end of the proviral DNA.

U3 and U5 have been further subdivided according to transcription factor sites and their impact on LTR activity and viral gene expression. The U3 region (for unique 3' sequence) is usually approximately 450-basepairs (bp) in length and is located at the 5' end of each LTR. The U3 region contains most of the cis-acting DNA elements, which are the binding sites for cellular transcription factors. The central region of each LTR contains the usually 100-bp R (for repeated sequence) region. Transcription usually begins at the first base of the R region and polyadenylation usually occurs immediately after the last base of R. The U5 region (for unique 5' sequence) is roughly 180-bp in length and, in the case of HIV, contains the Tat binding site and packaging sequences of HIV. The 3' end of U5 is defined by the location of a lysyl tRNA binding site. The lysyl tRNA acts as a primer for reverse transcription. Once the provirus has been integrated into the host genome, the LTR on the 5' end usually serves as the promoter for the entire retroviral genome.

The LTR is normally the control center for immunodeficiency virus gene expression. As may be expected because of the integrated phase of their life cycle, immunodeficiency viruses have somewhat typical eukaryotic promoters with transcriptional enhancers and some also have regulatory elements responsive to either viral or specialized cellular (e.g. hormonal) trans-activating factors. Enhancer functions have also been mapped to the gag and gag-pol (e.g., in SIV and HIV) regions of some viruses. All of the requisite signals for gene expression are usually found in the LTRs: Enhancer, promoter, transcription initiation (capping), transcription terminator and polyadenylation signal. Expression directed by the viral LTR signals is carried out entirely by host cell enzymes (RNA pol II, poly A synthetase, guanyl transferase, etc.). The enhancer and other transcription regulatory signals are contained in the U3 region of the 5' LTR, and the TATA box is located roughly 25 bp from the beginning of the R sequence.

The integrated provirus has two LTRs, and the 5' LTR normally acts as an RNA polymerase (pol) II promoter. The transcript begins, by definition, at the beginning of R, is capped, and proceeds through U5 and the rest of the provirus, usually terminating by the addition of a poly A tract just after the R sequence in the 3' LTR. Occasionally the stop signal in the 3' LTR is "read-through" and terminated in host flanking sequences.

The 3' LTR is not normally functional as a promoter, although it has exactly the same sequence arrangement as the 5' LTR. Instead, the 3' LTR acts in transcription termination and polyadenylation. Transcriptional interference occurs when the two LTRs are oriented as in a provirus; the 5' LTR has dominant control as a promoter. When the integrity of the 5' LTR is disrupted, the 3' LTR can act as a promoter.

The terms "latent," "latency," and the like, are used herein in the context of a latent immunodeficiency virus, and refer to a genomically integrated immunodeficiency virus (including a latent immunodeficiency virus-based retroviral vector, e.g., a subject recombinant nucleic acid) that is transcriptionally silent, e.g., immunodeficiency virus transcripts are undetectable or are at background levels, in a cell comprising the latent immunodeficiency virus. However, because subject recombinant nucleic acids include a nucleotide sequence that (i) encodes a second reporter polypeptide; and (ii) is operably linked to a non-immunodeficiency virus promoter, transcripts encoding the second reporter polypeptide (and the second reporter polypeptide itself) can still be detected in the context of a subject transcriptionally silent (latent) virus. Thus, latently infected cells are (i) positive for the second reporter polypeptide (and/or the polynucleotide encoding the second reporter polypeptide), which is operably linked to a non-immunodeficiency virus promoter; and (ii) negative for the first reporter polypeptide, which is translated as an early gene.

The term "transcription competent" as used herein in the context of transcription-competent latent immunodeficiency virus (and/or a transcription-competent subject recombinant nucleic acid), refers to a latent immunodeficiency virus (and/or a transcription-competent subject recombinant nucleic acid) that has a functional promoter (i.e., a promoter that can be activated to transcribe a primary transcript that includes (i) at least one early gene; and/or (ii) at least one heterologous sequence that can be translated as an early gene). For example, in some cases, a transcription-competent latent immunodeficiency virus (and/or a transcription-competent subject recombinant nucleic acid) encodes functional Tat and has a functional TAR site in the LTR. In some embodiments, a transcription-competent latent immunodeficiency virus (and/or a transcription-competent subject recombinant nucleic acid) comprises a nucleotide sequence encoding a reporter polypeptide that is translated as an early gene (e.g., inserted into the locus of an early gene), where the nucleotide sequence encoding the reporter polypeptide is operably linked to a functional immunodeficiency virus promoter (e.g., an intact promoter in the 5' and/or 3' LTR).

The term "reactivate," as used herein in the context of reactivating an immunodeficiency virus, refers to an immunodeficiency virus that, after a period of latency, becomes transcriptionally active, and in many instances forms infectious viral particles. This term can applied in in vitro and/or in vivo contexts. In those embodiments in which a recombinant immunodeficiency virus (e.g., in some cases, a reactivated recombinant immunodeficiency virus) is not replication competent, the recombinant immunodeficiency virus can be packaged into infectious particles by providing any missing viral proteins (e.g., gag and env proteins) via a helper virus.

As used herein the term "isolated," in the context of a subject isolated cell, refers to a cell that is in an environment different from that in which the cell naturally occurs. An isolated cell can exist in a population of cells that includes cells of other types and/or cells with different characteristics than the isolated cell. For example, an isolated latently infected cell can exist in a population of cells that includes both uninfected and infected cells.

As used herein the term "purified," in the context of a subject purified cell (e.g., "purified cells", "a purified cell population", "a population of purified cells", etc.) refers to a cell population that is isolated and is enriched for cells of a particular cell type and/or a particular characteristic. For example, the phrases "a purified population of latently infected cells", or to "purify latently infected cells", and the like, refer to the isolation and enrichment of latently infected cells. In the context of a subject purified population of cells, latently infected cells can be considered purified when they constitute about 60% or more (e.g., 65% or more, 70% or more, 75% or more, 80% or more, 85% or more, 90% or more, 92% or more, 95% or more, 97% or more, 98% or more, 99% or more, or 100%) of the cells of an isolated cell population.

As used herein, the term "clonal cell line" refers to a cloned cell line that is typically immortalized, e.g., under suitable in vitro culture conditions, the cell line divides virtually indefinitely. Isolated cells are also referred to herein as "host cells."

The term "host cell" includes an individual cell or cell culture which can be or has been a recipient of any recombinant vector(s) or construct of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vitro with a recombinant vector (e.g., a recombinant virion) or a construct of the invention. A host cell which comprises a recombinant vector or construct of the invention is a "recombinant host cell."

"Recombinant" as used herein, means that a particular nucleic acid (DNA or RNA) is the product of various combinations of cloning, restriction, polymerase chain reaction (PCR) and/or ligation steps resulting in a nucleic acid having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms. Alternatively, DNA sequences encoding RNA that is not translated may also be considered recombinant Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects the transcription or expression of the coding sequence.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA (or RNA that is subsequently used as a template to produce DNA, e.g., retroviral RNA that is reverse transcribed into DNA inside of the cell), when such DNA (or RNA as described above) has been introduced inside the cell. The presence of the exogenous DNA (or RNA as described above) results in permanent or transient genetic change. The transforming DNA (e.g., DNA transcribed from RNA) may or may not be integrated (covalently linked) into the genome of the cell. With respect to eukaryotic cells, a stably transformed cell is one in which the transforming DNA (e.g., DNA transcribed from RNA) has become integrated into a chromosome so that it can be inherited by daughter cells through chromosome replication. This stability can be demonstrated, for example, by the ability of the eukaryotic cell to establish cell lines or clones that comprise a population of daughter cells containing the transforming DNA.

A "clone" is a population of cells derived from a single cell or common ancestor by mitosis. A "cell line" is a clone of a primary cell that is capable of stable growth in vitro for many generations.

As used herein, the terms "treat," "treatment" "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of immunodeficiency virus infection, the term "treatment" encompasses prevention of establishment of a systemic infection following initial contact with the virus; and prophylactic treatment of an individual not yet infected with the virus.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "synergistic combination" or a "synergistic amount" of a first agent and a second agent is a combined dosage that is more effective in reactivating a latent immunodeficiency virus than the incremental improvement in treatment outcome that could be predicted or expected from a merely additive combination of the first agent or the second agent when administered at that same dosage as a monotherapy.

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group.

Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O) O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spino ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorphinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O) OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O) NR$^{80}$R$^{80}$, —NR$^{70}$C(NR$^{70}$)R$^{70}$ and —NR$^{70}$C(NR$^{70}$) NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a first reporter polypeptide" includes a plurality of such first reporter polypeptides and reference to "a genetically modified cell" includes reference to one or more such genetically modified cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides recombinant nucleic acids, as well as cells and virions comprising the recombinant nucleic acids, which can be used to identify, isolate, and/or purify cells latently infected with immunodeficiency virus. A subject recombinant nucleic acid includes (a) a first nucleotide sequence encoding a first reporter polypeptide that produces a first detectable signal, where the first nucleotide sequence is operably linked to an immunodeficiency virus promoter and is translated as an early gene; and (b) a second nucleotide sequence encoding a second reporter polypeptide that produces a second detectable signal that is distinguishable from the first detectable signal, where the second nucleotide sequence is operably linked to a non-immunodeficiency virus promoter. In some aspects, the first and second nucleotide sequences are both positioned between a shared 5' long terminal repeat (LTR) and a shared 3' LTR. Also provided are methods of using the subject provides recombinant nucleic acids, cells, and virions.

Recombinant Nucleic Acids

The present disclosure provides recombinant nucleic acids that include (a) a first nucleotide sequence encoding a first reporter polypeptide that produces a first detectable signal, where the first nucleotide sequence is operably linked to an immunodeficiency virus promoter and is translated as an early gene; and (b) a second nucleotide sequence encoding a second reporter polypeptide that produces a second detectable signal that is distinguishable from the first detectable signal, where the second nucleotide sequence is operably linked to a non-immunodeficiency virus promoter (a promoter other than an immunodeficiency virus promoter), and where the first and second nucleotide sequences are both positioned between a shared 5' long terminal repeat (LTR) and a shared 3' LTR. A subject recombinant nucleic acid, in some cases, is referred to herein as a "recombinant immunodeficiency virus." Such term encompasses a subject recombinant nucleic acid as well a virion comprising a subject recombinant nucleic acid.

The latent immunodeficiency virus (or subject recombinant nucleic acid) is transcription competent. Recombinant immunodeficiency virus is also referred to as "immunodeficiency virus-derived vector," "immunodeficiency virus-based vector," or "immunodeficiency virus-based retroviral vector," or a "subject recombinant nucleic acid." In many embodiments, the recombinant immunodeficiency virus-based vector is generated using standard recombinant DNA methods, and comprises a reporter polypeptide (as described in more detail below).

In some embodiments, the latent immunodeficiency virus is a recombinant version of a wild-type immunodeficiency virus. HIV genome sequences are known in the art for a variety of HIV-1 and HIV-2 strains, and can be found in GenBank under various accession numbers, including AJ203647, AAAJ302646; AF133821, NC001802, L36874, and NC001722. SW genome sequences are known in the art for a variety of SIV strains, and can be found in GenBank under various accession numbers, including AF334679, and NC001549. Any of a variety of strains and quasispecies can be used.

In many some embodiments, the recombinant immunodeficiency virus is in a vector. Suitable vectors include, but are not limited to, plasmid vectors; Semliki forest virus vectors; vaccinia virus vectors; adenoviral vectors; and the like. Many such vectors are available commercially. To prepare the constructs, the immunodeficiency polynucleotide is inserted into a vector, typically by means of DNA ligase attachment to a cleaved restriction enzyme site in the vector. Ligase independent methods are also known in the art.

Recombinant vectors need not include the entire immunodeficiency virus genome. In many embodiments, a recombinant vector includes at least the long terminal repeat (LTR) from the immunodeficiency virus, a nucleotide sequence encoding the Tat protein, and nucleotide sequences encoding the first and second reporter polypeptides, where both the Tat-encoding sequence and the first reporter polypeptide-encoding sequences are operably linked to the viral LTR, e.g., are under transcriptional control of the viral LTR.

The recombinant vector may further include other elements, such as sequences necessary for propagation of the vector, such as an origin of replication for replication in a bacterial of eukaryotic cell; sequences encoding a selectable marker for selection of bacterial cells that contain the vector, such as antibiotic resistance genes (e.g., ampicillin resistance; and the like). Such elements are well known to those skilled in the art.

Exemplary recombinant nucleic acids include, e.g., 89mASG (SEQ ID NO:23) and R7GEmC (SEQ ID NO:29). In some embodiments, a subject recombinant nucleic acid comprises a nucleotide sequence having at least 75%, at least 80%, at least 85%, at least 90%, at least 95%, at least 98%, at least 99%, or 100%, nucleotide sequence identity to SEQ ID NO:23 or SEQ ID NO:29, over the entire length of SEQ ID NO:23 or SEQ ID NO:29.

Reporter Polypeptides

The term "reporter polypeptide" as used herein refers to a polypeptide that provides a detectable signal indicating that translation has occurred from the nucleotide sequence encoding the reporter polypeptide. In a subject recombinant vector, a first reporter polypeptide is operably linked to an immunodeficiency virus promoter and is translated as an early gene. Accordingly, translation (production) of the first reporter polypeptide indicates that viral transcription is active and that splice variants encoding early genes are exiting the nucleus and being translated. In some embodiments, the nucleotide sequence encoding the first reporter polypeptide is inserted into the locus of an early gene. In such cases, the early gene itself can be deleted or the early gene can remain at the locus.

In some embodiments, the nucleotide sequence encoding the first reporter polypeptide is inserted into the locus of at least one of the early genes nef, tat, and rev. In some cases, the nucleotide sequence encoding the first reporter polypeptide is inserted into the locus of the early gene that is most proximal to the 3' LTR. In some cases, the nucleotide sequence encoding the first reporter polypeptide is inserted into the locus of an early gene in a manner such that the protein encoded by the early gene is not functional or is not produced. In some cases, the nucleotide sequence encoding the first reporter polypeptide is inserted into the locus of the early gene in a manner such that a protein encoded by the locus of the early gene is a fusion between the protein encoded by the early gene and the first reporter polypeptide.

In some cases, the nucleotide sequence encoding the first reporter polypeptide is inserted into the locus of the early gene in a manner such that both open reading frames (of the first reporter polypeptide and the early gene) are translated from a single mRNA due to the presence of an internal ribosome entry site (IRES). A number of IRES elements are known in the art, and any such IRES can be used in a recombinant immunodeficiency virus-based vector. In some cases, the IRES is derived from the encephalomyocarditis virus. Naturally occurring IRES sequences are known in the art and include, but are not limited to, IRES sequences derived from mengovirus, bovine viral diarrhea virus (BVDV), hepatitis C virus (HCV; e.g., nucleotides 1202-1812 of the nucleotide sequence provided under GenBank Accession number AJ242654), GTX, Cyr61a, Cyr61b, poliovirus, the immunoglobulin heavy-chain-binding protein (BiP), immunoglobulin heavy chain, a picornavirus, murine encephalomyocarditis virus, poliovirus, and foot and mouth disease virus (e.g., nucleotide numbers 600-1058 of the nucleotide sequence provided under GenBank Accession No. AF308157). Other IRES sequences such as those reported in WO 96/01324; WO 98/49334; WO 00/44896; and U.S. Pat. No. 6,171,821 can be used.

In a subject recombinant vector, the second reporter polypeptide is operably linked to a non-immunodeficiency virus promoter. Accordingly, translation (production) of the second reporter polypeptide indicates that the subject recombinant nucleic acid is present and that the non-immunodeficiency virus promoter to which the second reporter polypeptide is operably linked is active. The non-immunodeficiency virus promoter can be any convenient promoter that is independent of the transcriptional control of the viral promoter. Many such promoters will be known to one of ordinary skill in the art. In some cases, non-immunodeficiency virus promoter is a constitutive promoter. In some cases, non-immunodeficiency virus promoter is a tissue-specific promoter. In some cases, non-immunodeficiency virus promoter is an inducible promoter. Examples of suitable non-immunodeficiency virus promoters include but are not limited to: an EF1α (EF1a) promoter, a Spleen Focus Forming Virus (SFFV) promoter, a ubiquitin (Ubc) promoter, and a cytomegalovirus (CMV) promoter.

In some cases, the non-immunodeficiency virus promoter is independent of the activation state of the host cell. For example, in some such cases when the host cell is a T cell, the non-immunodeficiency virus promoter is active in resting T cells. In some cases, the non-immunodeficiency virus promoter that is independent of the activation state of the host cell is selected from the group consisting of: an EF1α promoter, an SFFV promoter, and a Ubc promoter. In some cases, the non-immunodeficiency virus promoter functions (i.e., is active) in hematopoietic cells. In some such cases, the non-immunodeficiency virus promoter that is active in hematopoietic cells is an SFFV promoter.

A Spleen Focus Forming Virus (SFFV) promoter can comprise (although a more minimal sequence, i.e., a shorter sequence, may be known in the art, and such sequence is also suitable) a sequence that is 75% or more (e.g., 80% or more, 85% or more, 90% or more, 95% or more, 97% or more, 98% or more, 99% or more, 99.5% or more, 99.6% or more, 99.7% or more, 99.8% or more, 99.9% or more, or 100%) identical to the nucleotide sequence set forth in one of SEQ ID NOs: 20 and 40.

(SEQ ID NO: 20)
5'-
tagagcggccgccaccgcggtggaagctatccgccatcatggggtctctc attatactcctactcctactaattctgcttatttggaccctgtattctta atcaattagttcaatttgttaaagacaggatctcagtagtccaggcttta gtcctgactcaacaataccaccagctaaaaccactagaatacgagccaca ataaataaaagattttatttagtttccagaaaaagggggggaatgaaagac cccaccaaattgcttagcctgatgccgctgtaacgccattttgcaaggca tggaaaaataccaaaccaagaatagagaagttcagatcaagggcgggtac atgaaaatagctaacgttgggccaaacaggatatctgcggtgagcagttt cggcccggccggggccaagaacagatggtcaccgcagtttcggccccg gcccgaggccaagaacagatggtcccagatatggcccaaccctcagcag tttcttaagacccatcagatgtttccaggctcccccaaggacctgaaatg accctgcgccttatttgaattaaccaatcagcctgcttctcgcttctgtt cgcgcgcttctgatcccgagctctataaaagagctcacaacccctcactc ggcgcgccagtcctccgacagactgagtcgcccgggtaccgagctcggat ccactagtccagtgtggtggaattctgcagatatccagcacagtggcggc cgctcgagatccaccggccgtc-3';
and (SEQ ID NO: 40)
5'-tatccgccatcatggggtctctcattatactcctactcctactaatt ctgcttatttggaccctgtattcttaatcaattagttcaatttgttaaag acaggatctcagtagtccaggctttagtcctgactcaacaataccaccag ctaaaaccactagaatacgagccacaataaataaaagattttatttagtt tccagaaaaagggggggaatgaaagacccaccaaattgcttagcctgatg ccgctgtaacgccattttgcaaggcatggaaaaataccaaaccaagaata gagaagttcagatcaagggcgggtacatgaaaatagctaacgttgggcca aacaggatatctgcggtgagcagtttcggcccggcccggggccaagaac agatggtcaccgcagtttcggccccggcccgaggccaagaacagatggtc cccagatatggcccaaccctcagcagtttcttaagacccatcagatgttt ccaggctcccccaaggacctgaaatgaccctgcgccttatttgaattaac caatcagcctgcttctcgcttctgttcgcgcgcttctgatcccgagctc tataaaagagctcacaacccctcactcggcgcgccagtcctccgacagac tgagtcgcccgggtacc-3'.

An EF1α promoter (also known as an EF1a promoter) can comprise (although a more minimal sequence, i.e., a shorter sequence, may be known in the art, and such sequence is also suitable) a sequence that is 75% or more (e.g., 80% or more, 85% or more, 90% or more, 95% or more, 97% or more, 98% or more, 99% or more, 99.5% or more, 99.6% or more, 99.7% or more, 99.8% or more, 99.9% or more, or 100%) identical to the nucleotide sequence set forth in one of SEQ ID NOs: 26 and 41.

(SEQ ID NO: 26)
5'-gtactaggatccattaggcggccgcggatctgcgatcgct ccggtgcccgtcagtgggcagagcgcacatcgcccacagtccc cgagaagttgggggagggtcggcaattgaaccggtgcctag agaaggtggcgcgggtaaactgggaaagtgatgtcgtgtact ggctccgccttttccccgagggtgggggagaaccgtatataag tgcagtagtcgccgtgaacgttcttttttcgcaacgggtttgcc gccagaacacagctgaagatcgaggggctcgcatctctccttc acgcgcccgccgccctacctgaggccgccatccacgccggttg agtcgcgttctgccgcctcccgcctgtggtgcctcctgaactg cgtccgccgtctaggtaagtttaaagctcaggtcgagaccggg cctttgtccggcgctcccttggagcctacctagactcagccgg ctctccacgctttgcctgaccctgcttgctcaactctacgtat tgtttcgttttctgttctgcgccgttacagatccaagctgtga ccggcgcctacgctagcgctaccggtc-3';
and (SEQ ID NO: 41)
5'-ggatctgcgatcgctccggtgcccgtcagtgggcagagcg cacatcgcccacagtccccgagaagttgggggagggtcggc aattgaaccggtgcctagagaaggtggcgcgggtaaactggg aaagtgatgtcgtgtactggctccgccttttccccgagggtgg gggagaaccgtatataagtgcagtagtcgccgtgaacgttctt tttcgcaacgggtttgccgccagaacacagctgaagcttcgag gggctcgcatctctccttcacgcgcccgccgccctacctgagg ccgccatccacgccggttgagtcgcgttctgccgcctcccgcc tgtggtgcctcctgaactgcgtccgccgtctaggtaagtttaa agctcaggtcgagaccgggcctttgtccggcgctcccttggag cctacctagactcagccggctctccacgattgcctgaccagct tgctcaactctacgtattgtttcgttttctgttctgcgccgtt acagatccaagctgtgaccggcgcctac-3'.

A ubiquitin (Ubc) promoter can comprise (although a more minimal sequence, i.e., a shorter sequence, may be known in the art, and such sequence is also suitable) a sequence that is 75% or more (e.g., 80% or more, 85% or more, 90% or more, 95% or more, 97% or more, 98% or more, 99% or more, 99.5% or more, 99.6% or more, 99.7% or more, 99.8% or more, 99.9% or more, or 100%) identical to the nucleotide sequence set forth in SEQ ID NO:39.

(SEQ ID NO: 39)
ggcctccgcgccgggttttggcgcctcccgcgggcgccccctcctcac ggcgagcgctgccacgtcagacgaagggcgcaggagcgtcctgatcctt ccgcccggacgctcaggacagcggcccgctgctcataagactcggcctt agaacccagtatcagcagaaggacattttaggacgggacttgggtgac tctagggcactggttttctttccagagagcggaacaggcgaggaaaagt agtcccttctcggcgattctgcggagggatctccgtggggcggtgaacg -continued

```
ccgatgattatataaggacgcgccgggtgtggcacagctagttccgtcg cagccgggatttgggtcgcggttcttgtttgtggatcgctgtgatcgtc acttggtgagtagcgggctgctgggctggccggggctttcgtggccgcc gggccgctcggtgggacggaagcgtgtggagagaccgccaagggctgta gtctgggtccgcgagcaaggttgccctgaactgggggttgggggagcg cagcaaaatggcggctgttcccgagtcttgaatggaagacgcttgtgag gcgggctgtgaggtcgttgaaacaaggtgggggcatggtgggcggcaa gaacccaaggtcttgaggccttcgctaatgcgggaaagctcttattcgg gtgagatgggctggggcaccatctggggaccctgacgtgaagtttgtca ctgactggagaactcggtttgtcgtctgttgcggggcggcagttatgc ggtgccgttgggcagtgcaccgtacctttgggagcgcgcgccctcgtc gtgtcgtgacgtcaccgttctgttggcttataatgcagggtggggcca cctgccggtaggtgtgcggtaggcttttctccgtcgcaggacgcagggt tcgggcctagggtaggctctcctgaatcgacaggcgccggacctctggt gaggggagggataagtgaggcgtcagtttctttggtcggttttatgtac ctatcttcttaagtagctgaagctccggttttgaactatgcgctcgggg ttggcgagtgtgttttgtgaagttttttaggcacctttttgaaatgtaat catttgggtcaatatgtaattttcagtgttagactagtaaattgtccgc taaattctggccgttttttggcttttttgttagacg
```

Production of both the first and second reporter polypeptides (double positive) indicates that a subject recombinant nucleic acid is present, that the non-immunodeficiency virus promoter to which the second reporter polypeptide is operably linked is active, that viral transcription is active, and that splice variants encoding early genes are exiting the nucleus and being translated. Therefore, production of both the first and second reporter polypeptides indicates that a subject virus is active (i.e., not latent) and that the cell harboring the virus is not a latently infected cell.

In some cases, production of the first reporter polypeptide (where the first reporter polypeptide is encoded by a nucleotide sequence operably linked to an immunodeficiency virus promoter), without substantial production of the second reporter polypeptide (where the second reporter polypeptide is encoded by a nucleotide sequence operably linked to a promoter other than an immunodeficiency virus promoter), in a cell harboring a subject recombinant virus indicates that the recombinant virus is active (not latent), and that the cell harboring the recombinant virus is not a latently infected cell.

Production of the second reporter polypeptide, without production of (e.g., in the absence of translation of) the first reporter polypeptide (single positive for the second reporter polypeptide) indicates that a subject recombinant nucleic acid is present in the cell, that the non-immunodeficiency virus promoter to which the second reporter polypeptide is operably linked is active, and that viral transcription is inactive. Therefore, production of the second reporter polypeptide, and no substantial production of the first reporter polypeptide, indicates that a subject virus is transcriptionally inactive (i.e., latent, transcriptionally silent) and that the cell harboring the virus is a latently infected cell.

In some embodiments, a reporter polypeptide produces a signal and the signals produced from the first and second reporter polypeptides are distinguishable. In some embodiments, a reporter polypeptide is an enzyme (e.g., a peroxidase, alkaline phosphatase, galactosidase, etc.) that produces a detectable signal in the presence of an appropriate substrate. In some embodiments, a reporter polypeptide is a fluorescent protein (e.g., blue fluorescent protein, green fluorescent protein (GFP), red fluorescent protein (RFP), cyan fluorescent protein (CFP), yellow fluorescent protein (YFP), far-red fluorescent protein, Cerulean, enhanced GFP (EGFP), mEGFP, Venus, mApple, mCherry, mRaspberry, mStrawberry, mTangerine, TagRFP, mRuby, mRuby2, mPlum, dsRed, PA-GFP, tdTomato, enhanced YFP (EYFP), Citrine, SYFP2, TagYFP, mOrange, mOrange2, mKOk, mKO2, Clover, Emerald, mPlum, HcRed-Tandem, mKate2, mNeptune, NirFP, and/or any derivative thereof). Any fluorescent protein can be used as a reporter polypeptide; such proteins will be known to one of ordinary skill in the art.

One exemplary, but non-limiting, fluorescent protein is mApple (see FIG. 1). The mApple coding DNA sequence, when inserted into the nef locus, can for example be (nef sequence is underlined):

```
                                          (SEQ ID NO: 19)
ATGGTGAGCAAGGGCGAGGAGAATAACATGGCCATCATCAAGGAGTTCAT

GCGCTTCAAGGTGCACATGGAGGGCTCCGTGAACGGCCACGAGTTCGAGA

TCGAGGGCGAGGGCGAGGGCCGCCCCTACGAGGCCTTTCAGACCGCTAAG

CTGAAGGTGACCAAGGGTGGCCCCCTGCCCTTCGCCTGGGACATCCTGTC

CCCTCAGTTCATGTACGGCTCCAAGGTCTACATTAAGCACCCAGCCGACA

TCCCCGACTACTTCAAGCTGTCCTTCCCCGAGGGCTTCAGGTGGGAGCGC

GTGATGAACTTCGAGGACGGCGGCATTATTCACGTTAACCAGGACTCCTC

CCTGCAGGACGGCGTGTTCATCTACAAGGTGAAGCTGCGCGGCACCAACT

TCCCCTCCGACGGCCCCGTAATGCAGAAGAAGACCATGGGCTGGGAGGCC

TCCGAGGAGCGGATGTACCCCGAGGACGGCGCCCTGAAGAGCGAGATCAA

GAAGAGGCTGAAGCTGAAGGACGGCGGCCACTACGCCGCCGAGGTCAAGA

CCACCTACAAGGCCAAGAAGCCCGTGCAGCTGCCCGGCGCCTACATCGTC

GACATCAAGTTGGACATCGTGTCCCACAACGAGGACTACACCATCGTGGA

ACAGTACGAACGCGCCGAGGGCCGCCACTCCACCGGCGGCATGGACGAGC

TGTACAAGTAA.
```

The mApple protein sequence, when inserted into the nef locus, can for example be (nef sequence is underlined):

```
                                          (SEQ ID NO: 18)
MVSKGEENNMAIIKEFMRFKVHMEGSVNGHEFEIEGEGEGRPYEAFQTAK

LKVTKGGPLPFAWDILSPQFMYGSKVYIKHPADIPDYFKLSFPEGFRWER

VMNFEDGGIIHVNQDSSLQDGVFIYKVKLRGTNFPSDGPVMQKKTMGWEA

SEERMYPEDGALKSEIKKRLKLKDGGHYAAEVKTTYKAKKPVQLPGAYIV

DIKLDIVSHNEDYTIVEQYERAEGRHSTGGMDELYK
```

One exemplary, but non-limiting, fluorescent protein is EGFP (see FIG. 1). The EGFP coding DNA sequence, when inserted into the nef locus, can for example be (nef sequence is underlined):

```
                                            (SEQ ID NO: 22)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCCACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA.
```

The EGFP protein sequence, when inserted into the nef locus, can for example be (nef sequence is underlined):

```
                                            (SEQ ID NO: 21)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGHILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK
```

One exemplary, but non-limiting, fluorescent protein is mCherry (see FIG. 1). The mCherry coding DNA sequence can be:

```
                                            (SEQ ID NO: 28)
ATGGTGAGCAAGGGCGAGGAGGATAACATGGCCATCATCAAGGAGTTCAT

GCGCTTCAAGGTGCACATGGAGGGCTCCGTGAACGGCCACGAGTTCGAGA

TCGAGGGCGAGGGCGAGGGCCGCCCCTACGAGGGCACCCAGACCGCCAAG

CTGAAGGTGACCAAGGGTGGCCCCCTGCCCTTCGCCTGGGACATCCTGTC

CCCTCAGTTCATGTACGGCTCCAAGGCCTACGTGAAGCACCCCGCCGACA

TCCCCGACTACTTGAAGCTGTCCTTCCCCGAGGGCTTCAAGTGGGAGCGC

GTGATGAACTTCGAGGACGGCGGCGTGGTGACCGTGACCCAGGACTCCTC

CCTGCAGGACGGCGAGTTCATCTACAAGGTGAAGCTGCGCGGCACCAACT

TCCCCCTCCGACGGCCCCGTAATGCAGAAGAAGACCATGGGCTGGGAGGCC

TCCTCCGAGCGGATGTACCCCGAGGACGGCGCCCTGAAGGGCGAGATCAA

GCAGAGGCTGAAGCTGAAGGACGGCGGCCACTACGACGCTGAGGTCAAGA

CCACCTACAAGGCCAAGAAGCCCGTGCAGCTGCCCGGCGCCTACAACGTC

AACATCAAGTTGGACATCACCTCCCACAACGAGGACTACACCATCGTGGA

ACAGTACGAACGCGCCGAGGGCCGCCACTCCACCGGCGGCATGGACGAGC

TGTACAAGTAA.
```

The mCherry protein sequence can be (nef sequence is underlined):

```
                                            (SEQ ID NO: 27)
MVSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWER

VMNFEDGGVVTVTQDSSLQDGEFIYKVKLRGTNFPSDGPVMQKKTMGWEA

SSERMYPEDGALKGEIKQRLKLKDGGHYDAEVKTTYKAKKPVQLPGAYNV

NIKLDITSHNEDYTIVEQYERAEGRHSTGGMDELYK.
```

One exemplary, but non-limiting, fluorescent protein is mKO2. The mKO2 coding DNA sequence can be the nucleic acid sequence represented by positions 10215 to 10874 of SEQ ID NO:43. In some instances, the mKO2 coding DNA sequence can be:

```
                                            (SEQ ID NO: 45)
ATGGTGAGTGTGATTAAACCAGAGATGAAGATGAGGTACTACATGGACGG

CTCCGTCAATGGGCATGAGTTCACAATTGAAGGTGAAGGCACAGGCAGAC

CTTACGAGGGACATCAAGAGATGACACTACGCGTCACAATGGCCGAGGGC

GGGCCAATGCCTTTCGCGTTTGACTTAGTGTCACACGTGTTCTGTTACGG

CCACAGAGTATTTACTAAATATCCAGAAGAGATACCAGACTATTTCAAAC

AAGCATTTCCTGAAGGCCTGTCATGGGAAAGGTCGTTGGAGTTCGAAGAT

GGTGGGTCCGCTTCAGTCAGTGCGCATATAAGCCTTAGAGGAAACACCTT

CTACCACAAATCCAAATTTACTGGGGTTAACTTTCCTGCCGATGGTCCTA

TCATGCAAAACCAAAGTGTTGATTGGGAGCCATCAACCGAGAAAATTACT

GCCAGCGACGGAGTTCTGAAGGGTGATGTTACGATGTACCTAAAACTTGA

AGGAGGCGGCAATCACAAATGCCAAATGAAGACTACTTACAAGGCGGCAA

AAGAGATTCTTGAAATGCCAGGAGACCATTACATCGGCCATCGCCTCGTC

AGGAAAACCGAAGGCAACATTACTGAGCAGGTAGAAGATGCAGTAGCTCA

TTCCTAA.
```

In some instances, the nucleic acid sequence coding for a fluorescent protein used as a reporter polypeptide may be a codon optimized or codon switched version of the coding sequence of the fluorescent protein. Codon optimization or codon switching alters the nucleic acid sequence coding for the fluorescent protein such that the fluorescent protein is more efficiently expressed or more efficiently translated. A codon optimized or codon switched nucleic acid encoding for a fluorescent protein contains one or more altered codons relative to the wild-type or reference version of the nucleic acid encoding for the fluorescent protein. The number of switched codons will vary depending on a number of factors including, e.g., the wild-type or reference sequence encoding for the fluorescent protein, the reason for codon optimization or codon switching, the organism in which the fluorescent protein will ultimately be expressed, the desired level of codon optimization or switching, etc. Accordingly, the sequence identity shared between a codon optimized or codon switched version of a nucleic acid encoding a fluorescent protein and the particular fluorescent protein nucleic acid sequence from which it was derived will vary and may range from, e.g., 99.9% to 33.3% shared sequence identity, including but not limited to, e.g., 99.9% to 50%, 99.9% to 55%, 99.9% to 60%, 99.9% to 65%, 99.9% to 70%, 99.9% to 75%, 99.9% to 80%, 99.9% to 85%, 99.9% to 90%, 99.9% to 95%, 99.9% to 96%, 99.9% to 97%, 99.9% to 98%, 99.9% to 99%, 95% to 50%, 95% to 55%, 95% to 60%, 95% to 65%, 95% to 70%, 95% to 75%, 95% to 80%, 95% to 85%, 95% to 90%, 90% to 50%, 90% to 55%, 90% to 60%, 90% to 65%, 90% to 70%, 90% to 75%, 90% to 80%, 90% to 85%, 85% to 50%, 85% to 55%, 85% to 60%, 85% to 65%, 85% to 70%, 85% to 75%, 85% to 80%, 80% to 50%, 80% to 55%, 80% to 60%, 80% to 65%, 80% to 70%, 80% to 75%, 75% to 50%, 75% to 55%, 75% to 60%, 75% to 65%, 75% to 70%, etc. For example, the number of nucleotide substitutions present in a codon optimized or codon switched nucleic acid relative to the nucleic acid sequence encoding the fluorescent protein from which it was derived may vary and may range from, e.g., 1 to 200 nucleotide substitutions, including, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200. In some instances, a codon optimized or codon switched nucleic acid encoding for a fluorescent protein encodes the same or essentially the same amino acid sequence as the wild-type or reference version of the nucleic acid encoding for the fluorescent protein. In some instances, a codon optimized or codon switched nucleic acid encoding for a fluorescent protein encodes a different amino acid sequence as compared to the wild-type or reference version of the nucleic acid encoding for the fluorescent protein, including one or more amino acid substitutions, insertions, or deletions.

In certain instances, codon optimization or codon switching of a nucleic acid encoding a fluorescent protein is performed to increase the use of codons within the nucleic acid that are preferred codons for a particular organism or cell type, e.g., the organism or cell type in which the codon optimized or codon switched nucleic acid will ultimately be expressed. A preferred codon is a codon that appears at an increased frequency in a particular organism relative to codons that are synonymous, i.e. code for the same amino acid, as the preferred codon. A nucleic acid encoding for a fluorescent protein may be codon optimized or codon switched for expression in any organism or cell derived from such organisms, including but not limited to, e.g., mammals, primates, rodents, human, monkey, dog, cat, rabbit, rat, mouse, etc. Codon usage preference or codon usage bias for various organisms is known in the art and available, e.g., as codon usage tables or and codon usage databases, for use in codon optimization or codon switching (see e.g., "The Genetic Codes" at NCBI, available online at www(dot)ncbi (dot)nlm(dot)nih(dot)gov/Taxonomy/Utils/wprintgc(dot) cgi?mode=c#SG1 or "The Codon Usage Database" available online at www(dot)kazusa(dot)or(dot)jp/codon/).

One exemplary, but non-limiting, codon switched fluorescent protein is codon switched EGFP (csGFP). The csGFP coding DNA sequence can be:

(SEQ ID NO: 42)
ATGGTCTCCAAAGGGGAAGAGCTGTTCACCGGCGTGGTGCCCATCCTGGT

CGAGCTGGATGGGGATGTGAATGGGCATAAATTTAGCGTGTCCGGGGAAG

GGGAAGGGGATGCCACCTACGGCAAGCTGACCCTGAAGTTCATCTGCACC

ACCGGCAAGCTCCCTGTCCCTTGGCCCACCCTCGTGACCACCCTGACTTA

TGGCGTGCAGTGCTTCAGCCGCTACCCTGACCATATGAAACAGCACGATT

TCTTCAAGTCCGCCATGCCTGAGGGGTATGTGCAGGAACGGACTATCTTT

TTCAAAGACGATGGGAATTATAAGACCCGGGCCGAAGTCAAGTTCGAGGG

CGACACACTCGTGAACCGCATCGAACTCAAAGGGATTGATTTTAAGGAGG

ATGGGAATATTCTGGGGCACAAACTGGAGTACAACTACAACAGCCACAAC

GTCTATATCATGGCCGACAAGCAGAAGAACGGCATTAAAGTGAACTTCAA

GATCCGCCACAACATCGAAGATGGCAGCGTCCAGCTCGCCGATCATTATC

AACAGAACACCCCCATCGGCGACGGGCCTGTCCTCCTCCCTGATAACCAC

TACCTGAGCACCCAGTCCGCCCTGAGCAAAGACCCTAATGAAAAGCGCGA

TCACATGGTCCTGCTGGAGTTCGTGACAGCTGCTGGCATCACTCTGGGGA

TGGATGAACTCTATAAA.

In some embodiments, the presence of the reporter polypeptide itself acts as a signal. As one non-limiting example, the presence of a reporter polypeptide can be detected for example, using an antibody that specifically binds to the reporter polypeptide, e.g., to an epitope of the reporter polypeptide, to a fused epitope tag, etc.

Transactivator Protein (Tat)

A subject recombinant immunodeficiency virus (or a subject recombinant nucleic acid) is transcription competent, and, in some embodiments, includes a nucleotide sequence encoding a fully functional transactivator protein (Tat) as well as a transcriptional activation response region (TAR). The TAR, which is part of the long terminal repeat (LTR), is bound by Tat protein during transcription activation. In some embodiments, the encoded Tat protein and the TAR are wild-type. In other embodiments, the encoded Tat protein and/or the TAR include one or more amino acid or nucleotide sequence changes compared to the wild-type, but remain fully functional, e.g., Tat binds to TAR, and Tat-dependent transcription occurs when the subject cell is contacted with an activating agent.

In some embodiments, a subject latent transcription-competent immunodeficiency virus (or a subject recombinant nucleic acid) is not replication competent. In many of these embodiments, a portion or the entire nucleotide sequence that encodes the envelope protein in the native immunodeficiency virus is deleted (e.g., not included in the vector), and the immunodeficiency virus cannot be packaged without a helper virus vector. Vectors that do not encode an immunodeficiency virus envelope protein are used in many embodiments because of the ease of cloning and elimination of toxicity associated with the envelope protein. In these embodiments, the latent transcription-competent immunodeficiency virus (or latent transcription-competent immunodeficiency virus-based retroviral vector) does not form infectious virions when reactivated.

Where the immunodeficiency virus is recombinant and is not replication competent, viral particles are generated using a helper virus which provides the viral proteins that are not encoded by the recombinant immunodeficiency virus. Those skilled in the art are familiar with helper virus constructs and packaging cell lines that are used to package viral constructs (recombinant virus) that lacks coding sequences for one or more viral proteins, e.g., gag and env, that are required for packaging.

In some embodiments, the latent immunodeficiency virus in the subject cells is replication competent, e.g., the latent immunodeficiency virus, when reactivated, is transcribed, viral proteins are translated, and the resultant viral genome can replicate in a permissive cell. Whether the latent immunodeficiency virus is replication competent can be determined using known methods.

Recombinant Virions

The present disclosure further provides a recombinant virion that comprises a subject recombinant nucleic acid. Methods of packaging nucleic acid into a virion will be known by one of ordinary skill in the art and any convenient method may be used.

In some embodiments, the latent immunodeficiency virus in a cell forms infectious virions when activated, e.g., a subject recombinant nucleic acid, when activated, is transcribed, viral proteins are translated, and infectious virions are formed. Whether an immunodeficiency virus forms infectious virus when activated can be determined by activating a latent immunodeficiency virus, and determining infectivity of culture supernatant on permissive cells. Any known method can be used. As one non-limiting example, a subject cell containing a latent HIV is reactivated, and culture supernatant collected. The presence and/or number of infectious particles are determined by infecting Jurkat cells with the culture supernatant.

Genetically Modified Cells

The present disclosure further provides a cell that comprises a subject recombinant nucleic acid, and methods for producing such a cell. A cell comprising a subject recombinant nucleic acid can be considered a genetically modified cell (as defined above). Thus, a cell that comprises a subject recombinant nucleic acid can be referred to as a cell genetically modified with a subject recombinant nucleic acid. In some embodiments, a subject cell (i.e., a subject genetically modified cell) harbors a subject recombinant nucleic acid that is integrated into the cell's genome. In some cases, a subject cell is in vitro. In some cases, a subject cell is purified, e.g., a subject cell, when present in a population of cells, constitutes at least 50%, at least 60%, at least 70%, at least 80%, at least 90%, at least 95%, at least 98%, or more than 98%, of the cell population.

Examples of suitable cells include, but are not limited to various types of T cells. Suitable T cell lines and T cell-derived lines include, but are not limited to: Jurkat T cells; A301; and SupT1. A301 and SupT1 can be infected if the receptors and co-receptors expressed are compatible with the viral envelope of choice (e.g., a dual-tropic HIV gp160 derived from a patient isolate such as clone 92HT593.1 (Gao et al., 1996)).

Any of a variety of cells can comprise a subject recombinant nucleic acid integrated into the genome of the cell. In some embodiments, the cell is an immortalized cell. In other embodiments, the cell is a primary cell culture and is not immortalized. In some embodiments, the cell is a T cell or a T cell line. In some embodiments, the cell is a T cell or an immortalized T cell line that is permissive for an immunodeficiency virus, e.g., can be infected by an immunodeficiency virus, e.g., the T cell or immortalized T cell line expresses on its cell surface a CD4 receptor and a co-receptor (e.g., CXCR4 or CCR5).

Suitable immortalized T cell lines include, but are not limited to, Jurkat; MOLT-16; MOLT-17; MOLT-3; MOLT-4; Karpas-299; HuT78; HSB-2; CCRF-CEM; SupT1; H9; and the like. Such cell lines are publicly available, e.g., from the American Type Culture Collection.

In some embodiments, the cell is a primary T cell. Primary cultures of T cells can be obtained using standard methods. For example, human peripheral blood mononuclear cells (PBMC) are removed from a human donor, and T lymphocytes present in the PBMCs are separated from other lymphoid cells by any known method, including, but not limited to Ficoll-Hypaque cell separation. The cells can then be further subjected to cell sorting on the basis of cell surface expression of CD4 and CD3 molecules, e.g., using a fluorescence activated cell sorter and labeled antibody specific for CD4 and for CD3. The cells are then stimulated in the presence of PHA and grown continuously in the presence of low concentrations of recombinant IL-2, according to standard protocols.

In some embodiments, a suitable cell is an isolated clonal cell line. In some embodiments, a suitable cell is a member of a homogeneous population of cells (e.g., a population of cloned cells from a single cloned cell line). The immunodeficiency virus need not be integrated at the same genomic site in each cell of a population, and to that extent, the population can be considered heterogeneous, even though the cells used to make the population are from a single cell line.

In some embodiments, a subject recombinant nucleic acid is integrated into the genome of a cell. In some embodiments, the latent immunodeficiency virus is integrated in the genome at or near an alphoid repeat (e.g., adjacent to, or within an alphoid repeat, or within from about 10 base pairs (bp) to about 50 bp, from about 50 bp to about 100 bp, from about 100 bp to about 500 bp, from about 500 bp to about 1 kilobase pairs (kb), from about 1 kb to about 5 kb, or from about 5 kb to about 10 kb of an alphoid repeat). Alphoid repeats are approximately 171 base-pair repeats and are the smallest subunit of the alpha satellite, the major component of centromeres. Alphoid repeats are known in the art and the sequences of numerous centromeric alphoid repeats are publicly available, e.g., GenBank Accession Nos. AF153368; D29750; X03113; X03115; X66291; and M16101.

The recombinant immunodeficiency virus (a subject recombinant nucleic acid) can be introduced into cells using any known means, including, but not limited to, electroporation of nucleic acid (e.g., DNA and/or RNA), calcium phosphate precipitation, infection (where the recombinant immunodeficiency virus is packaged into a viral particle, e.g., a virion), and the like. RNA can be in vitro transcribed, and can be produced using any convenient technique. Techniques for in vitro transcription are known to one of ordinary skill in the art. A subject recombinant nucleic acid (in the form of RNA or DNA) can then be inserted into the cell using any convenient technique for introducing foreign nucleic acid into a cell (including viral infection).

It will be appreciated by one of ordinary skill in the art that an integrase (e.g., encoded for by the nucleic acid, present in the virion, or otherwise present in the cell) will be present to allow for integration and reverse transcriptase (e.g., encoded for by the nucleic acid, present in the virion, or otherwise present in the cell) will be present when the recombinant nucleic acid is RNA, to allow for reverse transcription of the RNA into DNA that can integrate into the cell genome.

The recombinant immunodeficiency virus can be contacted with a cell population at a low multiplicity of infection (MOI) to reduce the likelihood that more than one recombinant virus enters a given cell. A suitable MOI is from about 0.01 to about 0.05, or from about 0.05 to about 0.1.

Identifying, Isolating, and Purifying Latently Infected Cells

The present disclosure further provides a population of isolated and/or purified latently infected cells, and methods for identifying, isolating, and/or purifying a cell (and/or a population of cells) that is latently infected with an immunodeficiency virus.

Subject latently infected cells can harbor a genomically integrated subject recombinant nucleic acid in which the viral promoter is transcriptionally silent. For example, where a first reporter polypeptide is encoded by a nucleotide sequence that is operably linked to an immunodeficiency virus promoter and is translated as an early gene, production of the first detectable signal produced by the first reporter polypeptide (i.e., the cell is positive for the first reporter polypeptide) indicates that the genomically integrated recombinant virus is active (i.e., is not latent), and is therefore not transcriptionally silent. However, when the second detectable signal (produced by the second reporter polypeptide) is produced and the first detectable signal is not produced (e.g., not produced in substantial amounts; not produced in a detectable amount), the viral promoter is determined to be transcriptionally silent and the cell is determined to be a latently infected cell.

A subject method of isolating a latently infected cell generally involves introducing into a population of cells a subject recombinant nucleic acid; and selecting a cell that is positive for the second detectable signal and is negative for the first detectable signal. In some embodiments, the method further comprises, prior to selecting, contacting the population of cells with an agent that activates HIV transcription. In doing so, many cells of the cell population are expected to become active and therefore are expected to become positive for both the first and second reporter polypeptide. However, some cells are likely to remain negative for the first reporter polypeptide and positive for the second reporter polypeptide, and such cells are selected as latent cells.

In some embodiments, the selecting step comprises selecting a population of cells that are positive for the second detectable signal and are negative for the first detectable signal. In some such embodiments, the method further comprises a verification step, to verify that the selected cells are able to be activated (i.e., to verify that cells of the selected population of cells are latent and are transcription competent). Accordingly, such methods further comprise contacting the selected cells with an agent that activates HIV transcription; and measuring the level of the first detectable signal in at least two cells of the contacted cell population. When cells of the cell population are transcription competent, then at least one cell of the selected cells will be positive for the first reporter polypeptide after contact with the agent that activates HIV transcription.

Detection of a reporter polypeptide is carried out using a method suitable to the particular produced signal. For example, where the reporter polypeptide is a fluorescent protein, fluorescence is detected; where the reporter polypeptide is a luminescent protein, luminescence is detected. In some embodiments, a reporter polypeptide is an enzyme that aids in the production of a fluorescent or luminescence signal in the presence of an appropriate substrate. Such methods are well known to those skilled in the art.

In some embodiments, a subject reporter polypeptide is a fluorescent protein, and detection of the detectable signal is by flow cytometry, using a fluorescence activated cell sorter (FACS). In many embodiments, the selection step involves selecting a population of cells that (in some cases, under basal in vitro culture conditions) is single-positive, exhibiting signal (e.g., fluorescence) of the second reporter polypeptide ("positive for the second reporter polypeptide"), but not exhibiting signal (e.g., fluorescence) of the first reporter polypeptide ("negative for" the first reporter polypeptide).

It will be understood by those of skill in the art that the stated measured levels of fluorescence (or any detectable signal) reflect detectable amounts of the detectable signal. A cell that is negative for a reporter polypeptide (the level of reporter polypeptide is not detectably different from a matched control) may still express minor amounts of the reporter polypeptide and may still therefore exhibit detectable levels of the detectable signal. And while it is commonplace in the art to refer to cells as "positive" or "negative" for a particular reporter, actual expression levels are quantitative traits. For example, the number of molecules present in two different cells can vary by several logs, yet both cells can still be characterized as "positive."

The signal intensity (e.g., fluorescence intensity) of cells can be monitored by flow cytometry, where lasers detect the quantitative levels of fluorescence signal (which is proportional to the amount of a fluorescent reporter polypeptide). Flow cytometry, or FACS, can also be used to separate cell populations based on the intensity of detected signal, as well as other parameters such as cell size and light scatter. Although the absolute level of signal may differ from experiment to experiment, the data can be normalized to a control.

In the subject methods, cells that are measured to be positive for both the first and second reporter polypeptides are actively infected cells while cells that are measured to be positive for the second reporter polypeptide but negative for the first reporter polypeptide are latently infected cells.

Any selected populations of cells can be subject to cloning, e.g., limiting dilution cloning. Cells are plated in individual wells of a multi-well plate at a density of one cell per well. Any isolated cell and be subject to culture conditions that allow for cell proliferation.

In some embodiments, the cells are contacted with a reactivating agent. Under certain cell culture conditions, the latent immunodeficiency virus can be reactivated, e.g., the latent recombinant nucleic acid becomes transcriptionally activated. In many embodiments, reactivation of the latent virus (or recombinant nucleic acid) does not require a host cell factor. Culture conditions that result in reactivation of a latent immunodeficiency virus include contacting the cell for a suitable period of time with an effective amount of one or more reactivating agents. Agents that reactivate a latent immunodeficiency virus in a subject cell are termed "reactivating agents" and include, but are not limited to, activators of NF-κB, including, but not limited to, phytohemagglutinin (PHA), phorbol esters, e.g., tetradecanoyl phorbol acetate (TPA), and TNFα; exposure to an antigen for which a cell surface T-cell receptor is specific; an agent that cross-links cell-surface T-cell receptor, e.g., anti-CD3 antibody; inhibitors of histone deacetylase, e.g., trichostatin A, sodium butyrate, suberoylanilide hydroxamic acid (SAHA), and trapoxin; and a protein kinase C (PKC) activator, e.g., prostratin.

An effective amount of a reactivating agent is an amount effective to achieve transcriptional activation of the latent immunodeficiency virus. Whether transcription is reactivated can be determined using any known method, including, but not limited to, detecting production of a subject first reporter polypeptide (or detecting a first detectable signal produced by a subject first reporter polypeptide), and/or detecting production of a viral protein under transcriptional control of an immunodeficiency promoter.

Exemplary of reactivating agents are as follows: from about 5 nM to about 10 nM TPA; from about 0.5 µM to about 15 µM (e.g., 5 µM) prostratin; from about 0.5 µM to about 10 µM (e.g., 2.5 µM) SAHA; from about 5 ng/ml to about 20 ng/ml (e.g., 10 ng/ml) TNF-α; from about 2.5 µg/ml to about 10 µg/ml PHA; from about 2.5 µg/ml to about 10 µg/ml anti-CD3 antibody; and from about 200 nM to about 800 nM TSA. Non-limiting examples of effective amounts of exemplary reactivating agents are as follows: 10 nM TPA; 10 ng/ml TNF-α; 5 µg/ml PHA; 5 µg/ml anti-CD3 antibody; and 400 nM TSA. Threshold and sub-threshold amounts for activation of immunodeficiency virus in cells (e.g., reactivation) will be known to one of ordinary skill in the art.

Suitable periods of time for contacting a cell with a reactivating agent are from about 0.5 hour to about 24 hours, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 20 hours, or from about 20 hours to about 24 hours. Contacting a cell with an effective amount of a reactivating agent is typically conducted under standard culture conditions of 37° C. and 5% $CO_2$.

Screening Methods

The present disclosure further provides a method of identifying a candidate agent that can reactivate an immunodeficiency virus (e.g., HIV). Because agents that reactivate an immunodeficiency virus can be used to treat an immunodeficiency virus infection (i.e., treat an individual harboring an immunodeficiency virus infection), a method of identifying a candidate agent for reactivating an immunodeficiency virus in an individual can also be considered a method of identifying a candidate agent for treating an immunodeficiency virus infection (e.g., an HIV infection).

The methods generally involve contacting a cell comprising a subject recombinant nucleic acid (e.g., a transcription-competent latent immunodeficiency virus, a transcription-competent recombinant immunodeficiency virus-based vector, etc.) with a test agent; and determining whether the latent immunodeficiency virus is activated. In some embodiments, the subject recombinant nucleic acid is integrated into the genome of the cell. A test agent that increases activation of a latent immunodeficiency virus, compared to a control in the absence of the test agent, is considered a candidate agent for reactivating latent immunodeficiency virus.

The present invention further provides screening methods for identifying an agent that blocks reactivation of latent immunodeficiency virus in response to a T cell activation signal. The methods generally involve contacting a subject cell that comprises a transcription-competent latent immunodeficiency virus (or a transcription-competent recombinant immunodeficiency virus-based vector) integrated into the genome of the cell with a test agent and an agent that activates T cells; and determining whether the latent immunodeficiency virus is activated.

The terms "candidate agent," "agent", "substance," "test agent," and "compound" are used interchangeably herein. Candidate agents encompass numerous chemical classes, and are generally synthetic, semi-synthetic, or naturally occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent is assessed for any cytotoxic activity it may exhibit toward control cells not infected with an immunodeficiency virus, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity toward control cells not infected with an immunodeficiency virus are considered suitable candidate agents.

Assays of the invention usually include one or more controls. Thus, a test sample includes a test agent, and a control sample has all the components of the test sample except for the test agent.

A variety of reagents may be included in the screening assay. These include reagents like salts, neutral proteins, e.g. albumin, detergents, etc., that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 37° C. and 40° C. Incubation periods are selected for optimum activity, but may also be optimized to facilitate rapid high-throughput screening. Typically between 0.1 and 1 hour will be sufficient.

In some embodiments, the subject method of identifying an agent that activates a latent human immunodeficiency virus involves contacting a latently infected cell with a test agent, which cell comprises a subject recombinant nucleic acid (in some cases genomically-integrated); measuring the amount of the first detectable signal; and determining the effect, if any, of the test agent on the amount of the first detectable signal. When an increase is measured in the amount of the first detectable signal in a cell contacted with the test agent relative to a cell not contacted with the test agent (which can be determined using a comparable cell that has not contacted the test agent; or can be determined prior to the contacting step), the test agent is determined to activate the latent immunodeficiency virus. In some cases, prior to contacting the cell with a test agent, the cell is isolated as a latently infected cell according to the methods described above.

In some embodiments, the subject method of identifying an agent that activates a latent human immunodeficiency virus involves contacting a population of cells (where the population includes at least two cells that are latently infected with a subject recombinant nucleic acid) with a test agent; measuring the amount of the first detectable signal in at least two cells of the contacted cell population; and determining the effect, if any, of the test agent on the fraction of cells that are positive for the first detectable signal. When an increase is measured in the fraction of cells that are positive for the first detectable signal (in the cell population contacted with the test agent relative to a comparable cell population not contacted with the test agent), the test agent is determined to activate the latent immunodeficiency virus. In some cases, the cell population, prior to contact with a test agent, is a population of cells isolated according to the methods described above.

In some embodiments, the subject method of identifying an agent that activates a latent immunodeficiency virus involves contacting a latently infected cell (and/or a latently infected cell population) with a test agent and an agent known to activate latent immunodeficiency virus (e.g., a sub-threshold level of an agent known to activate latent immunodeficiency virus when used at or above a threshold level). Such methods can be referred to as sensitized screen methods. As an illustration, refer to FIG. 3E in the Examples.

In some embodiments, the subject method for identifying an agent that blocks reactivation of latent immunodeficiency virus in response to a T cell activation signal involves contacting a subject cell with a test agent and a reactivating agent which cell comprises a subject recombinant nucleic acid (in some cases genomically-integrated); measuring the amount of the first detectable signal; and determining whether the latent immunodeficiency virus is activated (as above). A decrease in production of the first detectable signal, compared to a control lacking the test agent (but having the reactivating agent), indicates that the test agent blocks activation of the latent HIV. Suitable reactivating agents include those described above.

Utility

The subject recombinant nucleic acids, virions, cells, and methods are useful in research, screening, and therapeutic applications. Subject cells are useful as research tools for investigating the mechanism of immunodeficiency virus latency. The subject cells are also useful in screening methods for identifying agents that reactivate latent immunodeficiency virus, and agents that block reactivation of latent immunodeficiency virus, which methods are described above. Thus, the subject methods are useful in identifying agents that are useful in treatment methods.

Studies of latency are complicated by the fact that the detection of latent HIV-infected cells requires HIV activation, but HIV activation is cytotoxic. Thus, current cell models that involve enrichment of latently infected cells require prestimulation with specific compounds or cytokines to identify the infected population, and subsequent induction of a latent state. To the contrary, the subject compositions and methods facilitate detection and purification of live, latent-HIV-infected cells, without reactivation of the cells, overcoming the cytotoxic effect of HIV reactivation. A population of latently infected cells can be identified regardless of their responsiveness to the reactivation of cellular pathways, and thus this methodology more closely approximates the establishment of latent infection early in the viral life cycle prior to initiation of tat-dependent HIV transcription.

Isolated and/or purified populations of latently infected cells can be used, for example, in high-throughput assays while overcoming the clonal-derived biases of current assays. The subject compositions and methods allow for the identification and purification of live, latently infected cells and their separation from actively infected and uninfected cells, including human primary CDT cells. These cells contain the main constituents of the latent HIV reservoir, such as central and transitional memory $CD4^+$ T cells.

Examples 1-4 below demonstrate that purification of latently infected cells from a primary infected pool allows for the study of HIV latency independent of cell clonality, insertion sites in the genome, and reactivating stimuli. Because of this purification, the dynamic range of reactivation assays is increased. This permits the detection of novel compounds that reactivate latent HIV.

The subject compositions (e.g., recombinant nucleic acids, cells, virions, etc.) and methods, in some cases utilize a replication-deficient lentiviral system that is easily pseudotyped and packaged in a number of ways, which facilitates its use for the study of latent infection events in any cell population of interest. The subject compositions and methods can thus be used in different cell types and candidate reservoirs of the latent HIV pool.

As demonstrated in Examples 1-4 below, the subject compositions and methods were used to identified classes of clinically or experimentally used drugs, not typically associated with the biology of HIV latency, which produced significant reactivation of the provirus, such as drugs acting on neurotransmitter receptors or Tyr kinases. In flow cytometry assays of the sorted latent-cell population, some of the identified drugs showed a dose-dependent reactivation of latency; in combination with low doses of the current leads for latent HIV reactivation (e.g., SAHA, prostratin) certain drugs also revealed a synergistic effect. Thus, the identified drug combinations can be used in HIV reactivation methods.

Treatment Methods

The present disclosure provides compositions and methods for reactivating latent immunodeficiency virus in an immunodeficiency virus-infected cell; and methods of treating an individual having an immunodeficiency virus infection.

1) Methods of Reactivating Latent Immunodeficiency Virus

The present disclosure provides compositions and methods for reactivating latent immunodeficiency virus in an immunodeficiency virus-infected cell. In some cases, the methods generally involve administering to an individual in need thereof an agent that is effective to activate latent immunodeficiency virus. The active agent can be administered as part of a combination therapy with at least one anti-immunodeficiency virus therapeutic agent.

An effective amount of an active agent is an amount that reactivates latent HIV and reduces the reservoir of latent HIV in an individual by at least about 20%, at least about 30%, at least about 40%, at least about 50%, at least about 60%, at least about 70%, at least about 80%, or at least about 90%. A "reduction in the reservoir of latent HIV" (also referred to as "reservoir of latently infected cells") is a reduction in the number of cells in the individual that harbor a latent HIV infection. Whether the reservoir of latently infected cells is reduced can be determined using any known method, including the method described in Blankson et al. (2000) *J. Infect. Disease* 182(6):1636-1642.

Thus, the present disclosure provides a method of reducing the number of cells containing a latent human immunodeficiency virus in an individual. The methods generally involve administering to an individual in need thereof an active agent in an amount effective to activate latent immunodeficiency virus.

Suitable active agents include, but are not limited to, a Bruton's tyrosine kinase inhibitor (e.g., a quinone epoxide such as terreic acid); an adenosine reuptake inhibitor (e.g., dilazep); a reseveratrol analog (e.g., piceatannol); an epidermal growth factor receptor (EGFR) tyrosine kinase (TK) inhibitor (e.g., a selective EGFR TK inhibitor); a selective p38 mitogen-activated protein kinase (MAPK) inhibitor; an AMPA receptor blocker; a kainate receptor blocker; a selective phosphatidylinositol 3 (PI3) kinase inhibitor; a mGlu5 antagonist; a SERCA ATPase inhibitor; a calcium channel activator; a KCNQ channel blocker; a dopamine D3 receptor agonist; a 5HT1B antagonist; a 5-HT2 antagonist; a dihydrofolate reductase (DHFR) inhibitor; a selective GSK-3 inhibitor; a selective cdc25 phosphatase inhibitor; and a 5-,12-,15-lipoxygenase inhibitor. The following are exemplary compounds.

Terreic acid:

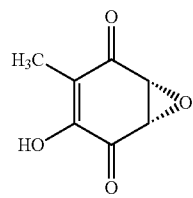

Dilazep:

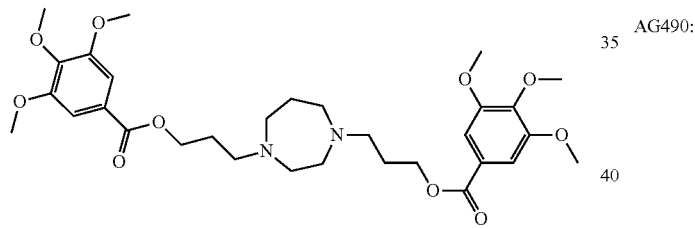

Piceatannol:

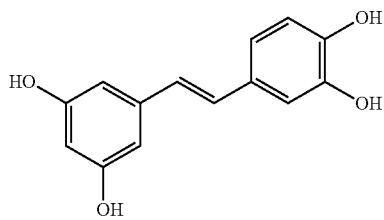

Suitable EGFR TK inhibitors include, e.g., AG555 (α-Cyano-(3,4-dihydroxy)-N-(3-phenylpropyl)cinnamide); AG18 ([(3,4-Dihydroxyphenyl)methylene]-propenedinitrile); AG99 ((E)-2-Cyano-3-(3,4-dihydroxyphenyl)-2-propenamide); tyrphostin B44; AG490; AG494 ((E)-2-Cyano-3-(3,4-dihydroxyphenyl)-N-phenyl-2-propenamide); and genistein. In some embodiments, the EGFR TK inhibitor is a selective EGFR TK inhibitor, e.g., the EGFR-TK inhibitor does not substantially inhibit any tyrosine kinase other than an EGFR-TK; for example, a selective EGFR-TK inhibitor does not substantially inhibit a platelet-derived growth factor receptor (PDGFR) TK. The following are exemplary compounds.

AG555:

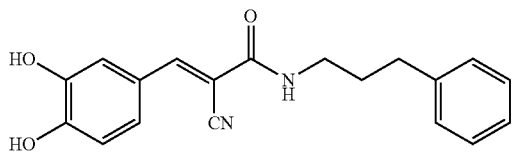

AG18:

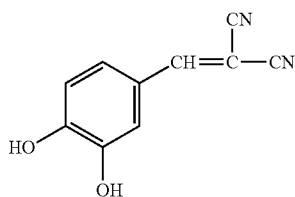

Tyrphostin B44:

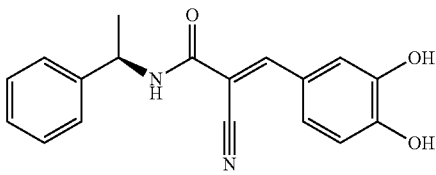

AG99:

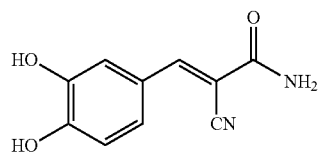

AG490:

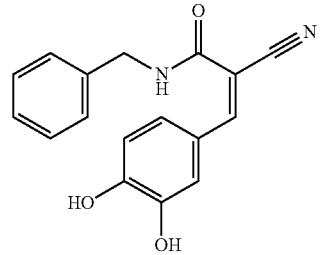

AG494:

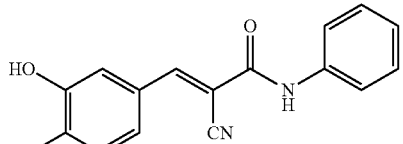

Genistein:

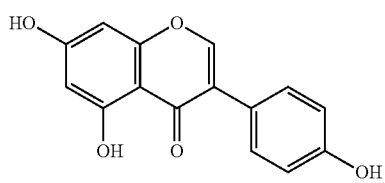

In some instances, the EGFR TK inhibitor is a tyrphostin compound as described in WO 1998/006391. In some instances, the EGFR TK inhibitor is a tyrphostin of the general formula:

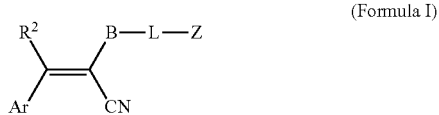

(Formula I)

wherein Ar is an aryl, a substituted aryl, a heteroaryl, or a substituted heteroaryl;

$R^2$ is H, an alkyl or a substituted alkyl; and

B is an optional spacer group;

L is an optional linker;

Z is an end group selected from the groups consisting of H, CN, a carboxylic acid, an acylamino, an aminoacyl, an acyl, an alkoxycarbonylamino, an aminocarbonylamino, an acyloxy, an aminosulfonyl, a sulfonylamino, an aryl, a substituted aryl, a heteroaryl, or a substituted heteroaryl, an alkyl or a substituted alkyl.

In certain embodiments, in the general formula, Z is an aryl, a substituted aryl, a heteroaryl, or a substituted heteroaryl.

In certain embodiments, $R^2$ is H. In certain embodiments, $R^2$ is an alkyl, e.g., a lower alkyl such as methyl.

In some embodiments, Ar is an aryl or a substituted aryl. In some embodiments, Ar is an heteroaryl or a substituted heteroaryl. In some instances, Ar is a 3,4-disubstituted aryl or heteroaryl group, where the aryl or heteroaryl group contains a 6-membered ring. In certain embodiments, Ar is a phenyl or a substituted phenyl. In some instances, Ar is a 3,4-disubstituted phenyl group. In certain instances, Ar is a 3,4-disubstituted phenyl group, where each substituent is independently selected from hydroxy, halogen, thiol, amino, a substituted amino, an alkyl, an alkyloxy, a substituted alkyloxy, an aryloxy, and a substituted aryloxy. In certain embodiments, Ar is a 3,4-disubstituted phenyl group, where each substituent is independently selected from hydroxy, an alkyloxy, and a substituted alkyloxy. In certain instances, Ar is a 3,4-dihydroxyphenyl group.

In some embodiments, B is a covalent bond or divalent functional group. In certain embodiments, B is selected from the group consisting of an acylamino, an aminoacyl, an acyl, an alkoxycarbonylamino, an aminocarbonylamino, an acyloxy, an aminosulfonyl and a sulfonylamino. In certain instances, B is selected from the group consisting of a covalent bond, —C(O)NR—, —C(O)NH—, —NRC(O)—, —NHC(O)—, —C(O)O—, —S(O)$_2$NR—, —S(O)$_2$NH—, —NRS(O)$_2$— and —NHS(O)$_2$—, wherein R is an alkyl or substituted alkyl. In certain embodiments, B is —C(O)NH—.

In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In certain cases, B is absent. In certain embodiments, L is absent. In certain embodiments, Z is CN.

In certain embodiments, B is —C(O)NR— or C(O)NH—, wherein R is an alkyl or a substituted alkyl; L is a covalent bond, an alkyl, a substituted alkyl, or a polyethylene glycol; and Z is H, an aryl, a substituted aryl, a heteroaryl, or a substituted heteroaryl. In certain instances, Z is a phenyl or a substituted phenyl. In certain cases, Z is phenyl.

In some cases, the EGFR TK inhibitor is a tyrphostin of the general formula:

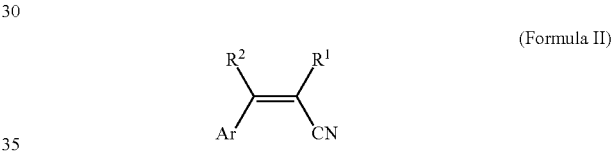

(Formula II)

wherein Ar is an aryl or a substituted aryl, a heteroaryl, or a substituted heteroaryl;

$R^2$ is H, an alkyl or a substituted alkyl; and $R^1$ is H, CN, a carboxylic acid, an acylamino, an aminoacyl, an acyl, an alkoxycarbonylamino, an aminocarbonylamino, an acyloxy, an aminosulfonyl, a sulfonylamino, an aryl, a substituted aryl, a heteroaryl, or a substituted heteroaryl, an alkyl or a substituted alkyl.

In some embodiments, Ar is an aryl or a substituted aryl. In some embodiments, Ar is an heteroaryl or a substituted heteroaryl. In some instances, Ar is a 3,4-disubstituted aryl or heteroaryl group, where the aryl or heteroaryl group contains a 6-membered ring. In certain embodiments, Ar is a phenyl or a substituted phenyl. In some instances, Ar is a 3,4-disubstituted phenyl group. In certain instances, Ar is a 3,4-disubstituted phenyl group, where each substituent is independently selected from hydroxy, halogen, thiol, amino, a substituted amino, an alkyl, an alkyloxy, a substituted alkyloxy, an aryloxy, and a substituted aryloxy. In certain embodiments, Ar is a 3,4-disubstituted phenyl group, where each substituent is independently selected from hydroxy, an alkyloxy, and a substituted alkyloxy. In certain instances, Ar is a 3,4-dihydroxyphenyl group.

In certain embodiments, $R^2$ is H. In certain embodiments, $R^2$ is an alkyl, e.g., a lower alkyl such as methyl.

In certain embodiments, $R^1$ is —CN. In certain embodiments, $R^1$ is —C(O)N(R)$R^3$ or C(O)NH$R^3$, wherein R is an alkyl or a substituted alkyl, such as a lower alkyl (e.g., methyl), and wherein $R^3$ is H, an alkyl, a substituted alkyl, an aryl, a substituted aryl, a heteroaryl, or a substituted heteroaryl. In certain instances, $R^3$ is phenyl, a substituted phenyl, or a substituted alkyl (e.g., a lower alkyl substituted with an aryl, a substituted aryl, a heteroaryl or a substituted heteroaryl). In certain instances, $R^3$ is phenyl, or a lower alkyl substituted with a phenyl. In certain embodiments, $R^3$ is phenyl, or —$(CH_2)_m$-Ph, wherein m is 1, 2, 3, 4, 5 or 6. In certain embodiments, $R^3$ is phenyl. In certain embodiments, $R^3$ is —$(CH_2)_m$-Ph, wherein m is 1, 2 or 3.

In some cases, the EGFR TK inhibitor is a tyrphostin of the formula:

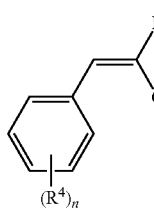

(Formula III)

wherein $R^1$ is H, CN, a carboxylic acid, an acylamino, an aminoacyl, an acyl, an alkoxycarbonylamino, an aminocarbonylamino, an acyloxy, an aminosulfonyl, a sulfonylamino, an aryl, a substituted aryl, a heteroaryl, or a substituted heteroaryl, an alkyl or a substituted alkyl; n is 0, 1, 2, 3 or 4; and each $R^4$ substituent is independently selected from hydroxy, halogen, thiol, amino, a substituted amino, an alkyl, an alkyloxy, a substituted alkyloxy, an aryloxy, and a substituted aryloxy.

In certain embodiments, $R^1$ is —CN. In certain embodiments, $R^1$ is —C(O)N(R)$R^3$ or C(O)NHR$^3$, wherein R is an alkyl or a substituted alkyl, such as a lower alkyl (e.g., methyl), and wherein $R^3$ is H, an alkyl, a substituted alkyl, an aryl, a substituted aryl, a heteroaryl, or a substituted heteroaryl. In certain instances, $R^3$ is phenyl, a substituted phenyl, or a substituted alkyl (e.g., a lower alkyl substituted with an aryl, a substituted aryl, a heteroaryl or a substituted heteroaryl). In certain instances, $R^3$ is phenyl, or a lower alkyl substituted with a phenyl. In certain embodiments, $R^3$ is phenyl, or —$(CH_2)_m$-Ph, wherein m is 1, 2, 3, 4, 5 or 6. In certain embodiments, $R^3$ is phenyl. In certain embodiments, $R^3$ is —$(CH_2)_m$-Ph, wherein m is 1, 2 or 3.

In certain embodiments, n is 2 and each $R^4$ is independently selected from hydroxy, halogen, thiol, amino, a substituted amino, an alkyl, an alkyloxy, a substituted alkyloxy, an aryloxy, and a substituted aryloxy. In certain embodiments, n is 2 and each $R^4$ is independently selected from hydroxy, an alkyloxy, and a substituted alkyloxy. In certain instances, each $R^4$ is hydroxy, e.g., hydroxy substituents located at the 3- and 4-positions of the phenyl ring.

In some cases, the EGFR TK inhibitor is a tyrphostin of the formula:

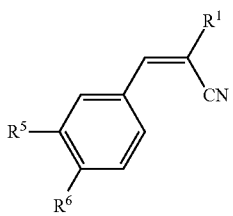

(Formula IV)

wherein $R^1$ is as defined above, and $R^5$ and $R^6$ are each independently from H, hydroxy, an alkyloxy, and a substituted alkyloxy. In certain embodiments, $R^5$ and $R^6$ are each hydroxy.

In some embodiments, an active agent is a selective p38 MAPK inhibitor. Suitable selective p38 MAPK inhibitors include compounds described in U.S. Pat. Nos. 6,509,361, 6,479,507, and U.S. Patent Publication No. 2002/0198214. Examples of suitable p38 MAPK inhibitors include, e.g., SB202190; SB203580; and the like. The following are exemplary compounds.

SB202190:

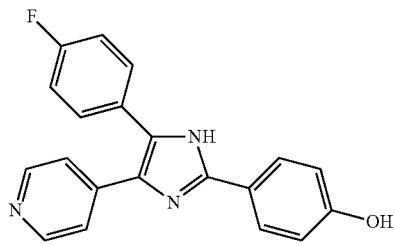

SB203580:

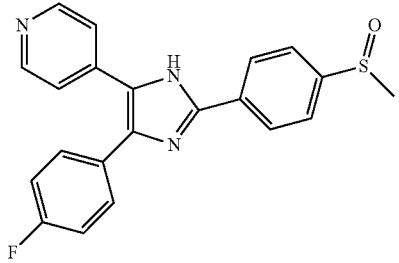

In some embodiments, an active agent is a p38 MAPK inhibitor described by the following formula:

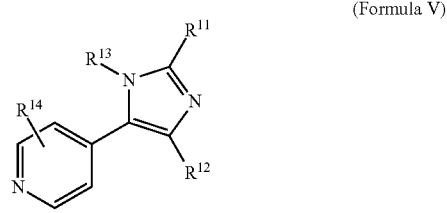

(Formula V)

wherein $R^{11}$ and $R^{12}$ are independently selected from an aryl, a substituted aryl, a heteroaryl, and a substituted heteroaryl;

$R^{13}$ is H, an alkyl or a substituted alkyl; and $R^{14}$ is H or one or more substituents.

In certain embodiments, $R^{14}$ is one or more substituents each independently selected from the group consisting of hydroxy, halogen, an alkyl, a substituted alkyl, an alkoxy, a substituted alkoxy, amino, a substituted amino, cyano, a carboxy, an acylamino, an aminoacyl, an acyl, an alkoxycarbonylamino, an aminocarbonylamino, an acyloxy, an aminosulfonyl, and a sulfonylamino. In certain embodiments, $R^{14}$ is hydroxy, halogen, an alkyl, a substituted alkyl, an alkoxy or a substituted alkoxy. In certain embodiments, $R^{14}$ is H.

In some embodiments, an active agent is a selective p38 MAPK inhibitor described by the following formula:

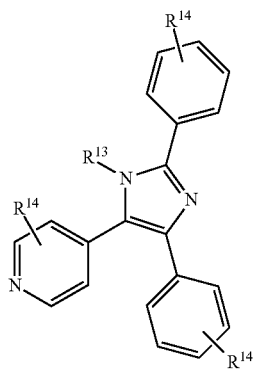

(Formula VI)

where $R^{13}$ and $R^{14}$ are as defined above.

In certain embodiments, $R^{13}$ is H.

In certain embodiments, each $R^{14}$ is independently H or one or more substituents each independently selected from the group consisting of hydroxy, halogen, an alkyl, a substituted alkyl, an alkoxy, a substituted alkoxy, amino, a substituted amino, cyano, a carboxy, an acylamino, an aminoacyl, an acyl, a sulfonyl, a sulfonyloxy an alkoxycarbonylamino, an aminocarbonylamino, an acyloxy, an aminosulfonyl, and a sulfonylamino. In certain embodiments each $R^{14}$ is independently H or one or more substituents each independently selected from the group consisting of hydroxy, a sulfonyl, halogen, an alkyl, a substituted alkyl, an alkoxy and a substituted alkoxy.

In some embodiments, an active agent is a p38 MAPK inhibitor described by the following formula:

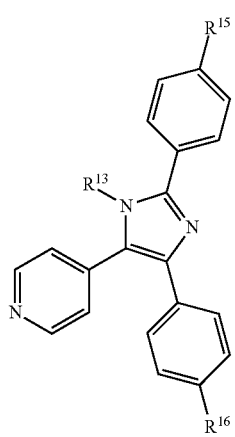

(Formula VII)

wherein $R^{15}$ and $R^{16}$ are independently H, hydroxy, halogen, a sulfonyl, an alkyl, a substituted alkyl, an alkoxy and a substituted alkoxy; and $R^{13}$ is H, an alkyl or a substituted alkyl.

In certain embodiments, $R^{15}$ is H, hydroxy, and alkoxy, a substituted alkoxy, —SO$_2$-alkyl, or —SO$_2$-substituted alkyl, and $R^{16}$ is H or a halogen. In certain embodiments, $R^{16}$ is fluoro.

In certain embodiments, R13 is H.

Other suitable active agents include, e.g.:

1) NBQX:

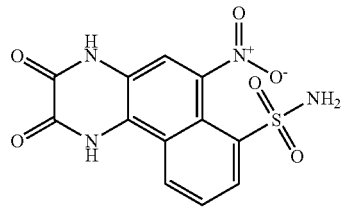

2) SIB1893 ((E)-2-methyl-6-(2-phenylethenyl)pyridine):

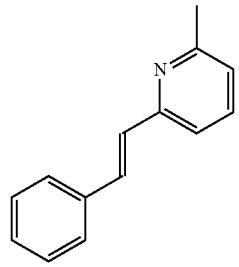

3) LY 204002:

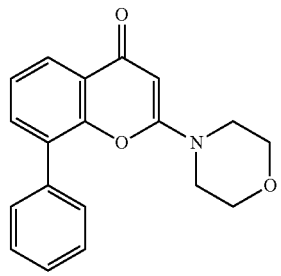

4) quercitin:

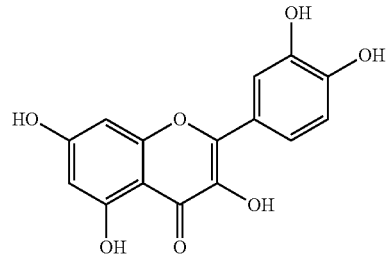

5) cyclopiazonic acid

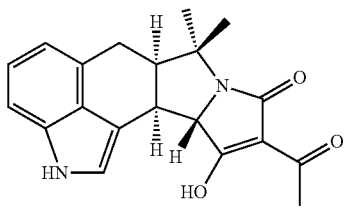

6) NSC 95397:

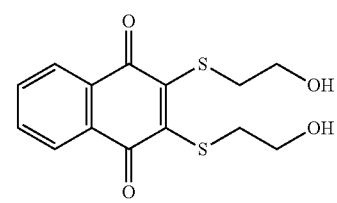

7) Bay K8644
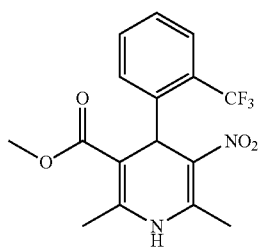
8) Linopirdine:
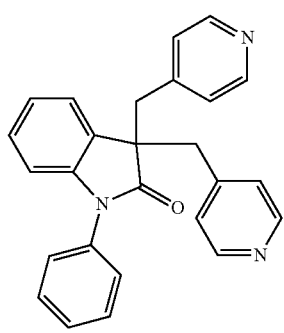
9) apomorphine:
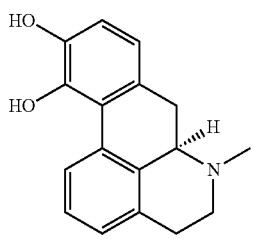
10) piribedil:
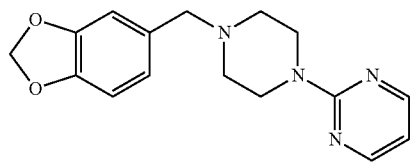
11) GR 55562:
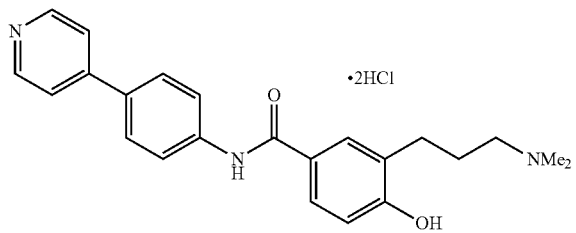
12) ritanserin:
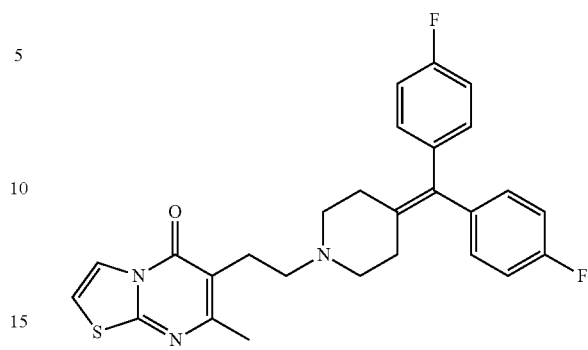
13) CI 898:
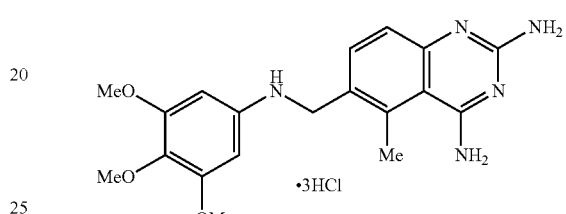
14) SB 216763:
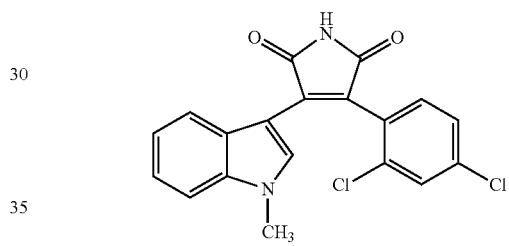
15) 2-TEDC (2-(1-thienyl)ethyl 3,4-dihydroxybenzylidenecyanoacetate):
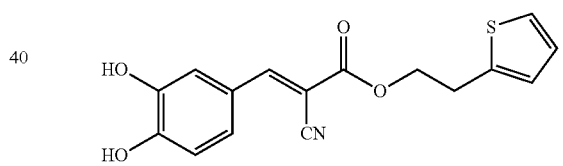
16) resveratrol:
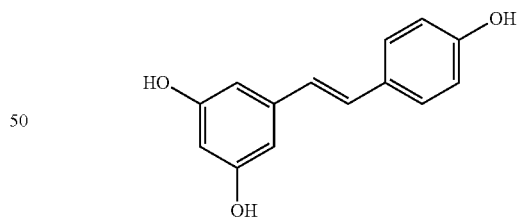
17) clozapine:
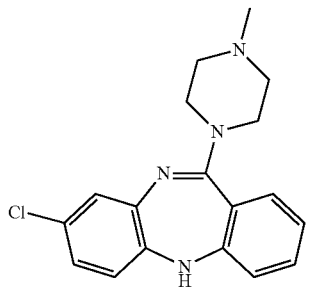

-continued 18) pterostilbene:

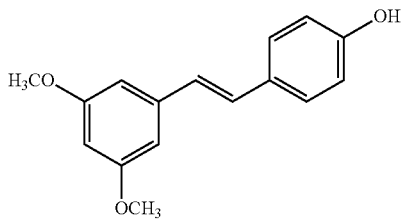

19) dipyridamol:

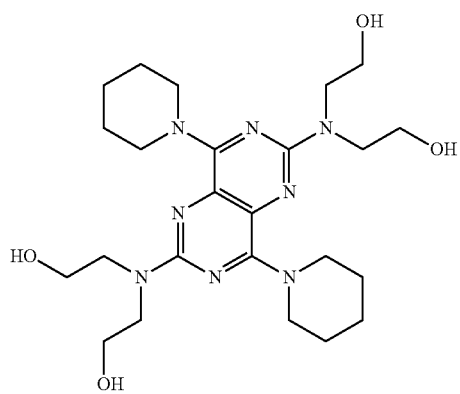

20) simvastin.

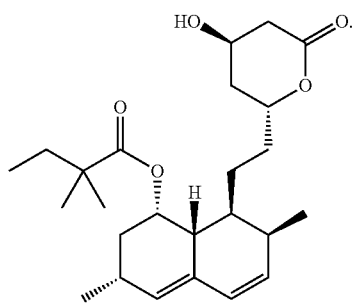

2) Methods of Treating an Immunodeficiency Virus Infection

The present disclosure provides methods of treating an immunodeficiency virus infection in an individual, the methods generally involving co-administering to the individual: a) an active agent, as described above, which active agent reactivates latent HIV; and b) an anti-HIV agent, i.e., an agent that inhibits an immunodeficiency virus function (e.g., an agent that specifically inhibits an immunodeficiency virus function). The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

Any of a variety of methods can be used to determine whether a treatment method is effective. For example, methods of determining whether the methods of the invention are effective in reducing immunodeficiency virus (e.g., HIV) viral load, and/or treating an immunodeficiency virus (e.g., HIV) infection, are any known test for indicia of immunodeficiency virus (e.g., HIV) infection, including, but not limited to, measuring viral load, e.g., by measuring the amount of immunodeficiency virus (e.g., HIV) in a biological sample, e.g., using a polymerase chain reaction (PCR) with primers specific for an immunodeficiency virus (e.g., HIV) polynucleotide sequence; detecting and/or measuring a polypeptide encoded by an immunodeficiency virus (e.g., HIV), e.g., p24, gp120, reverse transcriptase, using, e.g., an immunological assay such as an enzyme-linked immunosorbent assay (ELISA) with an antibody specific for the polypeptide; and measuring the CD4$^+$ T cell count in the individual.

In general, an active agent (e.g., an active agent that reactivates latent HIV; an agent that inhibits an immunodeficiency virus function) is prepared in a pharmaceutically acceptable composition(s) for delivery to a host. In the context of reducing immunodeficiency virus transcription, the terms "active agent," "drug," "agent" "therapeutic agent," and the like are used interchangeably herein to refer to an active agent that reactivates latent HIV or to an agent that inhibits an immunodeficiency virus function.

Pharmaceutically acceptable carriers preferred for use with active agents (and optionally one or more additional therapeutic agent) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (and optionally one or more additional therapeutic agent) may also be lyophilized using means well known in the art, for subsequent reconstitution and use according to the invention.

Formulations

An active agent is administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. For the purposes of the following description of formulations, "active agent" includes an active agent as described above, and optionally one or more additional therapeutic agent.

In a subject method, an active agent may be administered to the host using any convenient means capable of resulting in the desired degree of reduction of immunodeficiency virus transcription. Thus, an active agent can be incorporated into a variety of formulations for therapeutic administration. For example, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent is formulated as a gel, as a solution, or in some other form suitable for intravaginal administration. In a further exemplary embodiment, an active agent is formulated as a gel, as a solution, or in some other form suitable for rectal (e.g., intrarectal) administration.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered in an injectable composition. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration comprises an active agent formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration comprises an active agent formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range of an active agent is one which provides up to about 1 mg to about 1000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, or from about 500 mg to about 1000 mg of an active agent can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Where two different active agents are administered, a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to immunodeficiency virus (e.g., HIV) infection. In many embodiments, the hosts will be humans.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an immunodeficiency virus (e.g., an HIV) infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

A delivery system can be used to deliver an active agent(s). In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, an active agent is packaged for oral administration. For example, a packaging unit can include daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a delivery system can include an injection device. Exemplary, non-limiting drug delivery devices include injections devices, such as pen injectors, and needle/syringe devices. In some embodiments, the invention provides an injection delivery device that is pre-loaded with a formulation comprising an effective amount of an agent that reactivates latent immunodeficiency virus. For example, a subject delivery device comprises an injection device pre-loaded with a single dose of an agent that reactivates latent immunodeficiency virus. A suitable injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

An active agent(s) can be administered using a delivery system for vaginal or rectal delivery of an active agent to the vagina or rectum of an individual. The delivery system can include a device for insertion into the vagina or rectum. In some embodiments, the delivery system comprises an applicator for delivery of a formulation into the vagina or rectum; and a container that contains a formulation comprising an active agent. In these embodiments, the container (e.g., a tube) is adapted for delivering a formulation into the applicator. In other embodiments, the delivery system comprises a device that is inserted into the vagina or rectum, which device includes an active agent. For example, the device can be coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909. If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. The active agent is incorporated into a silicone matrix which is coated onto a cylindrical drug-free polyurethane sponge, as described in the literature.

Pessaries, tablets, and suppositories are other examples of drug delivery systems which can be used, e.g., in carrying out a method of the present disclosure. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10-100 μm and can be prepared from starch, gelatin, albumin, collagen, or dextran.

Another system is a container (e.g., a tube) comprising a subject formulation that is adapted for use with an applicator. The active agent is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Combination Therapy

In some embodiments, an agent that reactivates latent immunodeficiency virus is administered in combination therapy with one or more additional therapeutic agents. Suitable additional therapeutic agents include agents that inhibit one or more functions of an immunodeficiency virus; agents that treat or ameliorate a symptom of an immunodeficiency virus infection; agents that treat an infection that occurs secondary to an immunodeficiency virus infection; and the like.

Therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™) abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, an agent that reactivates latent immunodeficiency virus (where such agents are described above) is administered in combination therapy with two or more anti-HIV agents. For example, an agent that reactivates latent immunodeficiency virus can be administered in combination therapy with one, two, or three nucleoside reverse transcriptase inhibitors (e.g., Combivir, Epivir, Hivid, Retrovir, Videx, Zerit, Ziagen, etc.). An agent that reactivates latent immunodeficiency virus can be administered in combination therapy with one or two non-nucleoside reverse transcriptase inhibitors (e.g., Rescriptor, Sustiva, Viramune, etc.). An agent that reactivates latent immunodeficiency virus can be administered in combination therapy with one or two protease inhibitors (e.g., Agenerase, Crixivan, Fortovase, Invirase, Kaletra, Norvir, Viracept, etc.). An agent that reactivates latent immunodeficiency virus can be administered in combination therapy with a protease inhibitor and a nucleoside reverse transcriptase inhibitor. An agent that reactivates latent immunodeficiency virus can be administered in combination therapy with a protease inhibitor, a nucleoside reverse transcriptase inhibitor, and a non-nucleoside reverse transcriptase inhibitor. An agent that reactivates latent immunodeficiency virus can be administered in combination therapy with a protease inhibitor and a non-nucleoside reverse transcriptase inhibitor. Other combinations of an agent that reactivates latent immunodeficiency virus with one or more of a protease inhibitor, a nucleoside reverse transcriptase inhibitor, and a non-nucleoside reverse transcriptase inhibitor are contemplated.

In some embodiments, a subject treatment method involves administering: a) an agent that reactivates latent immunodeficiency virus; and b) an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a subject treatment method involves administering: a) an agent that reactivates latent immunodeficiency virus; and b) an HIV inhibitor, where suitable HIV inhibitors include, but are not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (e.g., CXCR4, CCR5) inhibitors, and hydroxyurea.

Nucleoside reverse transcriptase inhibitors include, but are not limited to, abacavir (ABC; ZIAGEN™), didanosine (dideoxyinosine (ddI); VIDEX™), lamivudine (3TC; EPIVIR™), stavudine (d4T; ZERIT™, ZERIT XR™), zalcitabine (dideoxycytidine (ddC); HIVID™), zidovudine (ZDV, formerly known as azidothymidine (AZT); RETROVIR™), abacavir, zidovudine, and lamivudine (TRIZIVIR™), zidovudine and lamivudine (COMBIVIR™), and emtricitabine (EMTRIVA™). Nucleotide reverse transcriptase inhibitors include tenofovir disoproxil fumarate (VIREAD™). Non-nucleoside reverse transcriptase inhibitors for HIV include, but are not limited to, nevirapine (VIRAMUNE™), delavirdine mesylate (RESCRIPTOR™), and efavirenz (SUSTIVA™).

Protease inhibitors (PIs) for treating HIV infection include amprenavir (AGENERASE™), saquinavir mesylate (FORTOVASE™, INVIRASE™), ritonavir (NORVIR™), indinavir sulfate (CRIXIVAN™), nelfmavir mesylate (VIRACEPT™), lopinavir and ritonavir (KALETRA™), atazanavir (REYATAZ™), and fosamprenavir (LEXIVA™).

Fusion inhibitors prevent fusion between the virus and the cell from occurring, and therefore, prevent HIV infection and multiplication. Fusion inhibitors include, but are not limited to, enfuvirtide (FUZEON™), Lalezari et al., New England J. Med., 348:2175-2185 (2003); and maraviroc (SELZENTRY™, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS™, Merck); and elvitegravir (GS 9137, Gilead Sciences).

Maturation inhibitors include, e.g., bevirimat (3β-(3-carboxy-3-methyl-butanoyloxy) lup-20(29)-en-28-oic acid); and Vivecon (MPC9055).

In some embodiments, a subject treatment method involves administering: a) an agent that reactivates latent immunodeficiency virus; and b) one or more of: (1) an HIV protease inhibitor selected from amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) an HIV non-nucleoside inhibitor of reverse transcriptase selected from capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) an HIV nucleoside inhibitor of reverse transcriptase selected from zidovudine, emtricitabine, didanosine, stavudine, zalcitabine, lamivudine, abacavir, amdoxovir, elvucitabine, alovudine, MIV-210, racivir, D-d4FC, emtricitabine, phosphazide, fozivudine tidoxil, apricitibine (AVX754), amdoxovir, KP-1461, and fosalvudine tidoxil (formerly HDP 99.0003); (4) an HIV nucleotide inhibitor of reverse transcriptase selected from tenofovir and adefovir; (5) an HIV integrase inhibitor selected from curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) a gp41 inhibitor selected from enfuvirtide, sifuvirtide, FB006M, and TRI-1144; (7) a CXCR4 inhibitor, such as AMD-070; (8) an entry inhibitor, such as SP01A; (9) a gp120 inhibitor, such as BMS-488043 and/or BlockAide/CR; (10) a G6PD and NADH-oxidase inhibitor, such as immunitin; (11) a CCR5 inhibitors selected from the group consisting of aplaviroc, vicriviroc, maraviroc, PRO-140, INCB15050, PF-232798 (Pfizer), and CCR5 mAb004; (12) another drug for treating HIV selected from BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS119, ALG 889, and PA-1050040 (PA-040); (13) any combinations or mixtures of the above.

As further examples, in some embodiments, a subject treatment method involves administering: a) an agent that reactivates latent immunodeficiency virus; and b) one or more of: i) amprenavir (Agenerase; (3S)-oxolan-3-yl N-[(2S,3R)-3-hydroxy-4-[N-(2-methylpropyl)(4-aminobenzene)sulfonamido]-1-phenylbutan-2-yl]carbamate) in an amount of 600 mg or 1200 mg twice daily; ii) tipranavir (Aptivus; N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide) in an amount of 500 mg twice daily; iii) idinavir (Crixivan; (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl)piperazine-2-carboxamide) in an amount of 800 mg three times daily; iv) saquinavir (Invirase; 2S)-N-[(2S,3R)-4-[(3 S)-3-(tert-butylcarbamoyl)-decahydroisoquinolin-2-yl]-3-hydroxy-1-phenylbutan-2-yl]-2-(quinolin-2-ylformamido)butanediamide) in an amount of 1,000 mg twice daily; v) lopinavir and ritonavir (Kaleta; where lopinavir is 2S)-N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide; and ritonavir is 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate) in an amount of 133 mg twice daily; vi) fosamprenavir (Lexiva; {[(2R,3S)-1-[N-(2-methylpropyl)(4-aminobenzene)sulfonamido]-3-({[(3S)-oxolan-3-yloxy]carbonyl}amino)-4-phenylbutan-2-yl]oxy}phosphonic acid) in an amount of 700 mg or 1400 mg twice daily); vii) ritonavir (Norvir) in an amount of 600 mg twice daily; viii) nelfinavir (Viracept; (3S,4aS,8aS)-N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide) in an amount of 750 mg three times daily or in an amount of 1250 mg twice daily; ix) Fuzeon (Acetyl-YTSLIHSLIEESQNQQEKNEQELLELDK-WASLWNWF-amide; SEQ ID NO:44) in an amount of 90 mg twice daily; x) Combivir in an amount of 150 mg lamivudine (3TC; 2',3'-dideoxy-3'-thiacytidine) and 300 mg zidovudine (AZT; azidothymidine) twice daily; xi) emtricitabine (Emtriva; 4-amino-5-fluoro-1-[(2R,5S)-2-(hydroxymethyl)-1,3-oxathiolan-5-yl]-1,2-dihydropyrimidin-2-one) in an amount of 200 mg once daily; xii) Epzicom in an amount of 600 mg abacavir (ABV; {(1S,4R)-4-[2-amino-6-(cyclopropylamino)-9H-purin-9-yl]cyclopent-2-en-1-yl}methanol) and 300 mg 3TC once daily; xiii) zidovudine (Retrovir; AZT or azidothymidine) in an amount of 200 mg three times daily; xiv) Trizivir in an amount of 150 mg 3TC and 300 mg ABV and 300 mg AZT twice daily; xv) Truvada in an amount of 200 mg emtricitabine and 300 mg tenofovir (({[(2R)-1-(6-amino-9H-purin-9-yl)propan-2-yl]oxy}methyl)phosphonic acid) once daily; xvi) didanosine (Videx; 2',3'-dideoxyinosine) in an amount of 400 mg once daily; xvii) tenofovir (Viread) in an amount of 300 mg once daily; xviii) abacavir (Ziagen) in an amount of 300 mg twice daily; xix) atazanavir (Reyataz; methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate) in an amount of 300 mg once daily or 400 mg once daily; xx) lamivudine (Epivir) in an amount of 150 mg twice daily; xxi) stavudine (Zerit; 2'-3'-didehydro-2'-3'-dideoxythymidine) in an amount of 40 mg twice daily; xxii) delavirdine (Rescriptor; N-[2-({4-[3-(propan-2-ylamino)pyridin-2-yl]piperazin-1-yl}carbonyl)-1H-indol-5-yl]methanesulfonamide) in an amount of 400 mg three times daily; xxiii) efavirenz (Sustiva; (4S)-6-chloro-4-(2-cyclopropylethynyl)-4-(trifluoromethyl)-2,4-dihydro-1H-3,1-benzoxazin-2-one) in an amount of 600 mg once daily); xxiv) nevirapine (Viramune; 11-cyclopropyl-4-methyl-5,11-dihydro-6H-dipyrido[3,2-b:2',3'-e][1,4]diazepin-6-one) in an amount of 200 mg twice daily); xxv) bevirimat; and xxvi) Vivecon.

In some embodiments, a subject treatment method involves administering: a) an agent that reactivates latent immunodeficiency virus; and b) a PKC activator. An example of a suitable PKC activator is prostratin ((1aR,1bS,4aR,7aS,7bR,8R,9aS)-4a,7b-dihydroxy-3-(hydroxymethyl)-1,1,6,8-tetramethyl-5-oxo-1,1a,1b,4,4a,5,7a,7b,8,9-decahydro-9aH-cyclopropa[3,4]benzo[1,2-e]azulen-9a-yl). The PKC activator can be administered in a separate formulation from an agent that reactivates latent immunodeficiency virus. A PKC activator can be co-formulated with an agent that reactivates latent immunodeficiency virus, and the co-formulation administered to an individual. The present disclosure provides a kit comprising a PKC activator in a first container; and an agent that reactivates latent immunodeficiency virus in a second container.

3) Methods of Reactivating Latent Immunodeficiency Virus with Synergistic Combinations The present disclosure provides compositions and methods for reactivating latent immunodeficiency virus in an immunodeficiency virus-infected cell. In some cases, the methods generally involve administering to an individual in need thereof a first active agent that reactivates latent immunodeficiency virus and a second agent that reactivates latent immunodeficiency virus, in amounts effective to activate latent immunodeficiency virus. The combination of the first active agent ("reactivator") and the second active agent ("enhancer") can be administered as part of a combination therapy with at least one anti-immunodeficiency virus therapeutic agent. It is noted that an "enhancer" compound can, in some cases, function as a reactivator.

A first active agent and a second active agent exhibit synergistic effects in reactivating latent immunodeficiency virus. Thus, the efficacy of the combination (e.g., combined administration, including where the two agents are administered together in a single composition, simultaneously in separate compositions, or sequentially in separate compositions) of the first active agent and the second active agent is greater than the sum of the effects of each agent given alone.

In some embodiments, the magnitude of immunodeficiency virus reactivation after contacting an immunodeficiency virus-infected cell with a first active agent and a second active agent is at least about 2.5-fold, 5-fold, at least about 10-fold, at least about 15-fold, at least about 20-fold, at least about 25-fold, at least about 30-fold, at least about 40-fold, at least about 50-fold, or more than 50-fold, greater than the additive effect of the first active agent or the second active agent alone in reactivating latent immunodeficiency virus.

An effective amount (combined effective amounts) of a first active agent ("reactivator") and a second active agent ("enhancer") is an amount that reactivates latent HIV and reduces the reservoir of latent HIV in an individual by at least about 20%, at least about 30%, at least about 40%, at least about 50%, at least about 60%, at least about 70%, at least about 80%, or at least about 90%. A "reduction in the reservoir of latent HIV" (also referred to as "reservoir of latently infected cells") is a reduction in the number of cells in the individual that harbor a latent HIV infection. Whether the reservoir of latently infected cells is reduced can be determined using any known method, including the method described in Blankson et al. (2000) *J. Infect. Disease* 182 (6):1636-1642.

Thus, the present disclosure provides a method of reducing the number of cells containing a latent human immunodeficiency virus in an individual. The methods generally involve administering to an individual in need thereof a first active agent ("reactivator") that reactivates latent immunodeficiency virus and a second agent ("enhancer") that enhances the effect of the first agent, in amounts effective to activate latent immunodeficiency virus.

First Active Agent ("Reactivator")

Suitable first active agents include, but are not limited to, suberoylanilide hydroxamic acid (SAHA); JQ1; an HDAC inhibitor; a bromodomain-4 inhibitor; Scriptaid; TNF-α; prostratin; and 12-deoxyphorbol 13-phenylacetate (DPP).

SAHA:

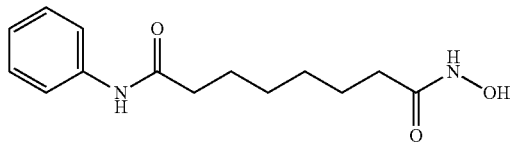

JQ1:

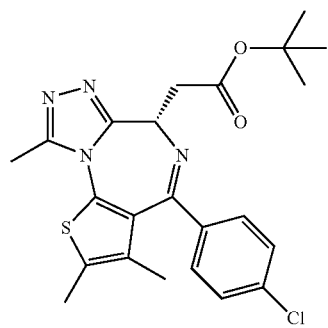

Scriptaid (6-(1,3-Dioxo-1H,3H-benzo[de]isoquinolin-2-yl)-hexanoic acid hydroxyamide):

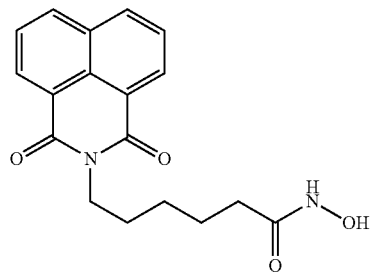

Prostratin:

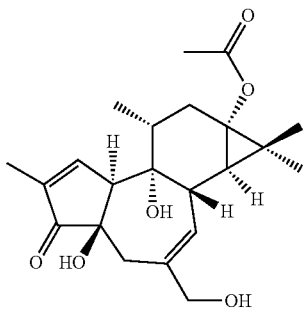

Suitable HDAC inhibitors include, e.g., butyric acid, phenylbutyrate, phenylacetate, trapoxin B, MS 275-27, a hydroximate, depudecin, oxamflatin, apicidin, Scriptaid, pyroxamide, 2-amino-8-oxo-9,10-epoxy-decanoyl, 3-(4-aroyl-1H-pyrrol-2-yl)-N-hydroxy-2-propenamide, CI-994, CHAP1, CHAP31, CHAP50, MS-275, M344, LAQ-824, FK228, FR901228, HC-toxin, and structural analogs thereof. Suitable hydroximates include, e.g., SAHA, azelaic bishydroxamic acid (ABHA), suberic bishydroxamic acid (SBHA), and m-carboxycinnamic acid bis-hydroxamide (CBHA).

Second Active Agent ("Enhancer")

Suitable second active agents include, but are not limited to, a Bruton's tyrosine kinase inhibitor (e.g., a quinone epoxide such as terreic acid); an adenosine reuptake inhibitor (e.g., dilazep); and a reseveratrol analog (e.g., piceatannol).

Terreic acid:

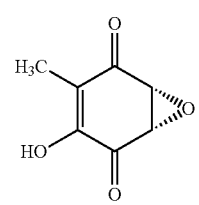

Dilazep:

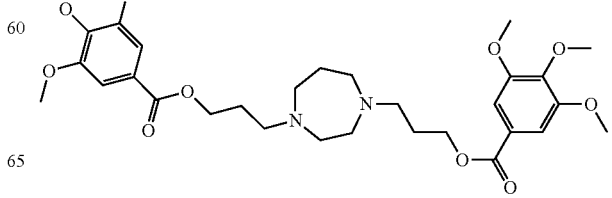

Piceatannol:

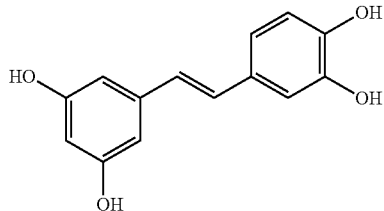

In some cases, a subject method comprises contacting an immunodeficiency virus-infected cell with synergistically effective amounts of: a) SAHA; and b) terreic acid. In some cases, a subject method comprises contacting an immunodeficiency virus-infected cell with synergistically effective amounts of: a) SAHA; and b) dilazep. In some cases, a subject method comprises contacting an immunodeficiency virus-infected cell with synergistically effective amounts of: a) SAHA; and b) piceatannol. In some cases, a subject method comprises contacting an immunodeficiency virus-infected cell with synergistically effective amounts of: a) prostratin; and b) terreic acid. In some cases, a subject method comprises contacting an immunodeficiency virus-infected cell with synergistically effective amounts of: a) prostratin; and b) dilazep. In some cases, a subject method comprises contacting an immunodeficiency virus-infected cell with synergistically effective amounts of: a) prostratin; and b) piceatannol. In some cases, a subject method comprises contacting an immunodeficiency virus-infected cell with synergistically effective amounts of: a) TNF-α; and b) dilazep. In some cases, a subject method comprises contacting an immunodeficiency virus-infected cell with synergistically effective amounts of: a) TNF-α; and b) piceatannol.

4) Methods of Treating an Immunodeficiency Virus Infection with Synergistic Combinations In some embodiments, a subject method of treating an immunodeficiency virus infection in an individual in need thereof involves: a) administering to the individual a synergistically effective amount of a first active agent ("reactivator") and a second active agent ("enhancer"); and b) administering to the individual an effective amount of an agent that inhibits an immunodeficiency virus function. The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity. Administering to the individual a synergistically effective amount of a first active agent ("reactivator") and a second active agent ("enhancer") results in reactivation of latent immunodeficiency virus. Administering an agent that inhibits an immunodeficiency virus function can result in one or both of: a reduction of immunodeficiency virus load in the individual; and an increase in the number of CD4+ T cells in the individual.

In some cases, a subject method comprises: a) administering to an individual in need thereof synergistically effective amounts of: i) SAHA; and ii) terreic acid; and b) administering to the individual an effective amount of an agent that inhibits an immunodeficiency virus function.

In some cases, a subject method comprises: a) administering to an individual in need thereof synergistically effective amounts of: i) SAHA; and ii) dilazep; and b) administering to the individual an effective amount of an agent that inhibits an immunodeficiency virus function.

In some cases, a subject method comprises: a) administering to an individual in need thereof synergistically effective amounts of: i) SAHA; and ii) piceatannol; and b) administering to the individual an effective amount of an agent that inhibits an immunodeficiency virus function.

In some cases, a subject method comprises: a) administering to an individual in need thereof synergistically effective amounts of: i) prostratin; and ii) terreic acid; and b) administering to the individual an effective amount of an agent that inhibits an immunodeficiency virus function.

In some cases, a subject method comprises: a) administering to an individual in need thereof synergistically effective amounts of: i) prostratin; and ii) dilazep; and b) administering to the individual an effective amount of an agent that inhibits an immunodeficiency virus function.

In some cases, a subject method comprises: a) administering to an individual in need thereof synergistically effective amounts of: i) prostratin; and ii) piceatannol; and b) administering to the individual an effective amount of an agent that inhibits an immunodeficiency virus function.

In some cases, a subject method comprises: a) administering to an individual in need thereof synergistically effective amounts of: i) TNF-α; and ii) dilazep; and b) administering to the individual an effective amount of an agent that inhibits an immunodeficiency virus function.

In some cases, a subject method comprises: a) administering to an individual in need thereof synergistically effective amounts of: i) TNF-α; and ii) piceatannol; and b) administering to the individual an effective amount of an agent that inhibits an immunodeficiency virus function.

Any of a variety of methods can be used to determine whether a treatment method is effective. For example, methods of determining whether the methods of the invention are effective in reducing immunodeficiency virus (e.g., HIV) viral load, and/or treating an immunodeficiency virus (e.g., HIV) infection, are any known test for indicia of immunodeficiency virus (e.g., HIV) infection, including, but not limited to, measuring viral load, e.g., by measuring the amount of immunodeficiency virus (e.g., HIV) in a biological sample, e.g., using a polymerase chain reaction (PCR) with primers specific for an immunodeficiency virus (e.g., HIV) polynucleotide sequence; detecting and/or measuring a polypeptide encoded by an immunodeficiency virus (e.g., HIV), e.g., p24, gp120, reverse transcriptase, using, e.g., an immunological assay such as an enzyme-linked immunosorbent assay (ELISA) with an antibody specific for the polypeptide; and measuring the CD4+ T cell count in the individual.

Methods of assaying an HIV infection (or any indicia associated with an HIV infection) are known in the art, and have been described in numerous publications such as HIV Protocols (Methods in Molecular Medicine, 17) N. L. Michael and J. H. Kim, eds. (1999) Humana Press.

Combination Therapies

A synergistically effective amount of a first active agent ("reactivator") and a second active agent ("enhancer") can be administered to an individual in combination (e.g., in the same formulation or in separate formulations) with another therapeutic agent ("combination therapy"). A synergistically effective amount a first active agent ("reactivator") and a second active agent ("enhancer") can be administered in admixture with another therapeutic agent or can be administered in a separate formulation. When administered in separate formulations, a synergistically effective amount of a first active agent ("reactivator") and a second active agent ("enhancer") and another therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Any of a variety of methods can be used to determine whether a treatment method is effective. For example, methods of determining whether the methods of the invention are effective in reducing HIV load, and/or treating an HIV infection, are any known test for indicia of HIV infection, including, but not limited to, measuring viral load, e.g., by measuring the amount of HIV in a biological sample, e.g., using a polymerase chain reaction (PCR) with primers specific for an HIV polynucleotide sequence; detecting and/or measuring a polypeptide encoded by HIV, e.g., p24, gp120, reverse transcriptase, using, e.g., an immunological assay such as an enzyme-linked immunosorbent assay (ELISA) with an antibody specific for the polypeptide; and measuring the $CD4^+$ T cell count in the individual.

Formulations, Dosages, Routes of Administration

In general, active agents (e.g., a first active agent ("reactivator") and a second active agent ("enhancer")) are prepared in a pharmaceutically acceptable composition(s) for delivery to a host. In some embodiments, a first active agent ("reactivator") and a second active agent ("enhancer") are formulated separately in separate pharmaceutical compositions. In other embodiments, a first active agent ("reactivator") and a second active agent ("enhancer") are formulated together in a single pharmaceutical composition. The terms "active agent," "drug," "agent," "therapeutic agent," and the like are used interchangeably herein. Pharmaceutically acceptable carriers preferred for use with active agents (e.g., a first active agent ("reactivator") and a second active agent ("enhancer"); and optionally one or more additional therapeutic agent) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (e.g., a first active agent ("reactivator") and a second active agent ("enhancer"); and optionally one or more additional therapeutic agent) may also be lyophilized using means well known in the art, for subsequent reconstitution and use according to the invention.

Formulations

Active agents (e.g., a first active agent ("reactivator") and a second active agent ("enhancer"); and optionally one or more additional therapeutic agent) are administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. For the purposes of the following description of formulations, "active agent" includes a first active agent ("reactivator") and a second active agent ("enhancer"), and optionally one or more additional therapeutic agent.

In a subject method, active agents (e.g., a first active agent ("reactivator") and a second active agent ("enhancer"); and optionally one or more additional therapeutic agent) may be administered to the host using any convenient means capable of resulting in the desired degree of reactivation of latent immunodeficiency virus. Thus, active agents (e.g., a first active agent ("reactivator") and a second active agent ("enhancer"); and optionally one or more additional therapeutic agent) can be incorporated into a variety of formulations for therapeutic administration. More particularly, active agents (e.g., a first active agent ("reactivator") and a second active agent ("enhancer"); and optionally one or more additional therapeutic agent) can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent (e.g., a first active agent ("reactivator") and a second active agent ("enhancer"); and optionally one or more additional therapeutic agent) is formulated as a gel, as a solution, or in some other form suitable for intravaginal administration. In a further exemplary embodiment, an active agent (e.g., a first active agent ("reactivator") and a second active agent ("enhancer"); and optionally one or more additional therapeutic agent) is formulated as a gel, as a solution, or in some other form suitable for rectal (e.g., intrarectal) administration.

In pharmaceutical dosage forms, an active agent (e.g., a first active agent ("reactivator") and a second active agent ("enhancer"); and optionally one or more additional therapeutic agent) may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an agent (e.g., a first active agent ("reactivator") and a second active agent ("enhancer"); and optionally one or more additional therapeutic agent) is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent (e.g., a first active agent ("reactivator") and a second active agent ("enhancer"); and optionally one or more additional therapeutic agent) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent (e.g., a first active agent ("reactivator") and a second active agent ("enhancer"); and optionally one or more additional therapeutic agent) can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent (e.g., a first active agent ("reactivator") and a second active agent ("enhancer"); and optionally one or more additional therapeutic agent) can be utilized in aerosol formulation to be administered via inhalation. An active agent (e.g., a first active agent ("reactivator") and a second active agent ("enhancer"); and optionally one or more additional therapeutic agent) can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered in an injectable composition. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration is formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

As noted above, in some embodiments, a first active agent ("reactivator") and a second active agent ("enhancer") are formulated in a single pharmaceutical composition. Thus, the present disclosure provides a pharmaceutical composition comprising: a) a first active agent ("reactivator"); b) a second active agent ("enhancer"); and c) a pharmaceutically acceptable carrier, where the first and second active agents are present in amounts effective to synergistically reactivate latent immunodeficiency virus in an immunodeficiency virus-infected cell.

Dosages

Although the dosage used will vary depending on the clinical goals to be achieved, a suitable dosage range is one which provides up to about 1 mg to about 1000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, or from about 500 mg to about 1000 mg of an active agent (e.g., a first active agent ("reactivator") and a second active agent ("enhancer"); and optionally one or more additional therapeutic agent) can be administered in a single dose.

A synergistically effective amount is in some embodiments at least 10% less, at least 15% less, at least 20% less, at least 25% less, at least 30% less, at least 35% less, at least 40% less, or at least 50% less, than the amount that would normally be required in monotherapy to achieve the same effect, e.g., reactivation of latent immunodeficiency virus.

In some cases, where the first agent is SAHA (or another HDAC inhibitor), the dosage of SAHA (or other HDAC inhibitor) will be less than 100 mg/kg/day, less than 50 mg/kg/day, or less than 25 mg/kg/day. In some cases, the dosage of SAHA will be from about 0.1 mg/kg/day to about 1 mg/kg/day, from about 1 mg/kg/day to about 5 mg/kg/day, from about 5 mg/kg/day to about 10 mg/kg/day, from about 10 mg/kg/day to about 15 mg/kg/day, or from about 15 mg/kg/day to about 20 mg/kg/day. "Mg/kg" refers to milligrams per kilogram body weight.

In some cases, where the first agent is prostratin, the daily dose can be in the range of about 5 mg/kg to about 500 mg/kg. In some cases, the daily dose is about 10 mg/kg to about 250 mg/kg. In other cases, the daily dose is about 25 mg/kg to about 150 mg/kg. An exemplary dose is about 10 mg/kg. In some cases, prostratin is administered in a daily dose of from about 0.2 mg/kg to about 5 mg/kg, e.g., from about 0.2 mg/kg to about 0.4 mg/kg, from about 0.4 mg/kg to about 0.6 mg/kg, from about 0.6 mg/kg to about 1.0 mg/kg, from about 1.0 mg/kg to about 2.0 mg/kg, from about 2.0 mg/kg to about 3.0 mg/kg, from about 3.0 mg/kg to about 4.0 mg/kg, or from about 4.0 mg/kg to about 5.0 mg/kg.

In some cases, where the first agent is tumor necrosis factor-α (TNF-α), the daily dose can be in the range of from about 0.1 mg/kg to about 10 mg/kg, e.g., from about 0.1 mg/kg to about 0.2 mg/kg, from about 0.2 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 3.0 mg/kg, from about 3.0 mg/kg to about 3.5 mg/kg, from about 3.5 mg/kg to about 4.0 mg/kg, from about 4.0 mg/kg to about 5.0 mg/kg, or from about 5.0 mg/kg to about 10 mg/kg.

In some cases, where the second agent is dilazep, the daily dose can be in the range of from about 0.1 mg/kg to about 10 mg/kg, e.g., from about 0.1 mg/kg to about 0.2 mg/kg, from about 0.2 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 3.0 mg/kg, from about 3.0 mg/kg to about 3.5 mg/kg, from about 3.5 mg/kg to about 4.0 mg/kg, from about 4.0 mg/kg to about 5.0 mg/kg, or from about 5.0 mg/kg to about 10 mg/kg.

In some cases, wherein the second agent is piceatannol, the daily dose can be in the range of from about 0.5 mg/kg to about 50 mg/kg, e.g., from about 0.5 mg/kg to about 1 mg/kg, from about 1 mg/kg to about 2 mg/kg, from about 2 mg/kg to about 5 mg/kg, from about 5 mg/kg to about 10 mg/kg, from about 10 mg/kg to about 20 mg/kg, from about 20 mg/kg to about 30 mg/kg, from about 30 mg/kg to about 40 mg/kg, or from about 40 mg/kg to about 50 mg/kg.

In some cases, wherein the second agent is terreic acid, the daily doses can be in the range of from about 0.1 mg/kg to about 10 mg/kg, e.g., from about 0.1 mg/kg to about 0.2 mg/kg, from about 0.2 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 3.0 mg/kg, from about 3.0 mg/kg to about 3.5 mg/kg, from about 3.5 mg/kg to about 4.0 mg/kg, from about 4.0 mg/kg to about 5.0 mg/kg, or from about 5.0 mg/kg to about 10 mg/kg.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent (e.g., a first active agent ("reactivator") and a second active agent ("enhancer"); and optionally one or more additional therapeutic agent) is administered. In other embodiments, multiple doses of an active agent (e.g., a first active agent ("reactivator") and a second active agent ("enhancer"); and optionally one or more additional therapeutic agent) are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

A first active agent ("reactivator") and a second active agent ("enhancer") can be administered in separate formulations. A first active agent ("reactivator") and a second active agent ("enhancer") can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent (e.g., a first active agent ("reactivator") and a second active agent ("enhancer"); and optionally one or more additional therapeutic agent) is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent (e.g., a first active agent ("reactivator") and a second active agent ("enhancer"); and optionally one or more additional therapeutic agent) can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent (e.g., a first active agent ("reactivator") and a second active agent ("enhancer"); and optionally one or more additional therapeutic agent) can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to immunodeficiency virus (e.g., HIV) infection. In many embodiments, the hosts will be humans.

Combination Therapies

A first active agent ("reactivator") and a second active agent ("enhancer") can be administered to an individual in combination (e.g., in the same formulation or in separate formulations) with at least one additional therapeutic agent ("combination therapy"). A first active agent ("reactivator") and a second active agent ("enhancer") can be administered in admixture with at least one additional therapeutic agent or can be administered in separate formulations. When administered in separate formulations, a first active agent ("reactivator") and a second active agent ("enhancer"), and at least one additional therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a first active agent ("reactivator") and a second active agent ("enhancer") are as described above.

In some embodiments, the combination therapy comprises Highly Active Anti-Retroviral Therapy (HAART) in combination with administering a reactivating agent (or agents), as described herein. HAART includes two reverse transcriptase inhibitors and a protease inhibitor.

Therapeutic agents that can be administered in combination therapy with a first active agent ("reactivator") and a second active agent ("enhancer") include, e.g., anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat viral infections. In some embodiments, patients with a viral or bacterial infection are treated with a combination of a first active agent ("reactivator") and a second active agent ("enhancer"), and one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™) famcyclovir, pencyclovir, valacyclovir, nucleic acid/replication inhibitors, interferon, zidovudine (AZT, Retrovir™), zidovudine/lamivudine (Combivir), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), lopinavir/ritonavir (Kaletra), trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a synergistically effective amount of a first active agent ("reactivator") and a second active agent ("enhancer") is administered in combination therapy with two or more anti-HIV agents. For example, a synergistically effective amount of a first active agent ("reactivator") and a second active agent ("enhancer") can be administered in combination therapy with one, two, or three nucleoside reverse transcriptase inhibitors (e.g., Combivir, Epivir, Hivid, Retrovir, Videx, Zerit, Ziagen, etc.). A synergistically effective amount of a first active agent ("reactivator") and a second active agent ("enhancer") can be administered in combination therapy with one or two non-nucleoside reverse transcriptase inhibitors (e.g., Rescriptor, Sustiva, Viramune, etc.). A synergistically effective amount of a first active agent ("reactivator") and a second active agent ("enhancer") can be administered in combination therapy with one or two protease inhibitors (e.g., Agenerase, Crixivan, Fortovase, Invirase, Kaletra, Norvir, Viracept, etc.). A synergistically effective amount a first active agent ("reactivator") and a second active agent ("enhancer") can be administered in combination therapy with a protease inhibitor and a nucleoside reverse transcriptase inhibitor. A synergistically effective amount of a first active agent ("reactivator") and a second active agent ("enhancer") can be administered in combination therapy with a protease inhibitor, a nucleoside reverse transcriptase inhibitor, and a non-nucleoside reverse transcriptase inhibitor. A synergistically effective amount of a first active agent ("reactivator") and a second active agent ("enhancer") can be administered in combination therapy with a protease inhibitor and a non-nucleoside reverse transcriptase inhibitor. Other combinations of a synergistically effective amount of a first active agent ("reactivator") and a second active agent ("enhancer") with one or more of a protease inhibitor, a nucleoside reverse transcriptase inhibitor, and a non-nucleoside reverse transcriptase inhibitor are contemplated.

In some embodiments, a subject treatment method involves administering: a) a synergistically effective amount of a first active agent ("reactivator") and a second active agent ("enhancer"); and b) an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a subject treatment method involves administering: a) a synergistically effective amount of a first active agent ("reactivator") and a second active agent ("enhancer"); and b) an HIV inhibitor, where suitable HIV inhibitors include, but are not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (e.g., CXCR4, CCR5) inhibitors, and hydroxyurea.

Nucleoside reverse transcriptase inhibitors include, but are not limited to, abacavir (ABC; ZIAGEN™), didanosine (dideoxyinosine (ddI); VIDEX™), lamivudine (3TC; EPI-VIR™), stavudine (d4T; ZERIT™, ZERIT XR™), zalcitabine (dideoxycytidine (ddC); HIVID™), zidovudine (ZDV, formerly known as azidothymidine (AZT); RETROVIR™), abacavir, zidovudine, and lamivudine (TRIZIVIR™), zidovudine and lamivudine (COMBIVIR™), and emtricitabine (EMTRIVA™). Nucleotide reverse transcriptase inhibitors include tenofovir disoproxil fumarate (VIREAD™). Non-nucleoside reverse transcriptase inhibitors for HIV include, but are not limited to, nevirapine (VIRAMUNE™), delavirdine mesylate (RESCRIPTOR™), and efavirenz (SUSTIVA™).

Protease inhibitors (PIs) for treating HIV infection include amprenavir (AGENERASE™), saquinavir mesylate (FORTOVASE™, INVIRASE™), ritonavir (NORVIR™), indinavir sulfate (CRIXIVAN™), nelfmavir mesylate (VIRACEPT™), lopinavir and ritonavir (KALETRA™), atazanavir (REYATAZ™), and fosamprenavir (LEXIVA™).

Fusion inhibitors prevent fusion between the virus and the cell from occurring, and therefore, prevent HIV infection and multiplication. Fusion inhibitors include, but are not limited to, enfuvirtide (FUZEON™), Lalezari et al., New England J. Med., 348:2175-2185 (2003); and maraviroc (SELZENTRY™, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS™, Merck); and elvitegravir (GS 9137, Gilead Sciences).

Maturation inhibitors include, e.g., bevirimat (3β-(3-carboxy-3-methyl-butanoyloxy) lup-20(29)-en-28-oic acid); and Vivecon (MPC9055).

In some embodiments, a subject treatment method involves administering: a) a synergistically effective amount of a first active agent ("reactivator") and a second active agent ("enhancer"); and b) one or more of: (1) an HIV protease inhibitor selected from amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) an HIV non-nucleoside inhibitor of reverse transcriptase selected from capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) an HIV nucleoside inhibitor of reverse transcriptase selected from zidovudine, emtricitabine, didanosine, stavudine, zalcitabine, lamivudine, abacavir, amdoxovir, elvucitabine, alovudine, MIV-210, racivir (@-FTC), D-d4FC, emtricitabine, phosphazide, fozivudine tidoxil, apricitibine (AVX754), amdoxovir, KP-1461, and fosalvudine tidoxil (formerly HDP 99.0003); (4) an HIV nucleotide inhibitor of reverse transcriptase selected from tenofovir and adefovir; (5) an HIV integrase inhibitor selected from curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) a gp41 inhibitor selected from enfuvirtide, sifuvirtide, FB006M, and TRI-1144; (7) a CXCR4 inhibitor, such as AMD-070; (8) an entry inhibitor, such as SP01A; (9) a gp120 inhibitor, such as BMS-488043 and/or BlockAide/CR; (10) a G6PD and NADH-oxidase inhibitor, such as immunitin; (11) a CCR5 inhibitors selected from the group consisting of aplaviroc, vicriviroc, maraviroc, PRO-140, INCB15050, PF-232798 (Pfizer), and CCR5 mAb004; (12) another drug for treating HIV selected from BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS119, ALG 889, and PA-1050040 (PA-040); (13) any combinations or mixtures of the above.

For example, in some embodiments, a subject treatment method involves administering: a) a synergistically effective amount of a first active agent ("reactivator") and a second active agent ("enhancer"); and b) one or more of: i) amprenavir (Agenerase; (3S)-oxolan-3-yl N-[(2S,3R)-3-hydroxy-4-[N-(2-methylpropyl)(4-aminobenzene)sulfonamido]-1-phenylbutan-2-yl]carbamate) in an amount of 600 mg or 1200 mg twice daily; ii) tipranavir (Aptivus; N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)

pyridine-2-sulfonamide) in an amount of 500 mg twice daily; iii) idinavir (Crixivan; (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl) piperazine-2-carboxamide) in an amount of 800 mg three times daily; iv) saquinavir (Invirase; 2S)-N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide) in an amount of 1,000 mg twice daily; v) lopinavir and ritonavir (Kaleta; where lopinavir is 2S)-N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide; and ritonavir is 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate) in an amount of 133 mg twice daily; vi) fosamprenavir (Lexiva; {[(2R,3S)-1-[N-(2-methylpropyl)(4-aminobenzene)sulfonamido]-3-({[(3S)-oxolan-3-yloxy]carbonyl}amino)-4-phenylbutan-2-yl]oxy}phosphonic acid) in an amount of 700 mg or 1400 mg twice daily); vii) ritonavir (Norvir) in an amount of 600 mg twice daily; viii) nelfinavir (Viracept; (3S,4aS,8aS)-N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide) in an amount of 750 mg three times daily or in an amount of 1250 mg twice daily; ix) Fuzeon (Acetyl-YTSLIHSLIEESQNQQEKNEQELLELDKWASLWNWF-amide) (SEQ ID NO:44) in an amount of 90 mg twice daily; x) Combivir in an amount of 150 mg lamivudine (3TC; 2',3'-dideoxy-3'-thiacytidine) and 300 mg zidovudine (AZT; azidothymidine) twice daily; xi) emtricitabine (Emtriva; 4-amino-5-fluoro-1-[(2R,5S)-2-(hydroxymethyl)-1,3-oxathiolan-5-yl]-1,2-dihydropyrimidin-2-one) in an amount of 200 mg once daily; xii) Epzicom in an amount of 600 mg abacavir (ABV; {(1S,4R)-4-[2-amino-6-(cyclopropylamino)-9H-purin-9-yl]cyclopent-2-en-1-yl}methanol) and 300 mg 3TC once daily; xiii) zidovudine (Retrovir; AZT or azidothymidine) in an amount of 200 mg three times daily; xiv) Trizivir in an amount of 150 mg 3TC and 300 mg ABV and 300 mg AZT twice daily; xv) Truvada in an amount of 200 mg emtricitabine and 300 mg tenofovir (({[(2R)-1-(6-amino-9H-purin-9-yl)propan-2-yl]oxy}methyl)phosphonic acid) once daily; xvi) didanosine (Videx; 2',3'-dideoxyinosine) in an amount of 400 mg once daily; xvii) tenofovir (Viread) in an amount of 300 mg once daily; xviii) abacavir (Ziagen) in an amount of 300 mg twice daily; xix) atazanavir (Reyataz; methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate) in an amount of 300 mg once daily or 400 mg once daily; xx) lamivudine (Epivir) in an amount of 150 mg twice daily; xxi) stavudine (Zerit; 2'-3'-didehydro-2'-3'-dideoxythymidine) in an amount of 40 mg twice daily; xxii) delavirdine (Rescriptor; N-[2-({4-[3-(propan-2-ylamino)pyridin-2-yl]piperazin-1-yl}carbonyl)-1H-indol-5-yl]methanesulfonamide) in an amount of 400 mg three times daily; xxiii) efavirenz (Sustiva; (4S)-6-chloro-4-(2-cyclopropylethynyl)-4-(trifluoromethyl)-2,4-dihydro-1H-3,1-benzoxazin-2-one) in an amount of 600 mg once daily); xxiv) nevirapine (Viramune; 11-cyclopropyl-4-methyl-5,11-dihydro-6H-dipyrido[3,2-b:2',3'-e][1,4]diazepin-6-one) in an amount of 200 mg twice daily); xxv) bevirimat; and xxvi) Vivecon.

Kits, Containers, Devices, Delivery Systems

Kits with unit doses (e.g., synergistically effective doses) of a first active agent ("reactivator") and a second active agent ("enhancer"), e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an immunodeficiency virus (e.g., HIV) infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present disclosure provides a delivery system comprising a first active agent ("reactivator") and a second active agent ("enhancer"), where the combination of the two agents synergistically reactivate latent immunodeficiency virus in an immunodeficiency virus-infected cell. In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, a first active agent ("reactivator") and a second active agent ("enhancer") are packaged for oral administration. The present disclosure provides a packaging unit comprising daily dosage units of a first active agent ("reactivator") and a second active agent ("enhancer"), in separate formulations or co-formulated. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the present disclosure provides an injection delivery device that is pre-loaded with a formulation comprising synergistically effective amounts of a first active agent ("reactivator") and a second active agent ("enhancer"). For example, a subject delivery device comprises an injection device pre-loaded with a single dose of a first active agent ("reactivator") and a second active agent ("enhancer"). A subject injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096, 010, 6,146,361, 6,248,095, 6,277,099, and 6,221,053; and the like. The medication delivery pen can be disposable, or reusable and refillable.

In some embodiments, the delivery system comprises a first container comprising a composition comprising a first active agent ("reactivator") and a second containing comprising a composition comprising a second active agent ("enhancer"). The first and second containers can be, e.g., syringes. The delivery system can further comprise needles for use together with the syringes. The present disclosure provides a device comprising a first container comprising a composition comprising a first active agent ("reactivator"); and a second container comprising a composition comprising a second active agent ("enhancer"). The first and second containers can be, e.g., syringes.

The present disclosure provides a delivery system for vaginal or rectal delivery of a first active agent ("reactivator") and a second active agent ("enhancer") to the vagina or rectum of an individual. The delivery system comprises a device for insertion into the vagina or rectum. In some embodiments, the delivery system comprises an applicator for delivery of a formulation into the vagina or rectum; and a container that contains a formulation(s) comprising a first active agent ("reactivator") and a second active agent ("enhancer"), where the first active agent and the second active agent can be formulated separately or can be co-formulated. In these embodiments, the container (e.g., a tube) is adapted for delivering a formulation into the applicator. In other embodiments, the delivery system comprises a device that is inserted into the vagina or rectum, which device includes an active agent. For example, the device is coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909 If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. An active agent(s) is incorporated into a silicone matrix which is coated onto a cylindrical drug-free polyurethane sponge, as described in the literature.

Pessaries, tablets and suppositories are other examples of drug delivery systems which can be used in connection with a subject treatment method. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10 µm to 100 µm and can be prepared from starch, gelatin, albumin, collagen, or dextran.

Another system is a container (e.g., a tube) comprising a subject formulation that is adapted for use with an applicator. An active agent (e.g., a first active agent ("reactivator") and a second active agent ("enhancer")) is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Subjects Suitable for Treatment

The methods of the present disclosure are suitable for treating individuals who have an immunodeficiency virus infection, e.g., who have been diagnosed as having an immunodeficiency virus infection.

The methods of the present disclosure are suitable for treating individuals who have an HIV infection (e.g., who have been diagnosed as having an HIV infection), and individuals who are at risk of contracting an HIV infection. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals. Individuals suitable for treatment include individuals infected with, or at risk of becoming infected with, HIV-1 and/or HIV-2 and/or HIV-3, or any variant thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); ml, milliliter(s); A microliter(s); nl, nanoliter(s); pl, picoliter(s); U, unit(s); s or sec, second(s); min, minute(s); h or hr or hrs, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

The following Materials and Methods were used for Examples 1-4.

Plasmid Construction

HIV clones 89.6-DNE-SFG and R7/E-/GFP were linearized by PCR using opposing primers (see Table 1, #A and B) in the position selected for insertion (FIG. 1). mApple and the EF1a-mCherry sequences were cloned in the respective plasmids by a modified SLIC technique (Li and Elledge, Methods Mol Biol. 2012;852:51-9, which is hereby incorporated by reference in its entirety). Briefly, inserts were PCR-amplified from plasmid templates with primers that have a 20 bp 5'-overhang complementary to the end sequences of the blunted plasmids (see Table 1, #C and D). DNA from all amplifications was gel-purified, digested with 3'-5' exonuclease (T4-polymerase, Novagen, 30 min, 25° C.) and heat-inactivated (20 min, 75° C.). Digested inserts and vectors for each construct were mixed at a 2:1 molar ratio for complementary-end sequence annealing (20 min, 37° C.) and transformed in chemically competent Stbl-2 E. coli. Positive clones were resequenced entirely.

TABLE 1

Primer table. Bases surround by parenthesis (e.g., "(g)" or "(t)") for SEQ ID NOs: 10-12, 14, and 16 are degenerate bases so that the same primer will amplify from R7GEMC and from 89mASG.

| # | Name | Sequence | SEQ ID NO: |
|---|---|---|---|
| A | SLIC_mApple_Nef_F | GGAAAGGGCTTTGCTATAAGATGGTGAGCAAGGGCGA | 1 |
|   | SLIC_mApple_Nef_R | TATATCTGGCCCGTACATCGTTACTTGTACAGCTCGTCCA | 2 |
| B | 89.6_upNef_R | CTTATAGCAAAGCCCTTTCC | 3 |
|   | 89.6_downNef_F | CGATGTACGGGCCAGATATA | 4 |
| C | SLIC_R7_R | GCTTTACTTGTACAGCTCGTCCATGC | 5 |
|   | SLIC_R7_F | CTCATGAGCTGTAGATCTTAGCCACTT | 6 |
| D | SLIC_EF1mCh_F | ACGAGCTGTACAAGTAAAGCGACCCTCGAGTACTAGGATCCATTAGG | 7 |
|   | SLIC_EF1mCh_R | TAAGATCTACAGCTCATGAGAGCCATGGCTTCCCGCCGGCGGT | 8 |
| E | US RNA-gag-F | AAAAGAGACCATCAATGAGGAAGC | 9 |
|   | US RNA-gag-R | TGGTGCAAT(c)AGGCCCTGC | 10 |
|   | US RNA-gag-Probe | CAGAATGGGATAGAT(g)TGCATCCAGTGCA | 11 |
| F | MS RNA-total-F | ACAGTCAGACTCATCAAGC(t)TTCTC | 12 |
|   | MS RNA-total-R | CTGTCGGGTCCCCTCG | 13 |
|   | MS RNA-total-Probe | TTCTCTATCAAAGCAACCCA(t)CCTCCCA | 14 |
| G | SS RNA-env-F | CGGCGACTGGAAGAAGCGGA | 15 |
|   | SS RNA-env-R | TACTATG(a)GACCACACAACTATTGC | 16 |
|   | SS RNA-env-Probe | CGACGAAGAGCTCATCAGAACAGTCAGACTC | 17 |

Virus Production

HEK293T cells were cotransfected with the viral plasmid clone of interest and the env-encoding plasmid pSVIII-92HT593.1 (NARP), using Lipofectamine 2000. Medium (DMEM, 10% FBS) was changed 8 h post-transfection and collected at 72 h. Virus supernatant was filtered through a 0.45 μm-pore membrane, concentrated by ultracentrifugation and stored at −80° C. Virus concentration was estimated by p24 titration (HIV-1 alliance p24 ELISA kit, PerkinElmer).

Cells and Treatments

HEK293T, Jurkat, A301 and SupT1 cell lines were obtained from ATCC. Suspension cells were cultured in RPMI 1640 supplemented with 10% FBS, 100 U/ml penicillin, 100 mg/ml streptomycin and 2 mM L-glutamine (PSG) (37° C., 5% $CO_2$). Peripheral blood from healthy human donors was obtained from the Stanford Blood Center and processed the day of collection. CD4$^+$ T cells were isolated with RosetteSep Human CD4$^+$ T-Cell Enrichment Cocktail (Stem Cell Technologies) and cultured in human cell medium (HCM, RPMI, 10% human AB pooled serum, PSG). Resting CD4$^+$ T cells were activated in U-bottom 96-well TC plates with 25 μl human anti-CD3 and anti-CD28-coated dynabeads/10$^6$ cells (48 h). Dynabeads were removed by magnetic separation and cells seeded in HCM with 30 IU/ml rhIL-2. Cell lines and activated CD4+ cells were infected by spinoculation (Lassen et al., PLoS One. 2012; 7(1):e30176, which is hereby incorporated by reference in its entirety) with a virus amount equivalent to 20 ng p24 or as indicated. Viral infection was assessed by fluorescence activated cell sorting (FACS) analysis after 72 h. At 5 days post-infection, cells were sorted to separate negative, single- or double-positive cells. Sorted cell lines were treated after re-expansion for 5-15 days. Cells were seeded in 96-well U plates and treated for 24 h before analysis. CD4+ T cells were reseeded after sorting in 96-well U plates with HCM in the absence of IL-2 and treated after 24 h with drugs or human T-activator Dynabeads (48 h). Raltegravir (NARP), TNF-α (LT), prostratin, SAHA, bryostatin-1, PMA, HMBA, PHA-M were used in culture at indicated concentrations. This study was conducted according to the principles expressed in the Declaration of Helsinki. All individuals provided written informed consent for the collection of samples and subsequent analysis, as approved by the Institutional Review Board of the Stanford University Blood Bank.

Flow Cytometry and Cell Sorting

EGFP, mApple and mCherry fluorescence were measured in a MACSQuant VYB FACS analyzer, FACSCalibur, LSRII, and sorted in a FACSAriaII. Data were analyzed using FlowJo 9.4.

DNA, RNA and Protein Extraction, qPCR and Western Blot

DNA and RNA were extracted with Dneasy and RNeasy kits, respectively (Qiagen). RNA was retrotranscribed with the high capacity kit cDNA (Life technologies) and qPCR was performed in the AB 7900HT Fast Real-Time PCR System, using TaqMan 2× Master Mix and the appropriate primer-probe combinations (Table 1, #E, F, and G). Quantification for each qPCR reaction was assessed by interpolation on a template dilution curve. As normalization controls TaqMan Copy Number Reference Assay, RNase P was used for genomic DNA and TaqMan assay GAPDH Hs99999905_m1 for cDNA. Protein was extracted from freshly sorted cells in RIPA buffer, followed by SDS-PAGE. Bands were detected by chemiluminescence (ECL Hyperfilm Amersham) or fluorescence (Licor Odyssey) detection with anti-vif, HIV-p24 and -α-actin (Sigma) primary antibodies.

Fluorescence Microscopy

Cells were analyzed with an Axio observer Z1 microscope (Zeiss) equipped with EC Plan Neofluar 20×/0.5 PHM27, EC Plan Neofluar 40×/0.75 PH, and Plan Apo 63×/1.4 Oil DIC M27 objectives, filter sets 38HE, 43HE, 45, and 50, Optovar 1.25× and 1.6× magnification, and an Axiocam MRM REV 3.

Drug Screening

Sorted GFP-only 89mASG cells-infected Jurkat cells were expanded in culture and seeded at a 5×103 cells/well density in 384-well plates (black, clear bottom, Greiner), coated with Cell-Tak (BD). Tocriscreen total drug screening library, containing 1120 biologically active compounds dissolved in DMSO, was dispensed in the plate at a concentration of 30 μM, using the automated Beckman and Coulter Biomek FXP robot and 50 nl VP 384 pin tool. After 24 h culture in standard conditions, Hoechst 33342 was automatically dispensed with Thermo multodrop 384 to each well to evaluate total cell number of cell; plates were imaged in the InCell analyzer and analyzed with InCell Developer image analysis software. The total area masked by the nuclear stain and the total area of cells expressing mApple were quantified as proxies for cell number and number of cells which had reactivated viral transcription, respectively. On negative control wells, the median and standard deviation were calculated and the statistics to select significant conditions that differed from these expected values by more than 2SD.

Example 1

Dual-Color Viruses Allow Direct Labeling of Live HIV Latently Infected Cells

To identify latently infected cells prior to reactivation, two novel HIV-1-based lentiviral constructs were designed in which LTR expression is monitored by production of a fluorescent protein while another independent transcriptional unit expresses a spectrally distinct fluorescent protein under the control of an independent promoter. To construct the first clone, the 89.6/DNE/SFG reporter was used in which nef is replaced by a Spleen Focus Forming Virus (SFFV)-promoter-driven enhanced green fluorescent protein (EGFP; FIG. 1B). This clone has an env deletion, which limits infection to a single round. A sequence- and ligation-independent cloning (SLIC) strategy was used to reconstitute the nef ATG sequence and replace the remainder of the nef open reading frame with the sequence of a red fluorescent protein, mApple (Shaner et al, Nat Methods. 2008 June; 5(6):545-51, which is hereby incorporated by reference in its entirety) (FIG. 1B, D); this construct was named 89.6/DNE/mApple/SFG (89mASG). The nucleotide sequence of 89mASG is set forth in SEQ ID NO:23.

The second construct was derived from the HXB2-based R7/3 clone bearing EGFP in place of nef and an env deletion (Jordan et al., EMBO J. 2003 Apr. 15; 22(8):1868-77, which is hereby incorporated by reference in its entirety) (FIG. 1C). The SLIC technique was used to insert the whole EF1α-mCherry transcriptional unit between the EGFP and the virus 3' LTR (FIG. 1C, D). This construct was named R7/E-/GFP/EF1a-mCherry (R7GEmC). The nucleotide sequence of R7GEmC is set forth in SEQ ID NO:29.

To test the potential of these viral reporters to differentiate latent from actively infected and uninfected cell populations, Jurkat T cells were infected with the HIV constructs (FIG. 1E, F). After infection, a double-positive population expressing the HIV promoter-dependent reporter and the HIV promoter-independent reporter (SFFV or EF1α promoter) emerged for both viruses (FIG. 1E, F). In addition, a single-positive population expressing only the HIV promoter-independent reporter was detected; green for 89mASG (FIG. 1E) and red for R7GEmC (FIG. 1F).

To confirm that the single-positive cells expressing only the non-HIV promoter-driven reporter were latently infected cells, the GFP-only-positive and mCherry-only-positive cells were sorted from the 89mASG-infected and R7GEmC-infected pools, respectively, as well as the double-positive (productively infected) and the double-negative (uninfected) cells for each pool (FIG. 1G, H; left). The single-positive and double-negative cells were expanded in vitro after sorting, whereas the double-positive cells did not expand efficiently and largely died after sorting (especially the 89mASG-infected), as predicted by the cytotoxic properties of active viral infection. The different sorted populations were analyzed for viral DNA, RNA and protein content. Whereas the double-negative cells had low HIV DNA levels, the single-positive cells had DNA amounts comparable to those of double-positive cells (FIG. 1I) but expressed no detectable viral mRNA (FIG. 1J) or protein (FIG. 1K). Only the double-positive population expressed viral transcripts and proteins. These results are consistent with our model that cells expressing only the non-HIV promoter-driven reporter were latently infected cells FIG. 1 demonstrates that the subject recombinant nucleic acids can be used to identify a population of latently infected cells. (a) Diagram of the derivation of two-color viruses from the original strains, with a scheme of a classical single reporter virus bearing the reporter gene in the nef ORF. (b) In the 89mASG construct, EGFP is under the control of the SFFV promoter and mApple was added upstream of the transcriptional unit in the position of the nef ATG (see d). (c) In the R7GEmC construct, GFP replaces nef and a whole transcriptional unit (EF1α-mCherry) was inserted downstream. (d) Alignment of regions of interest (from the end of env to the 3'LTR) of the original 89.6 and HXB2 strains deposited in the NCBI database (U39362.2 and NC001802), the starting plasmid and final constructs for each of the HIV clones 89mASG (d, top) and R7GEmC (d, bottom). Insertion points of the first reporter in the nef ORF, the promoter (SFFV or EF1α, respectively) and the second reporter, followed by the end of nef and 5'LTR. Top panel: 89.6 U39362.2 (SEQ ID NO: 30); 89mASG (SEQ ID NO: 31); HXB2 NC001802 (SEQ ID NO: 32); R7/E-/GFP (SEQ ID NO: 33); R7GEmC (SEQ ID NO: 33). FIG. 1D, Bottom panel: rows 2 and 3, middle (SEQ ID NO: 34); rows 2 and 3, right (SEQ ID NO: 35); bottom row, left (SEQ ID NO: 36); bottom row, middle (SEQ ID NO: 37); bottom row, right (SEQ ID NO: 38). (e,f) Cytometric analysis of Jurkat T cells 3 days post-infection, with the indicated titers of 89mASG (e) and R7GEmC (f). (g,h) FACS analysis of 89mASG (g, left) and R7GEmC (h, left) Jurkat T cells sorted 5 days post-infection. Double-negative (uninfected), double-positive (actively infected) and single-positive (latently infected, expressing GFP- or mCherry-only) cells are shown for both viral strains. Fluorescence microscopy images of 89mASG- (g, right) and R7GEmC- (h, right) infected Jurkat T cells. (i) qPCR quantification of proviral DNA in the sorted Jurkat populations, using the primer-probe combination #E for the HIV-1 gag gene and RNAseP for normalization. (j) qPCR quantification of viral transcripts of unspliced (US) gag, singly- (SS) env and multiply-spliced (MS) tat/rev common regions (#E, F, and G; Table 1), normalized for cell GAPDH. (k) Western blot quantification of the HIV proteins vif and gag and the endogenous protein α-actin in the sorted Jurkat populations.

Example 2

Cells Enriched for HIV-Promoter Independent Expression Contain an HIV Genome that can be Reactivated To estimate the fraction of single-positive cells that can be reactivated in terms of HIV expression, the purified cells were treated with drugs reported to reactivate latent HIV, including tumor necrosis factor (TNF)-α (Jordan et al., EMBO J. 2003 Apr. 15; 22(8):1868-77); prostratin, a protein kinase C (PKC) activator (Williams et al., J Biol Chem. 2004 Oct. 1; 279(40), which is hereby incorporated by reference in its entirety); and suberoylanilide hydroxamic acid (SAHA) (Contreras et al., J Biol. Chem. 2009 Mar. 13; 284(11):6782-9, which is hereby incorporated by reference in its entirety), a non-selective histone deacetylase (HDAC) inhibitor. All drugs increased expression of HIV promoter-dependent reporter (FIG. 2A, B top, C, D). Testing of drug combinations that act on different pathways showed maximal reactivation in response to combined SAHA and prostratin treatment, as previously reported by others. In both 89mASG- and R7GEmC-infected latent populations, spontaneous reactivation of latency was observed in the absence of activating molecule, likely reflecting the bi-stable nature of HIV expression.

Due to the integration site of the provirus or the cell state, it is possible that some latently infected cells were classified as double negative because of silencing of both the HIV promoter and the SFFV or EF1α promoter. To address this possibility, the double-negative populations were treated with the same drugs (FIGS. 2A and B, bottom) and found only very limited reactivation, affecting <1% of the population. This implies that the silent HIV provirus in the double-negative population has little to no ability to reactivate in response to stimulation of latent HIV-reactivating cell pathways.

This two-color latency model, which relies on de novo cell infection, can easily be transferred to study the biology of latency in a wide variety of cell types. As an example, two additional T-cell lines commonly used in HIV biology, SupT1 (FIG. 2E) and A301 (FIG. 2F), were infected and sorted. Comparison of the sorted latent populations from those cell lines and Jurkat T cells with an extensive panel of HIV-reactivating drugs—including TNFα, prostratin, SAHA, phorbol myristate acetate (PMA), bryostatin, hexamethylbisacetamide (HMBA), and phytohemagglutinin type-M (PHA-M)(FIG. 2G)—revealed significant differences in drug-independent and drug-dependent reactivation rates. This observation supports the concept that use of a non-clonal, non-stimulus-biased experimental system to study HIV latency, as exemplified by these new viruses, adds significance and robustness to the study of mechanisms for reactivation from latency.

Figure 2:
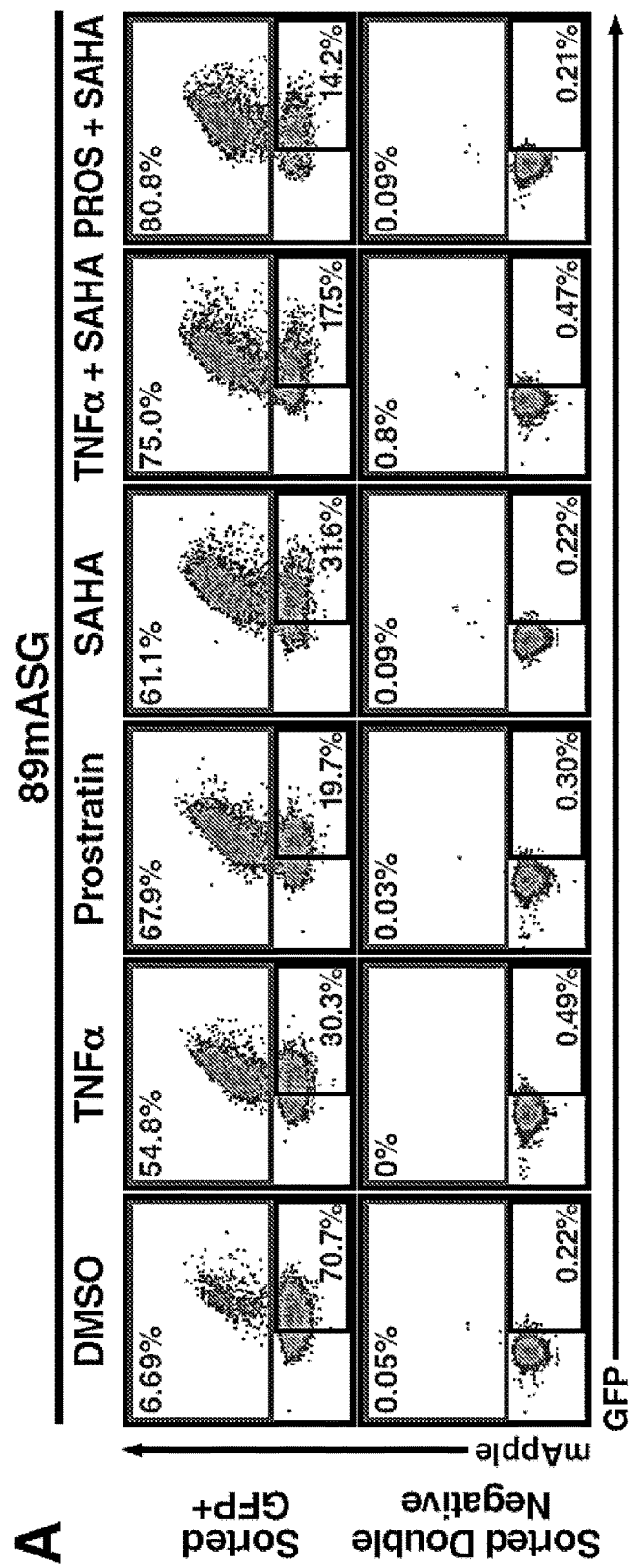
FIGS. 2A-H demonstrate that latently infected cells respond to reactivating drugs FIGS. 3A-F demonstrate that high-throughput screening using two-color HIV-constructs identified new reactivator drugs.
Figure 2:
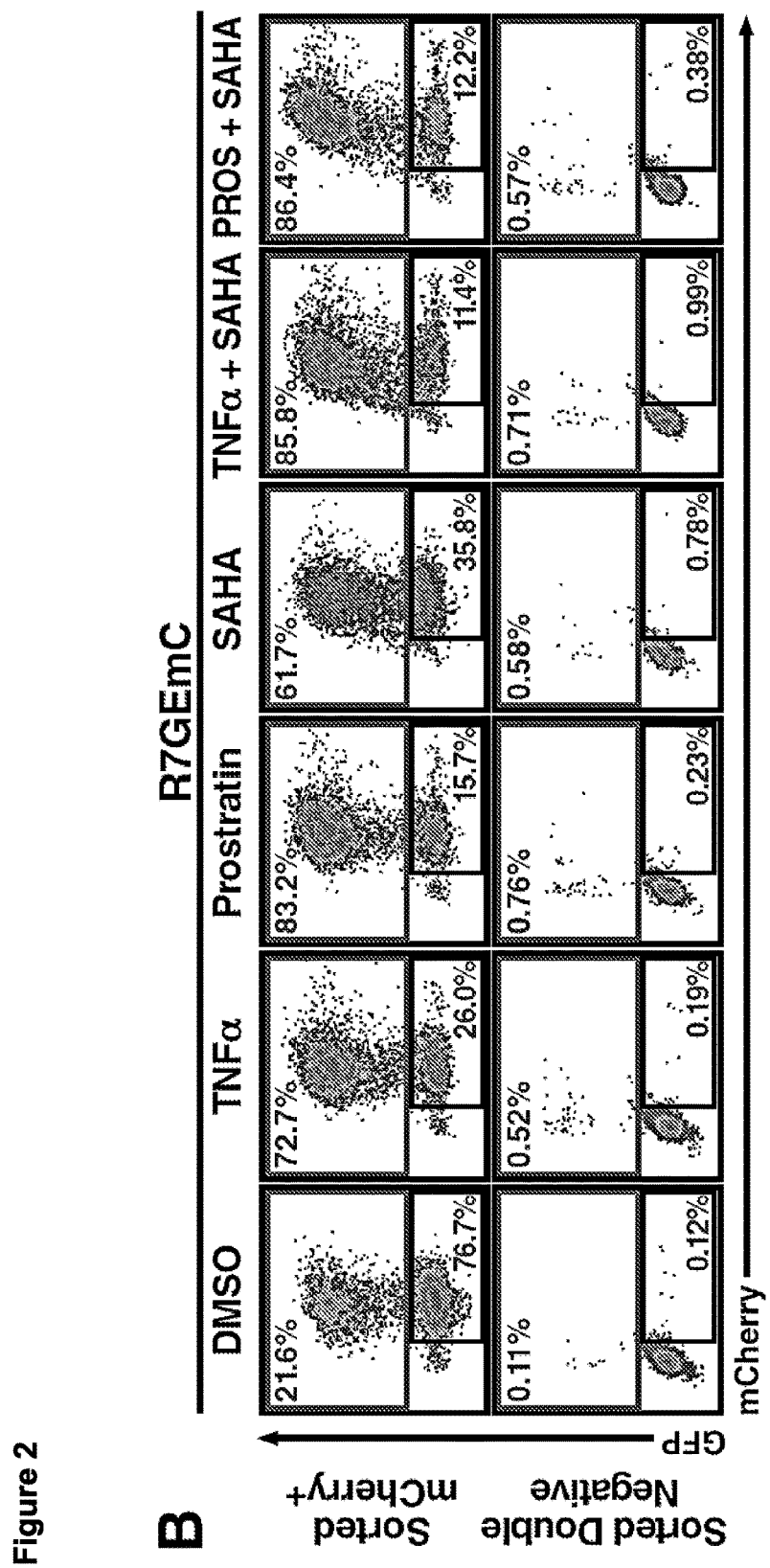
Figure 2:
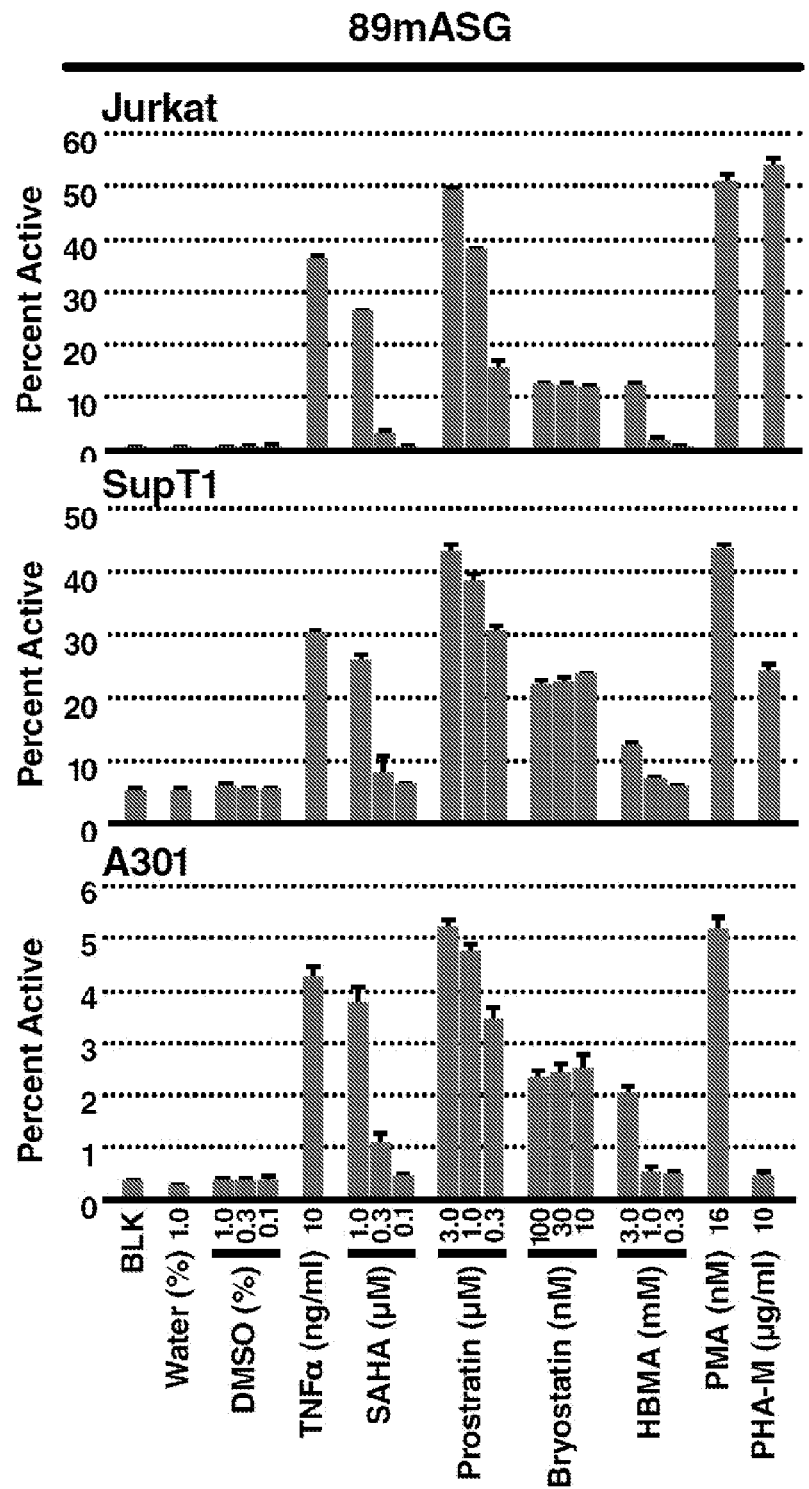
Figure 2:
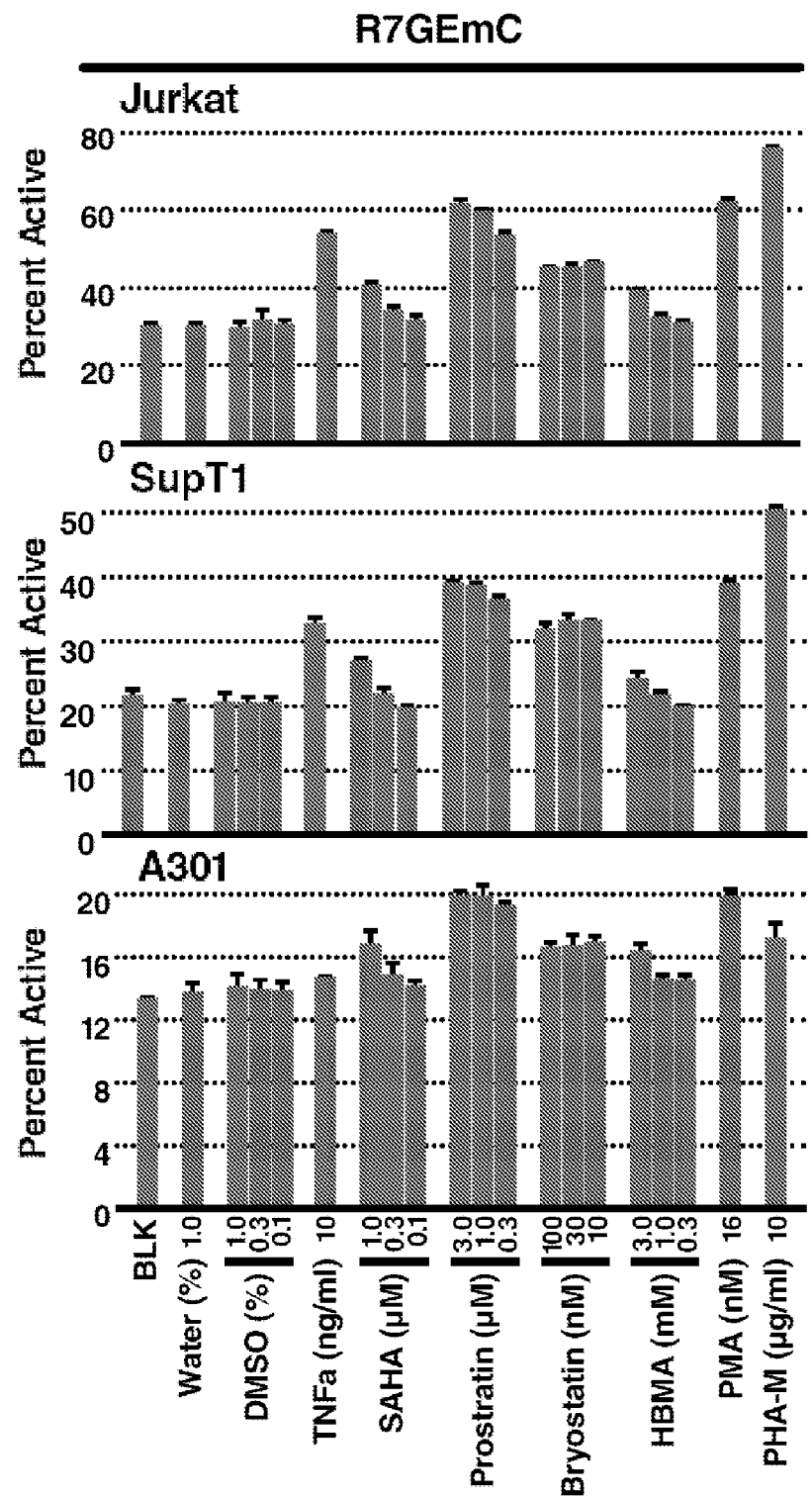

FIG. 2 demonstrates that latently infected cells respond to reactivating drugs (a-d) Five days after sorting, expanded single-positive (latent) and double-negative (uninfected) 89mASG (a, c) and R7GEmC (b, d) Jurkat T cells were treated with 10 ng/ml TNFα, 5 µM prostratin or 2.5 µM SAHA, alone or in combination, as indicated. FACS analysis of a representative treatment (a, b) and histogram quantification of percent population in the active gate for three different experiments (c, d). (e,f) FACS analysis of SupT1 and A301 cell lines, infected with 20 ng p24 of 89mASG (e) or R7GEmC (f) virus. (g,h) A larger panel of latent HIV-reactivating drugs was used at indicated concentrations on sorted, single positive Jurkat, SupT1 and A301 cells. Histograms show quantification of the percent population in the active gate. Data indicate mean±SD for three different treatments. (g) infection with 89mASG (h) infection with R7GEmc.

Example 3

Two-Color HIV Latency Model can be Used for High-Throughput Screening

Next, the power of this novel HIV latency experimental system to identify novel drugs that reactivate latent HIV was tested in a high-throughput format. 5,000 GFP-only-positive cells of 89mASG-infected Jurkat T cells were plated in each well of 384-well plates, coated with a protein solution (Cell-tak) to induce cell attachment and efficient imaging. Preliminary experiments indicated that this protocol yielded the lowest background reactivation and the highest dynamic range (up to 75% cell reactivation with the most effective drug combinations). Cells were treated with 1,120 individual compounds from the Tocriscreen biologically active compound library at 30 µM for 24 hr (drug combinations are shown in FIG. 2A, B) before they were stained with Hoechst. Next, each well was imaged, and total red fluorescence (indicative of reactivated virus) and total blue fluorescence (Hoechst-stained nuclei) were quantified (FIG. 3A).

For most compounds in each plate, a uniform distribution of signal around the median of the negative controls was found, while a notably higher red signal for positive controls that were added in control wells on each plate (TNF, SAHA, Prostratin and their combinations, as described above) was found (FIG. 3A). A group of drugs was also identified that reactivated latent HIV, although to a lesser extent than the positive controls SAHA and prostratin (FIG. 7). Some, such as resveratrol (Krishnan and Zeichner, J Virol. 2004 September; 78(17):9458-73, which is hereby incorporated by reference in its entirety), and genistein (Gozlan et al., J Virol. 1998 October; 72(10):8174-80, which is hereby incorporated by reference in its entirety), have been reported previously to reactivate latent HIV, thereby validating this experimental system. In addition, a number of unanticipated and novel drug classes emerged from the analysis, such as those that act on epidermal growth factor receptor (EGFR), dopamine and serotonin receptors.

Next, using the 89mASG and R7GEmC constructs and FACS analysis, a small group of commercially available drugs and analogs not present in the Tocris library that act on similar pathways were tested to assess their involvement in HIV latency maintenance. Cells were treated with the dopamine receptor agonist apomorphine, used clinically as an emetic and for male impotence, and the D2-receptor-specific analog R-(−)-propylnorapomorphine. In addition, the serotonin receptor antagonists ritanserin and the antipsychotic clozapine, the EGFR receptor antagonists AG555 and AG18 (candidates for specific cancer treatments), the resveratrol analogs piceatannol and pterostilbene (antioxidants with broad and incompletely understood mechanisms of action), the adenosine reuptake inhibitors dilazep and dipyridamole (used as vasodilators and platelet anti-aggregants), the cdc25 dual-phosphatase inhibitor NC95397, the selective Bruton's tyrosine kinase (BTK) inhibitor (−)-terreic acid, and the HMG-CoA synthase inhibitor simvastatin were tested (FIG. 3B, C). Among these, AG555, piceatannol, dilazep and terreic acid produced slight but significant reactivation activity in the 89mASG (FIG. 3B, C) and R7GEmC (FIG. 3B, D) single-positive latent populations. Other molecules were less effective (simvastatin) or had distinct effects in the two HIV clones (apomorphin). In some cases, the intrinsic fluorescence of the molecule produced clear artifacts or false positives (see NSC 95397; FIG. 3B).

A recent study showed that the approved HDAC inhibitor SAHA can reactivate HIV RNA expression in a subset of patients. Thus, it might be of interest to identify compounds that can potentiate HIV reactivation by SAHA or prostratin or TNFα. Sorted latent-cell populations were co-treated for 24 h with low levels of SAHA, prostratin and TNFα, and several effective, non-toxic concentrations of the most promising compounds (FIG. 3E). Interestingly, combining SAHA with terreic acid, dilazep or piceatannol (10 μM) strongly enhanced the effect of low SAHA concentrations on HIV latency on these cells; the same drugs were also synergistic with prostratin. TNFα combinations showed synergistic interaction in most combinations except terreic acid, possibly indicating that the drugs act on the same pathway.

Figure 3:
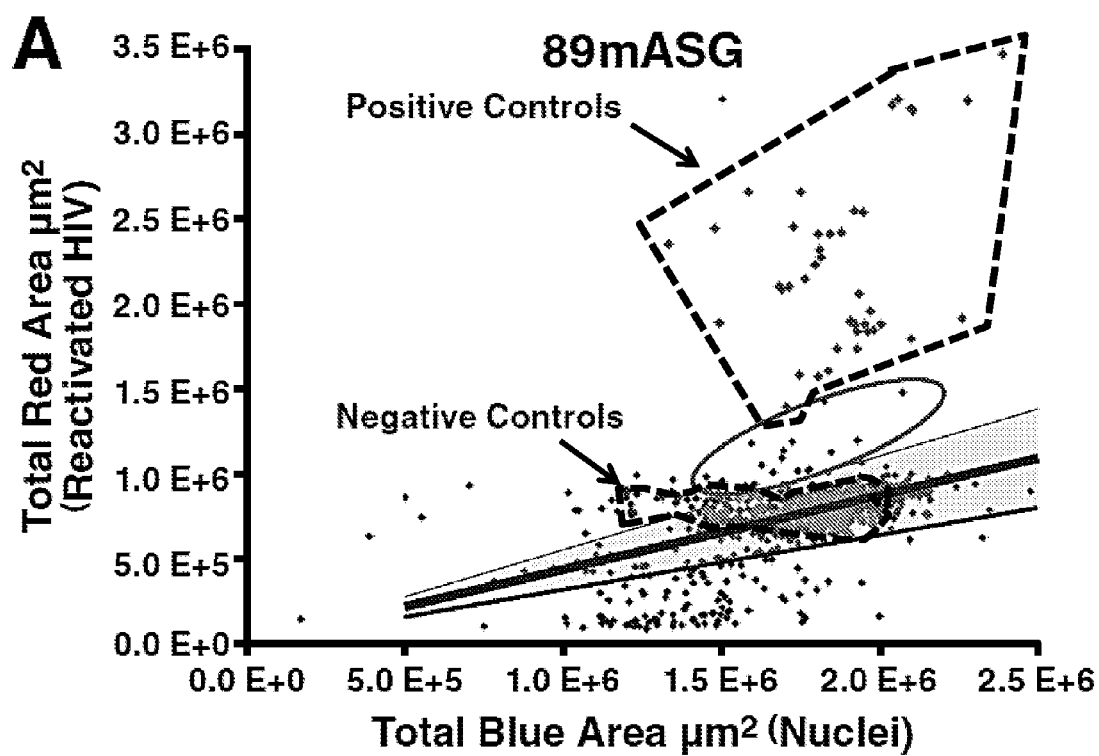
Figure 3:
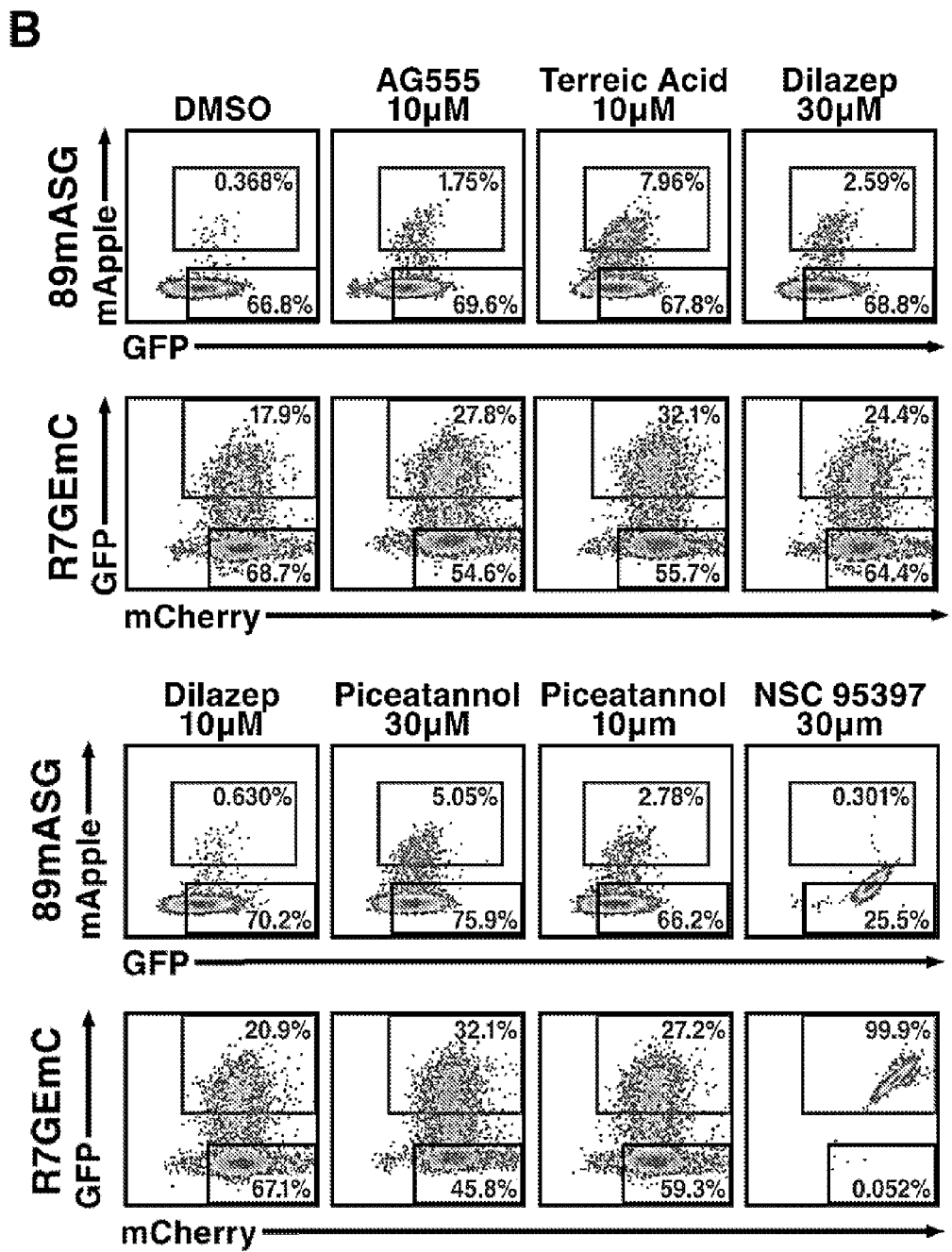
Figure 3:
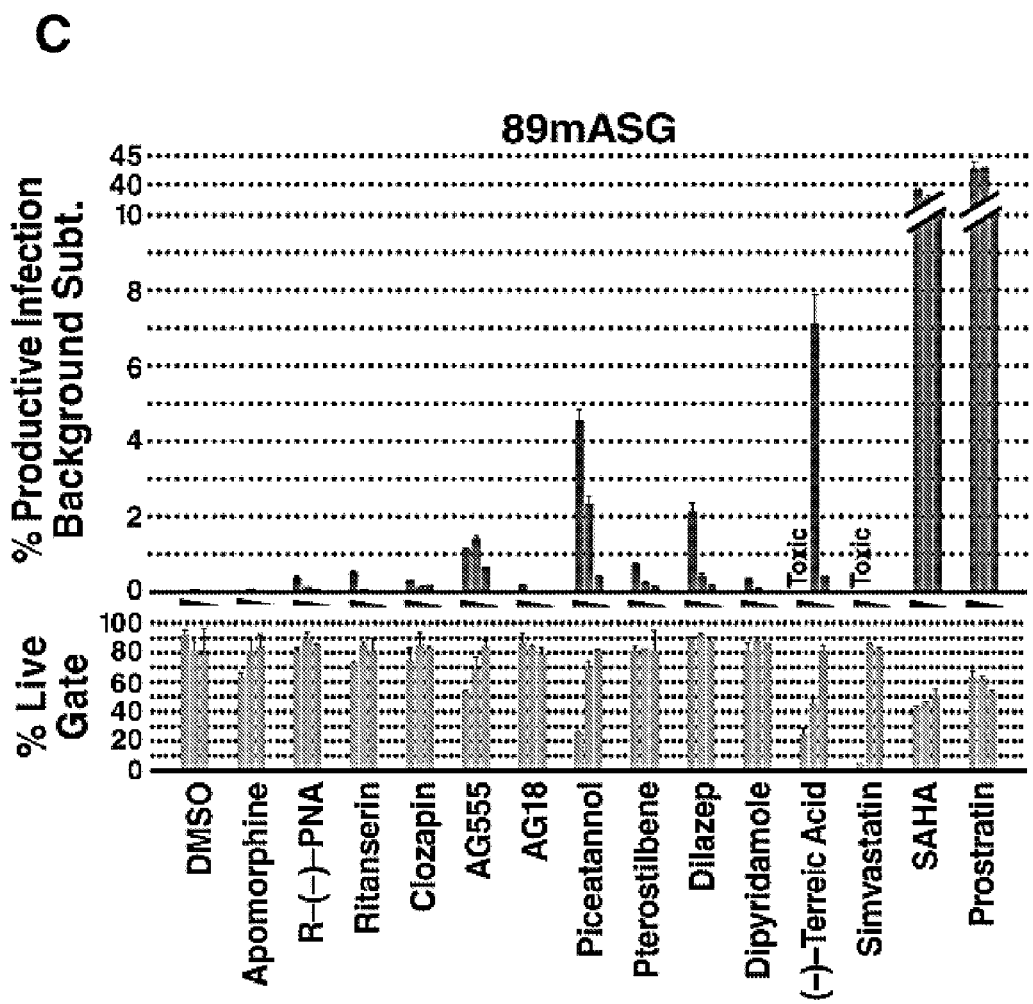
Figure 3:
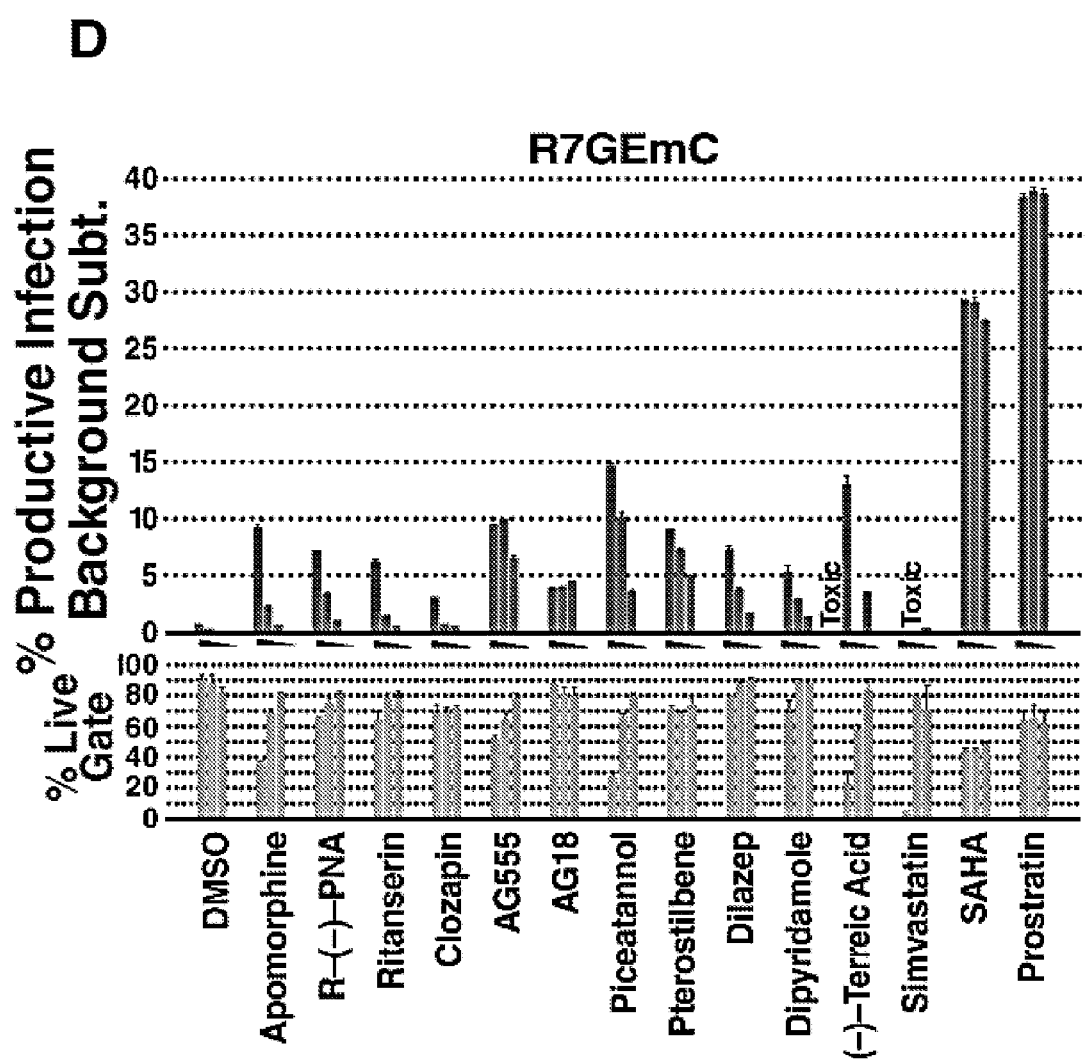
Figure 3:
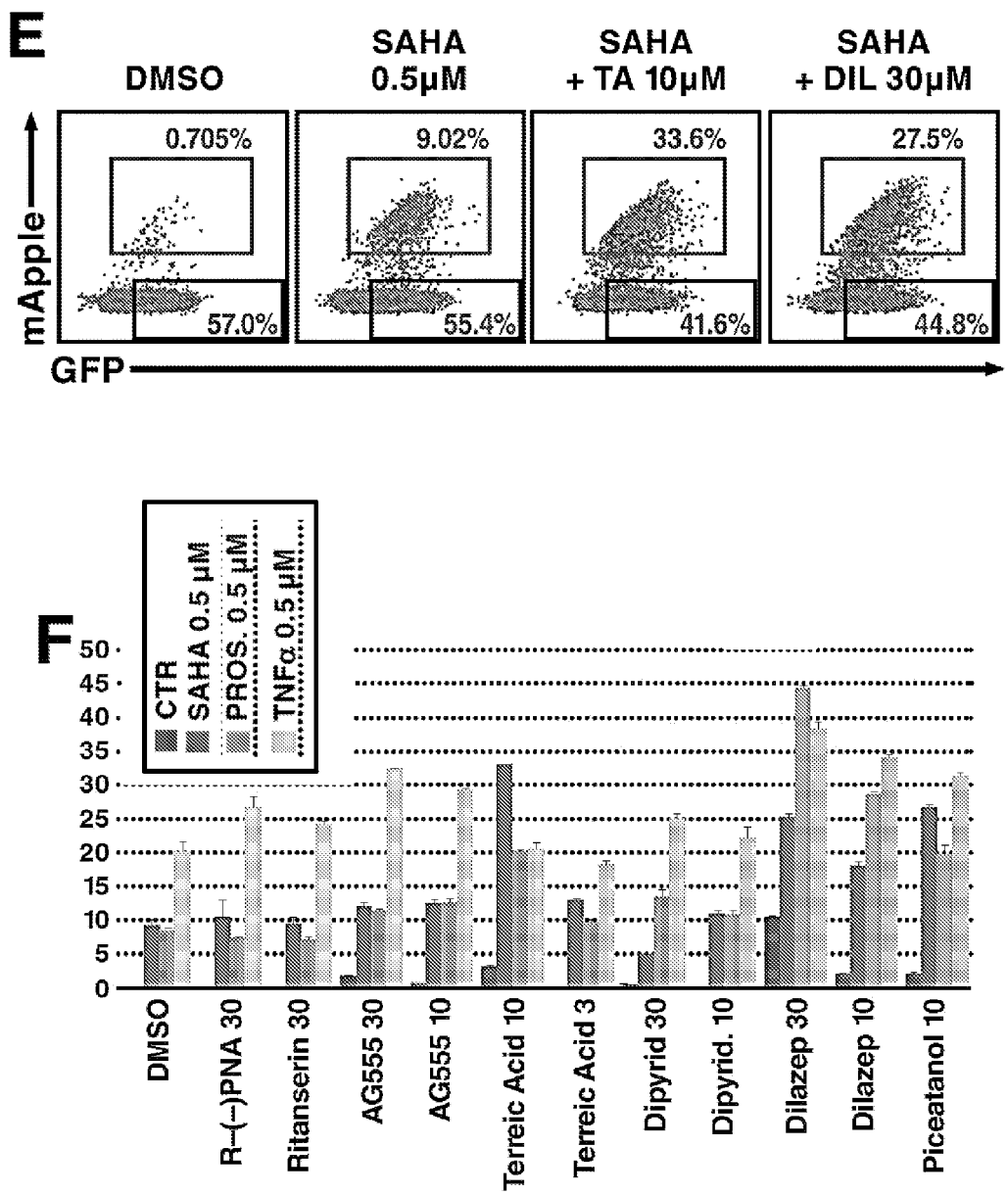

FIG. 3 demonstrates that high-throughput screening using two-color HIV-constructs identified new reactivator drugs.

Sorted 89mASG-infected, GFP-only-positive Jurkat cells were used to test the Tocriscreen drug library for latent HIV reactivation (see Methods). (a) Dot plot showing quantification of total blue area (Hoechst 33342 signal, total cell) against total red area (mApple signal, reactivated HIV). Red dots indicate the position of untreated wells (Negative controls); the shaded area indicates the median±2SD of the red/blue area ratio for negative control wells. Green dots indicate positive control wells, treated with 10 ng/ml TNFα, 5 μM prostratin or 2.5 μM SAHA and their combinations. The ellipse shows novel reactivators identified in the screening (see FIG. 7). (b) Validation of representative hits by FACS analysis. Apomorphine and its analog R-(−)-propylnorapomorphine (PNA), ritanserin, clozapin, AG555, AG18, piceatannol, pterostilbene, dilazep, dipyridamole, terreic acid (TA), simvastatin and NSC95397 were used to validate hits and pathways identified by drug screening. Representative FACS plots of sorted single-positive Jurkat T cells for both viruses. The productive gate contains the reactivated cells. In the last plot on the right, NSC95397 treatment shows alteration of the fluorescent profile by the drug fluorescence. (c,d) Histogram plot of percent population in the productive gate (grey) for each treatment and percentage of cells in the live gate (light blue) for sorted single-positive Jurkat T cells for 89mASG (c) and R7GEmC (d) reporters. Data shown as mean±SD for three different treatments. For each compound, a grey triangle between the histograms indicates decreasing drug concentration (30, 10 and 3 μM). Treatments for which cell death was predominant are labeled TOXIC. (e) FACS analysis of drug treatments combined with 0.5 μM SAHA, 0.5 μM prostratin and 0.5 ng/ml TNFα. Representative FACS plots of sorted GFP-only-positive Jurkat T cells for 89mASG treated with DMSO (control), SAHA (0.5 μM) alone or with terreic acid (10 μM) and dilazep (30 μM). (f) Histogram plot of percent population of the sorted cells in the productive gate for each treatment at indicated concentrations (μM).

FIG. 7 is a table (Table 2) listing compounds from the Tocriscreen drug library that reactivated latent HIV. Compounds with a total red area higher than the median+2 SD for negative control wells are grouped by function. Position (plate-well), name, candidate function and pathways targeted by each compounds are indicated. % reactant indicates the percent increase of the red signal over the median of negative controls, normalized to the most potent combination of reactivating drugs (SAHA 2.5 μM+prostratin 0.5 μM, 100%), #, artifact; see FIG. 3B. EGFR, epidermal growth factor rec. γ; P13K, Phosphoinositide 3-kinase; GPCR, G protein-coupled receptor; 5-HT, 5-hydroxytryptamine; DAG, diaclyglycerol; cAMP, Cyclic adenosine monophosphate; DHFR, Dihydrofolate reductase.

Example 4

Two-Color HIV Constructs Detect Latency in Primary T Cells

Studies of the basic biology of HIV latency have recently emphasized the use of primary cell-based models in an effort to more closely mimic the situation in patients. The use of primary CD4+ T cells from human donors nonetheless remains a challenge, due to low latency establishment rates and limited expansion potential. Resting peripheral CD4+ T cells are generally refractory to HIV infection and require pre-stimulation to achieve efficient infection. Furthermore, T-cell-receptor stimulation and IL2 and/or IL7 supplementation, which is needed for expansion of these cells in culture and for permissive HIV infection, activate the latent HIV provirus, thereby making expansion of latently infected cells unfeasible unless a transformed-like phenotype is induced.

Despite these limitations, a number of experimental model systems for HIV latency have been established in primary CD4+ T cells. The viral constructs were therefore tested for their potential to generate a latent infection in primary CD4+ T cells. Cells were activated with anti-CD3 and anti-CD28-coated dynabeads for 48 hours and infected with both viruses. It was observed that both viruses infected activated CD4+ T cells efficiently, generating an active infection as determined by expression of the HIV promoter-dependent reporters mApple (for 89mASG)(FIG. 5), and GFP (for R7GEmC)(FIG. 4A, B). A very small population of cells expressing only the latency-associated fluorescent marker was also generated in approximately 1 of 100 active infection events. As the GFP signal in 89mASG-infected primary cells was dim and difficult to distinguish from uninfected cells, the R7GEmC construct was used for additional experiments in primary CD4+ cells.

HIV proviral DNA and HIV gag in sorted mCherry-only populations were measured and compared to uninfected and actively infected sorted populations. Viral DNA was detected at high levels in double-positive cells and slightly lower levels in mCherry-positive cells (FIG. 4C). Interestingly, lower but still detectable amounts of proviral DNA were also detected in double-negative cells, indicating that some latent events might be found in this population if EF1α promoter expression is also blocked. As predicted, the HIV gag protein was also detectable in the actively infected population, and absent in latent and uninfected populations (FIG. 4D).

The extent to which mCherry-only-positive populations could be reactivated by further stimulation was next evaluated. After sorting the three populations of mCherry-only-expressing, GFP-positive, and double-negative cells, cells were treated with anti-CD3/28-coated beads to reactivate the latent provirus (FIG. 4E). The latent population responded to this treatment with a 15-18% increase in cells expressing GFP. The double-negative population also responded to a lesser extent, with 0.5-2% reactivation. A population of very bright mCherry-only cells did not respond to treatment, suggesting aberrant integration events or non-reactivatable latent provirus. A subset of less-bright mCherry-only positive cells also responded to prostratin and SAHA treatment (FIG. 4F), suggesting that this population of primary CD4+ T cells contains latently infected, reactivatable cells.

HIV latency in vivo is reported to result, in part, from pre-integration latency, whereby unintegrated proviral DNA (after full retrotranscription) is maintained in a stable cytoplasmic form in a quiescent cell, and can respond to cell activation by de novo integration and productive infection. To rule out pre-integration latency, activated CD4+ T cells were infected with R7GEmC in the presence of the HIV integrase inhibitor raltegravir (FIG. 6A). Under these conditions, no integration-independent expression of the fluorescent proteins after 3 days was observed, thereby excluding pre-integration latency as a major mechanism in this primary-cell-infection model. In addition, raltegravir treatment did not reduce viral reactivation in the mCherry-only-positive population, indicating that all reactivatable latent cells were in a post-integration latency stage (FIG. 6B).

Figure 4:
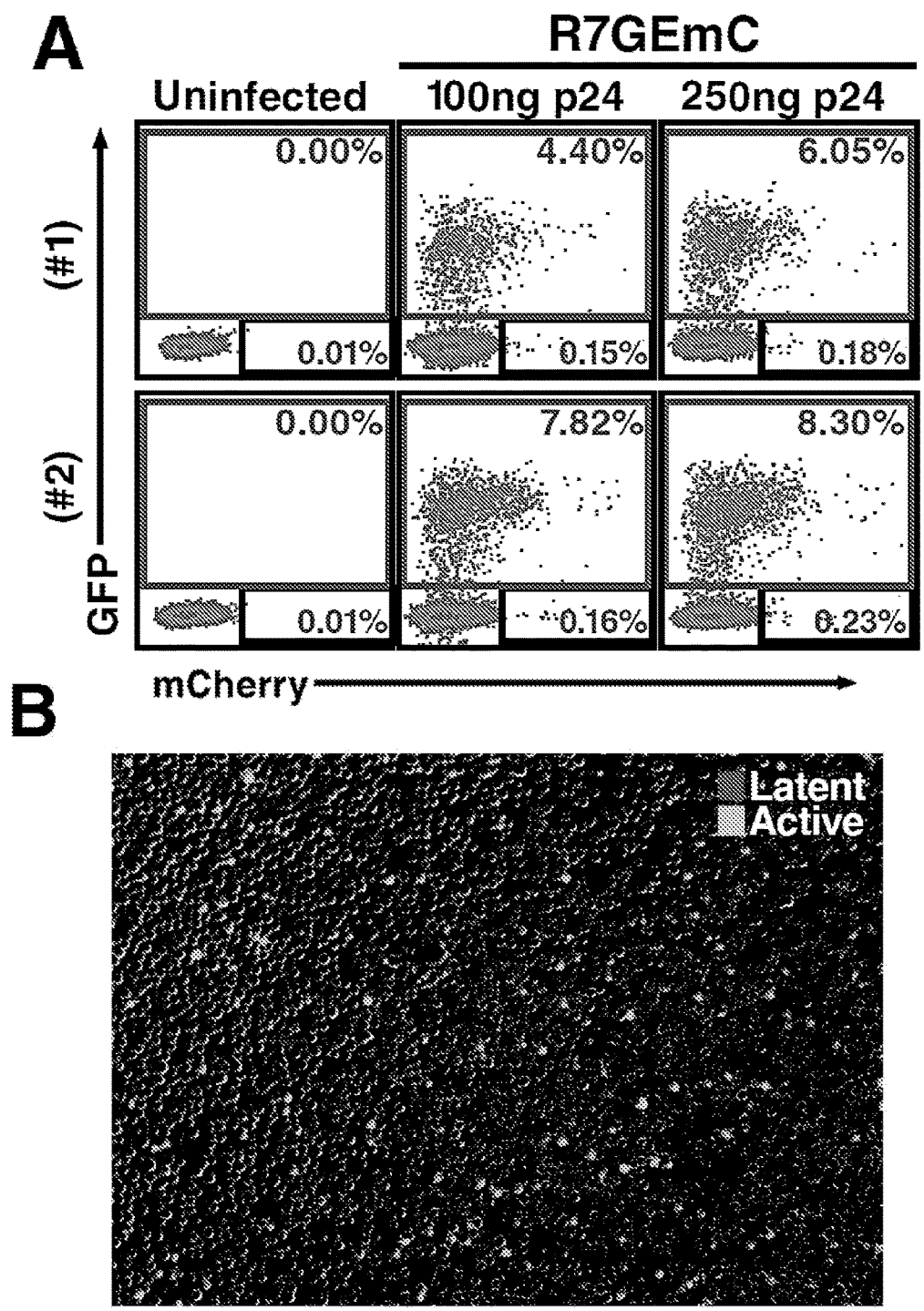
FIGS. 4A-F demonstrate that two-color viruses label a population of latently infected primary T cells.
Figure 4:
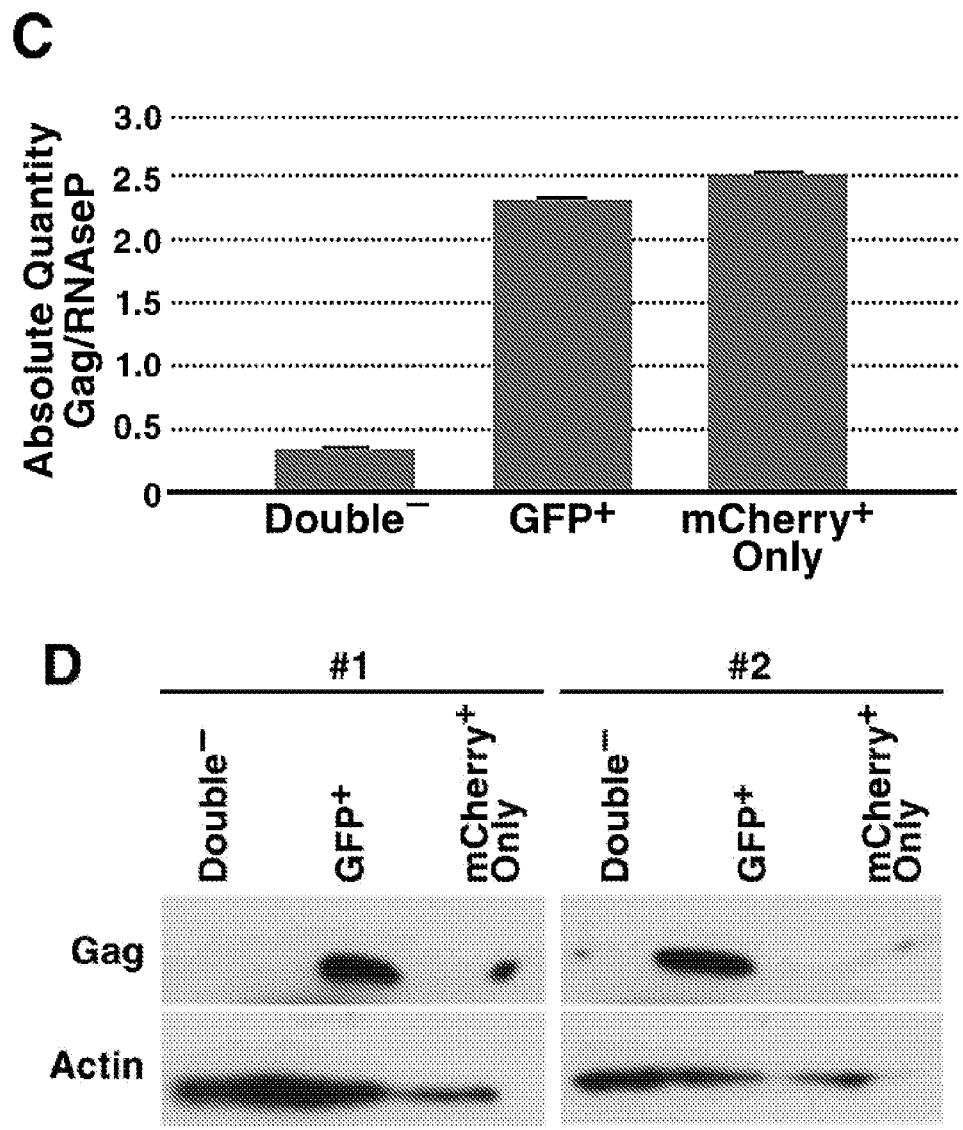
Figure 4:
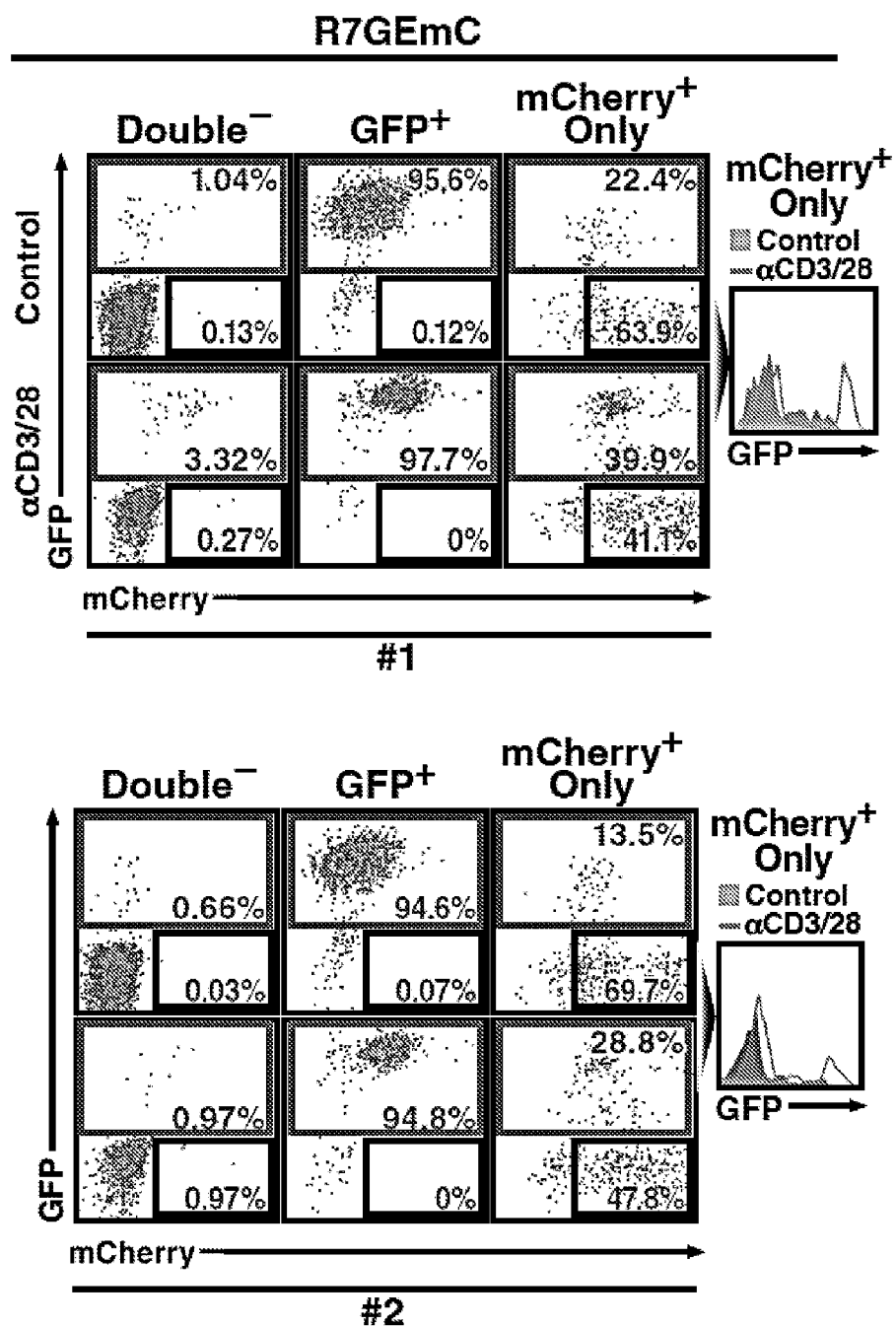
Figure 4:
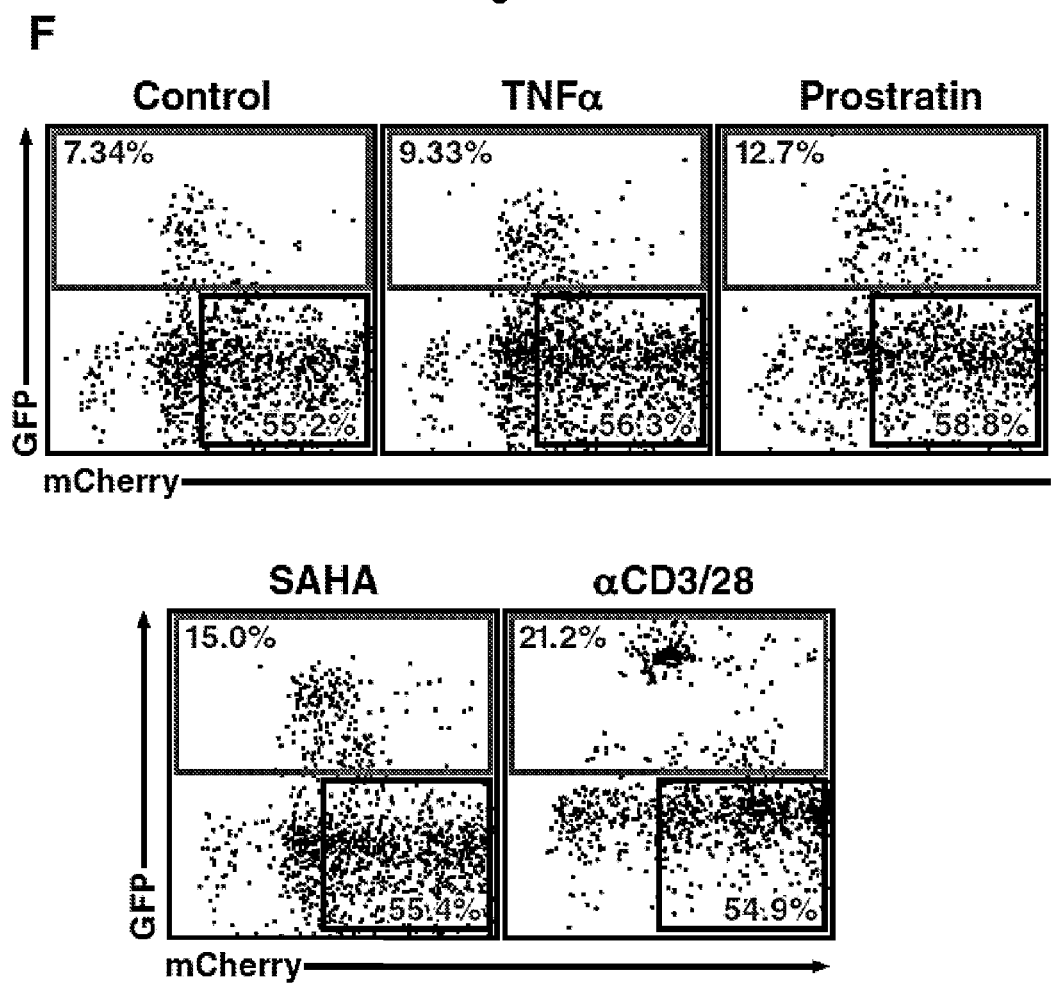

FIG. 4 demonstrates that two-color viruses label a population of latently infected primary T cells. (a) FACS analysis of activated CD4+ T cells from two human donors (#1, #2) infected with R7GEmC at indicated virus amounts. (b) Fluorescence microscopy image of infected CD4+ T cells showing mCherry-positive (latent, red) and GFP-positive (active, green) cells. (c) qPCR quantification of proviral DNA in the sorted populations, using primer-probe combinations for the HIV-1 gag gene and the RNAseP gene for normalization. Data represent mean±SEM for three different donors. (d) Western blot quantification of HIV gag and cell α-actin in sorted CD4+ T cell populations from pooled donors. (e) FACS analysis of sorted CD4+ T cell populations from donors #1 and #2 after 48 h with anti-CD3/CD28-coated Dynabeads (αCD3/28) or left untreated (CTR). Right, histogram plot for the mCherry-only population of each donor in which the treated profile is overlaid on the untreated. (f) Dot plot of mCherry-only population from three pooled donors treated with 10 ng/m, TNFα, 1 μM prostratin, 1 μM SAHA or anti-CD3/CD28-coated Dynabeads (1 bead/cell).

Figure 5:
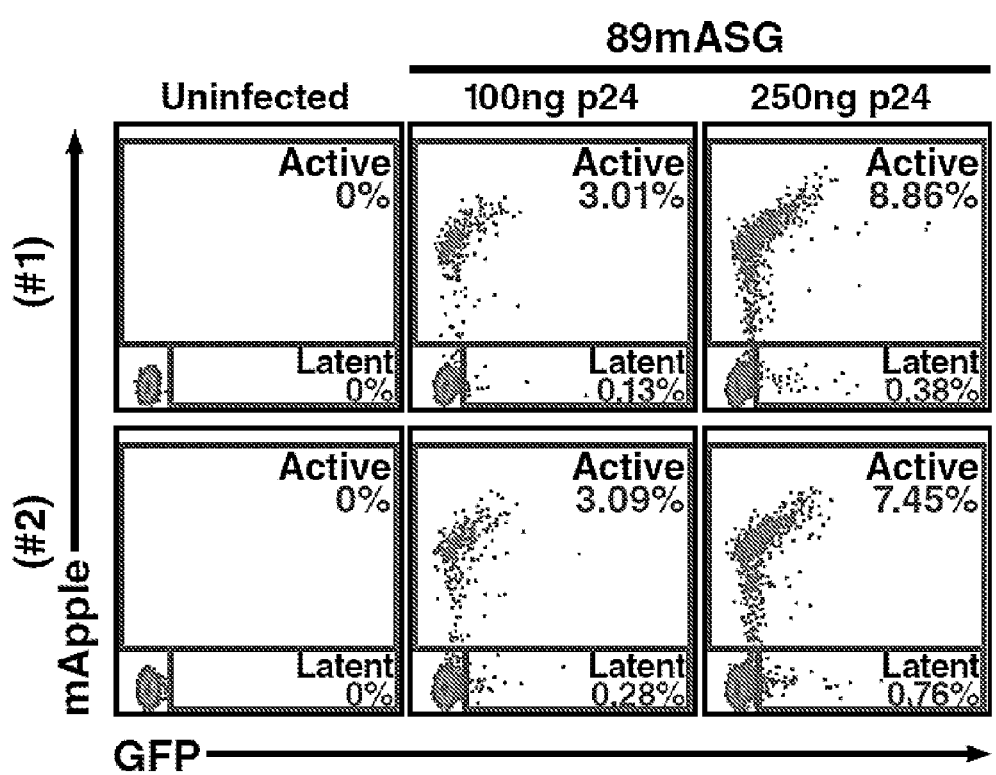
FIG. 5 depicts FACS analysis demonstrating primary T-cell infection with the 89mASG virus

FIG. 5 depicts FACS analysis of activated CD4+ T cells from two human donors (#1, #2) infected with 89mASG virus at the indicated amounts. This analysis demonstrates primary T-cell infection with the 89mASG virus.

FIG. 6 depicts FACS analysis demonstrating primary T-cell infection and reactivation with an integrase inhibitor. (a) FACS analysis of activated CD4+ T cells from two human donors (#1, #2) infected with R7GEMC alone or with 30 μM Raltegravir (RALTE 30). (b) Analysis of sorted CD4+ T-cell populations from donors 1 and 2, after 48 h with anti-CD3/CD28-coated Dynabeads (αCD3/28), alone, with 30 μM Raltegravir, or untreated (CTR).

Example 5

Second Generation Dual-label HIV Reporter Virus

Figure 8:
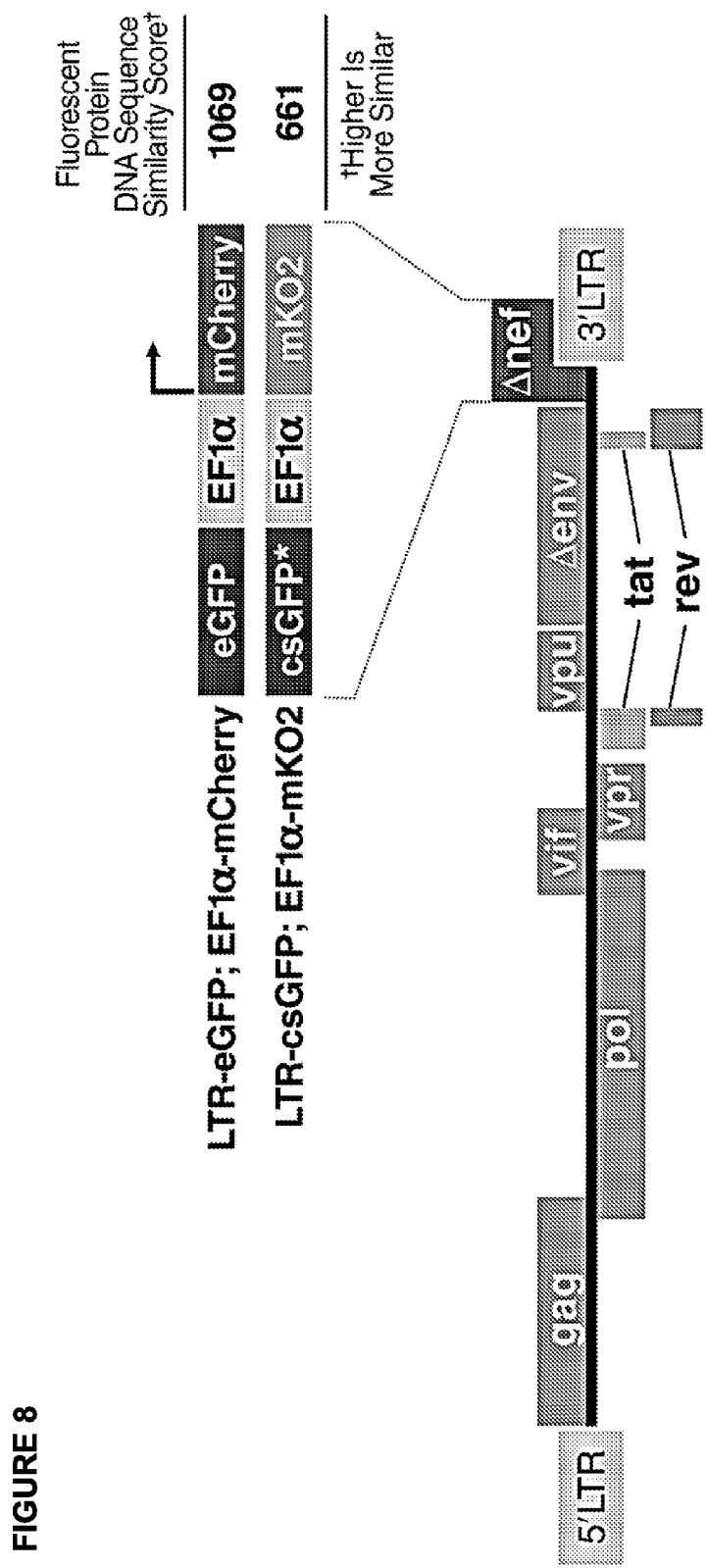
FIG. 8 depicts a schematic representation of dual-labeled HIV-1 reporter viruses described herein.

Second generation dual-labeled virus was constructed, incorporating codon-switched eGFP and monomeric Kusabira Orange-2 fluorescent protein (mKO2). FIG. 8 provides schematic representations of the first- and second-generation dual-labeled HIV-1 reporter viruses. The first generation (top construct in FIG. 8) dual-labeled virus—R7GEmC—incorporates an enhanced green fluorescent protein (eGFP) open reading frame (ORF) in the viral Nef ORF, which is under the control of the HIV-1 promoter (5'LTR). Furthermore, the mCherry ORF is included under the control of the cellular elongation factor 1 alpha promoter (EF1α), and is located between eGFP and the 3' LTR. The second generation (bottom construct in FIG. 8) dual-labeled virus—R7csGmK2—utilizes the same orientation of fluorescent proteins and EF1α promoter, however eGFP is replaced with a codon-switched version of eGFP (csGFP*) and mCherry is replaced by mKO2. Both constructs are Env deleted via an NdeI-induced frameshift mutation.

The nucleic acid sequence of csGFP was generated by nucleotide substitution to replace existing codons of eGFP with synonymous codons for which there exists human codon preference. Multiple substitutions were performed while maintaining the overall percentage of GC content as close to eGFP as possible. The resulting csGFP sequence is provided as SEQ ID NO:42. The completed nucleotide sequence of csGFP was synthetically manufactured and cloned into the dual-labeled virus construct as described herein. The full sequence of R7csGmK2 is provided as SEQ ID NO:43.

Figure 9:
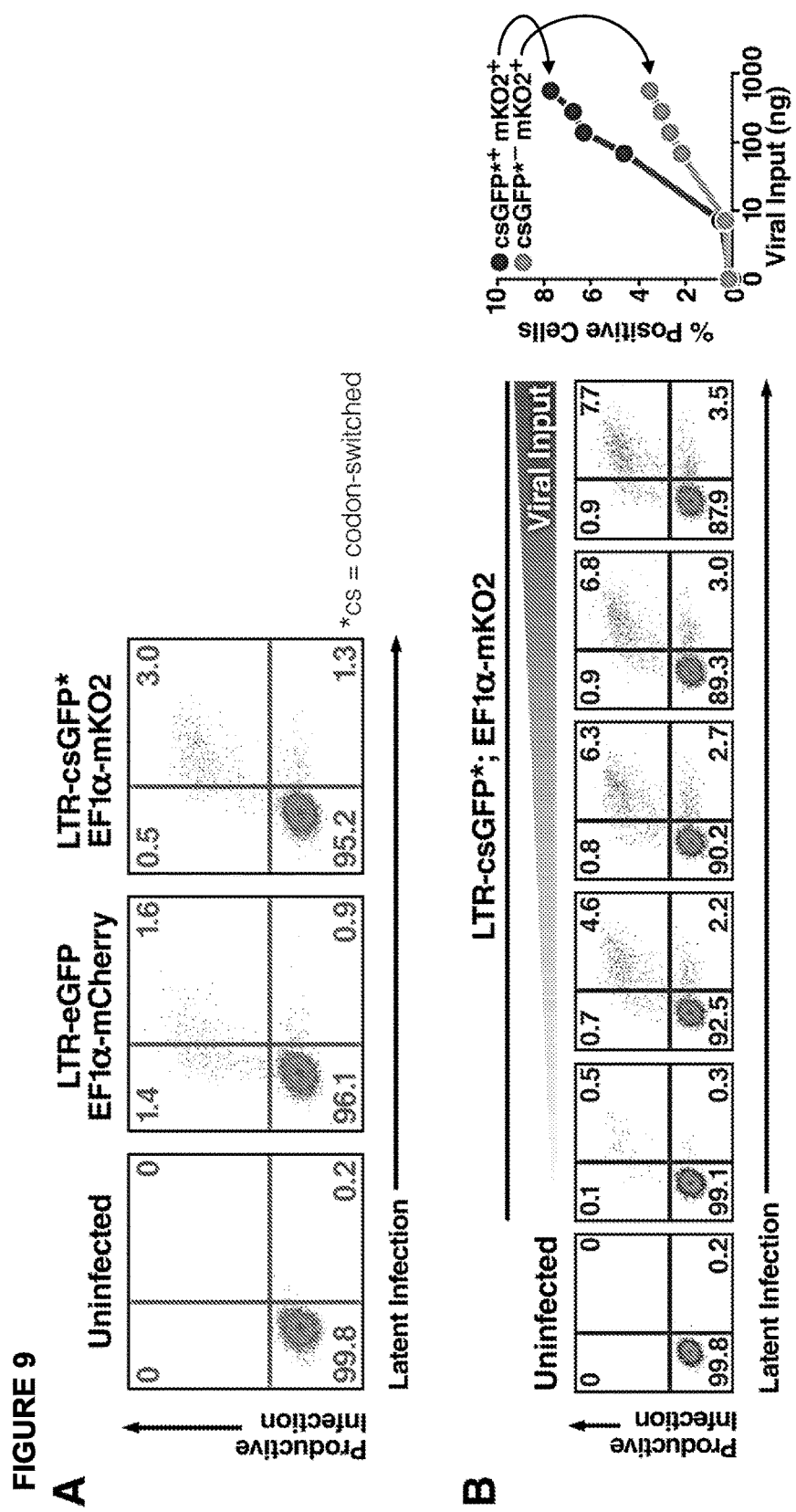
FIGS. 9A-B provide a comparison of the infection profiles of two different generations of reporter viruses.

Second-generation dual-labeled HIV-1 reporter virus (R7csGmK2) was functionally compared to first-generation dual-labeled HIV-1 reporter virus (R7GEmC). FIG. 9A depicts the infection profiles of R7GEmC virus (LTR-eGFP; EF1α-mCherry) and of new dual fluorescence HIV R7csGmK2 (LTR-csGFP; EF1α-mKO2) in activated primary CD4+ T-cells (4 days post infection). Cells were activated with α-CD3/CD28 beads and 20 U/mL IL2 for 3 days prior to infection.

FIG. 9B depicts a titration of mKO2 virus (LTR-csGFP*; EF1α-mKO2) in activated primary CD4+ T-cells (4 days post infection). Cells treated as those in FIG. 9A were infected with different amounts of HIV (input, ng p24 Ag) and analyzed by flow cytometry. FIG. 9B provides both a representative flow cytometry experiment and a graphical representation of the results.

Second-generation dual-labeled HIV-1 reporter virus was further tested for use in the isolation and purification of infected cells at various infection states. FIGS. 10A-D demonstrate that second-generation R7csGmK2 dual-labeled HIV-1 enables purification of productively and latently infected cells. FIG. 10A depicts a FACS gating strategy for purification of double negative (csGFP– mKO2–), productively infected (csGFP+ mKO2+), and latently infected (csGFP– mKO2+) cells (4 days post infection). FIG. 10B depicts RNA expression analysis of uninfected, double-negative, latently infected, and productively infected sorted cells by Taqman RT-qPCR analysis of total RNA isolated from each population (Unspliced (US), singly spliced (SS), and multiply spliced (MS) HIV-1 mRNAs were quantified relative to cellular GAPDH). FIG. 10C depicts protein expression analysis (including Gag-p55, Gag-p24, and Vif) of uninfected, double-negative, latently infected, and productively infected sorted cells by Western blot analysis of each population. FIG. 10D depicts reactivation potential analysis of each sorted population. For reactivation analysis, after sorting, cells were rested for 24 hours prior to treatment with DMSO, αCD3/CD8, SAHA, PMA, or Prostratin for 48 hours. All data shown in FIGS. 10A-D are representative of two donors.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant nucleic acid, comprising:
   (a) a first nucleotide sequence encoding a first reporter polypeptide that produces a first detectable signal, wherein the first nucleotide sequence is operably linked to an immunodeficiency virus promoter and is translated as an early gene; and
   (b) a second nucleotide sequence encoding a second reporter polypeptide that produces a second detectable signal that is distinguishable from the first detectable signal, wherein the second nucleotide sequence is operably linked to a non-immunodeficiency virus promoter, wherein the first and second nucleotide sequences are both positioned between a shared 5' long terminal repeat (LTR) and a shared 3' LTR.

2. The recombinant nucleic acid according to claim 1, wherein the recombinant nucleic acid encodes a transcription-competent immunodeficiency virus and further comprises:
   a functional transactivation response element (TAR); and
   a third nucleotide sequence, wherein the third nucleotide sequence encodes a functional transactivator protein (Tat) and is positioned between the shared 5' long terminal repeat (LTR) and the shared 3' LTR.

3. The recombinant nucleic acid according to claim 2, wherein the immunodeficiency virus is a human immunodeficiency virus (HIV).

4. The recombinant nucleic acid according to claim 3, wherein the HIV is HIV-1 or HIV-2.

5. The recombinant nucleic acid according to claim 1, wherein the first nucleotide sequence is inserted into the locus of an early gene.

6. The recombinant nucleic acid according to claim 5, wherein the early gene is selected from: nef, tat, and rev.

7. The recombinant nucleic acid according to claim 6, wherein the early gene is nef.

8. The recombinant nucleic acid according to claim 5, wherein the early gene is the early gene that is most proximal to the 3' LTR.

9. The recombinant nucleic acid according to claim 5, wherein the first nucleotide sequence is inserted in a manner such that the protein encoded by the early gene is not functional or is not produced.

10. The recombinant nucleic acid according to claim 5, wherein the first nucleotide sequence is inserted in a manner such that a protein encoded by the early gene is a fusion protein comprising the protein encoded by the early gene and the first reporter polypeptide.

11. The recombinant nucleic acid of claim 1, wherein at least one of the first and second reporter polypeptides is a fluorescent protein.

12. The recombinant nucleic acid of claim 11, wherein one of the first and second reporter polypeptides is a red fluorescent protein, and the other is a green fluorescent protein.

13. The recombinant nucleic acid of claim 1, wherein the non-immunodeficiency virus promoter is selected from a group consisting of: an EF1α promoter, a Spleen Focus Forming Virus promoter, a ubiquitin promoter, and a cytomegalovirus (CMV) promoter.

14. The recombinant nucleic acid of claim 1, wherein the 5' LTR comprises the immunodeficiency virus promoter.

15. A virion comprising a recombinant nucleic acid according to claim 1.

* * * * *

UNITED STATES PATENT AND TRADEMARK OFFICE
CERTIFICATE OF CORRECTION

PATENT NO. : 10,106,818 B2
APPLICATION NO. : 14/910665
DATED : October 23, 2018
INVENTOR(S) : Eric M. Verdin et al.

Page 1 of 1

It is certified that error appears in the above-identified patent and that said Letters Patent is hereby corrected as shown below:

In the Specification

Column 17, Line 33, replace "spino" with --spiro--

Column 23, Line 5, replace "SW" with --SIV--

Column 81, Line 49, replace "A microliter(s)" with --µl, microliter(s)--

Signed and Sealed this
Nineteenth Day of March, 2019

Andrei Iancu
*Director of the United States Patent and Trademark Office*